US010947509B2

(12) United States Patent
Ferber

(10) Patent No.: US 10,947,509 B2
(45) Date of Patent: Mar. 16, 2021

(54) CELL POPULATIONS, METHODS OF TRANSDIFFERENTIATION AND METHODS OF USE THEREOF

(71) Applicants: ORGENESIS LTD., Tel Aviv (IL); TEL HASHOMER MEDICAL RESEARCH INFRASTRUCTURE AND SERVICES LTD., Ramat Gan (IL)

(72) Inventor: Sarah Ferber, Tel Aviv (IL)

(73) Assignees: ORGENESIS LTD., Tel Aviv (IL); TEL HASHOMER MEDICAL RESEARCH INFRASTRUCTURE AND SERVICES LTD., Ramat Gan (IL)

(*) Notice: Subject to any disclaimer, the term of this patent is extended or adjusted under 35 U.S.C. 154(b) by 245 days.

(21) Appl. No.: 15/961,907

(22) Filed: Apr. 25, 2018

(65) Prior Publication Data

US 2018/0340146 A1 Nov. 29, 2018

Related U.S. Application Data

(62) Division of application No. 14/897,262, filed as application No. PCT/IB2014/002164 on Jun. 13, 2014, now Pat. No. 9,982,236.

(60) Provisional application No. 61/834,759, filed on Jun. 13, 2013, provisional application No. 61/834,767, filed on Jun. 13, 2013.

(51) Int. Cl.
*C12N 5/071* (2010.01)
*G01N 33/50* (2006.01)
*A61K 38/17* (2006.01)
*A61K 35/407* (2015.01)
*A61K 35/38* (2015.01)

(52) U.S. Cl.
CPC .............. *C12N 5/067* (2013.01); *A61K 35/38* (2013.01); *A61K 35/407* (2013.01); *A61K 38/1709* (2013.01); *C12N 5/0676* (2013.01); *G01N 33/5005* (2013.01); *C12N 2501/415* (2013.01); *C12N 2501/60* (2013.01); *C12N 2506/14* (2013.01); *C12N 2510/00* (2013.01); *C12N 2710/10343* (2013.01); *C12N 2830/30* (2013.01)

(58) Field of Classification Search
CPC .............. C12N 5/067; C12N 2501/415; C12N 2710/10343; C12N 2830/30; C12N 2510/00; G01N 33/5005; A61K 35/407
See application file for complete search history.

(56) References Cited

U.S. PATENT DOCUMENTS

| | | |
|---|---|---|
| 4,522,811 A | 6/1985 | Eppstein et al. |
| 4,737,323 A | 4/1988 | Martin et al. |
| 4,837,028 A | 6/1989 | Allen |
| 4,837,316 A | 6/1989 | Sekine et al. |
| 4,980,286 A | 12/1990 | Morgan et al. |
| 4,992,417 A | 2/1991 | Katsovannis et al. |
| 5,082,670 A | 1/1992 | Gage et al. |
| 5,328,470 A | 7/1994 | Nabel et al. |
| 5,424,286 A | 6/1995 | Eng |
| 5,427,940 A | 6/1995 | Newgard |
| 5,703,055 A | 12/1997 | Feigner et al. |
| 5,741,673 A | 4/1998 | Montminy et al. |
| 5,849,989 A | 12/1998 | Edlund |
| 5,858,973 A | 1/1999 | Habener et al. |
| 5,942,435 A | 8/1999 | Wheeler |
| 6,114,113 A | 9/2000 | McLaughlin et al. |
| 6,143,293 A | 11/2000 | Weiss et al. |
| 6,242,666 B1 | 6/2001 | Sarvetnick et al. |
| 6,379,962 B1 | 4/2002 | Holy et al. |
| 6,716,824 B1 | 4/2004 | Bruincardi |
| 6,774,120 B1 | 8/2004 | Ferber |
| 7,029,915 B2 | 4/2006 | Yang |
| 7,517,856 B2 | 4/2009 | Cohen et al. |
| 7,524,492 B2 | 4/2009 | Sharma |
| 7,722,894 B2 | 5/2010 | Wang et al. |
| 8,119,405 B2 | 2/2012 | Ferber |
| 8,778,899 B2 | 7/2014 | Ferber |
| 9,359,472 B2 | 6/2016 | Nicholson et al. |
| 2001/0013134 A1 | 8/2001 | Sarvetnick et al. |
| 2002/0001610 A1 | 1/2002 | Cohen et al. |

(Continued)

FOREIGN PATENT DOCUMENTS

| | | |
|---|---|---|
| EP | 0264166 | 4/1988 |
| EP | 1354942 | 10/2003 |

(Continued)

OTHER PUBLICATIONS

Werth et al., Hepatic expression of glutamine synthetase in rats is controlled by STAT5 and TCF transcription factors. Hepatology, vol. 44, No. 4 (Oct. 2006) pp. 967-975. (Year: 2006).*

(Continued)

*Primary Examiner* — Kara D Johnson
(74) *Attorney, Agent, or Firm* — Mark S. Cohen; Pearl Cohen Zedek Latzer Baratz LLP

(57) ABSTRACT

The present invention provides methods for the sequential and temporally-regulated administration of pancreatic transcription factors to induce non-pancreatic cells to transdifferentiate and mature along the pancreatic β-cell lineage. The present invention also provides methods for identifying, isolating and enriching transdifferentiation predisposed cells and methods for treating a degenerative pancreatic disorder such as diabetes.

12 Claims, 22 Drawing Sheets

Specification includes a Sequence Listing.

(56) References Cited

U.S. PATENT DOCUMENTS

| | | |
|---|---|---|
| 2002/0081725 A1 | 6/2002 | Tsang et al. |
| 2003/0078672 A1 | 4/2003 | Shapiro et al. |
| 2003/0138948 A1 | 7/2003 | Fisk et al. |
| 2003/0219894 A1 | 11/2003 | Seino et al. |
| 2004/0213769 A1 | 10/2004 | Ferber |
| 2005/0003010 A1 | 1/2005 | Cohen et al. |
| 2005/0090465 A1 | 4/2005 | Ferber |
| 2006/0122104 A1 | 6/2006 | Presnell et al. |
| 2006/0205072 A1 | 9/2006 | Uchida et al. |
| 2007/0014772 A1 | 1/2007 | Cohen et al. |
| 2007/0081976 A1 | 4/2007 | Cohen et al. |
| 2007/0111310 A1 | 5/2007 | Cohen et al. |
| 2009/0053249 A1 | 2/2009 | Qi et al. |
| 2009/0239298 A1 | 9/2009 | Gerecht et al. |
| 2010/0145470 A1 | 6/2010 | Cohen et al. |
| 2010/0226976 A1 | 9/2010 | Machluf et al. |
| 2010/0233239 A1 | 9/2010 | Berkland et al. |
| 2010/0247652 A1 | 9/2010 | Ilan et al. |
| 2011/0280842 A1 | 11/2011 | Melton et al. |
| 2012/0210451 A1 | 8/2012 | Shimizu et al. |
| 2014/0147452 A1 | 5/2014 | Izraeli et al. |
| 2015/0017727 A1 | 1/2015 | Ferber |
| 2015/0050247 A1 | 2/2015 | Machluf et al. |
| 2015/0051148 A1 | 2/2015 | Cohen et al. |
| 2015/0352144 A1 | 12/2015 | Cohen et al. |
| 2016/0101133 A1 | 4/2016 | Basu et al. |
| 2016/0130559 A1 | 5/2016 | Ferber |
| 2016/0220616 A1 | 8/2016 | Ferber |
| 2016/0354474 A1 | 12/2016 | Cohen et al. |
| 2017/0096500 A1 | 4/2017 | Cohen et al. |
| 2017/0290954 A1 | 10/2017 | Cohen et al. |

FOREIGN PATENT DOCUMENTS

| | | |
|---|---|---|
| JP | 2011-223993 A | 11/2011 |
| WO | WO 1994/008598 | 4/1994 |
| WO | WO 1995/005463 | 2/1995 |
| WO | WO 1995/035073 A1 | 12/1995 |
| WO | WO 1997/020075 | 6/1997 |
| WO | WO 1997/049728 | 12/1997 |
| WO | WO 2000/072885 A2 | 12/2000 |
| WO | WO 2003/033697 | 4/2003 |
| WO | WO 2003/078636 A1 | 9/2003 |
| WO | WO 2004/098646 A1 | 11/2004 |
| WO | WO 2008/013737 A2 | 1/2008 |
| WO | WO 2009/126927 A2 | 10/2009 |
| WO | WO 2010/022395 | 2/2010 |
| WO | WO 2011/159726 | 12/2011 |
| WO | WO 2013/124855 A1 | 1/2013 |
| WO | WO 2013/021389 | 2/2013 |
| WO | WO/2014/207578 A2 | 12/2014 |
| WO | WO 2016/108237 A1 | 7/2016 |
| WO | WO 2017/118979 A1 | 7/2017 |
| WO | WO 2017/175229 A1 | 10/2017 |
| WO | WO 2018/207179 A1 | 11/2018 |

OTHER PUBLICATIONS

Huch et al., In vitro expansion of single Lgr5+ liver stem cells induced by Wnt-driven regeneration. Nature, vol. 494 (Jan. 27, 2013) pp. 247-250. (Year: 2013).*
Cohen et al., The Wnt/β-catenin pathway determines the predisposition and efficiency of liver—to-pancreas reprogramming, Hepatology, vol. 68, No. 4 (Oct. 2018) pp. 1589-1603. (Year: 2018).*
Ahlgren et al. "The Morphogenesis of the Pancreatic Mesenchymal is Uncoupled From That of the Pancreatic Epithelium in IPF1/PDX1-Deficient Mice." Dev. 122(1996):1409-1416.
Akbarpour et al. "Insulin B chain 9-23 gene transfer to hepatocytes protects from type 1 diabetes by inducing Ag-specific FoxP3+ Tregs", Sci Transl Med. May 27, 2015;7(289):289ra81.
Ambasudhan et al. "Direct reprogramming of adult human fibroblasts to functional neurons under defined conditions", Cell Stem Cell. Aug. 5, 2011;9(2):113-8.

Amman et al. "Tightly Regulated tac Promoter Vectors Useful for the Expression of Unfused and Fused Proteins in *Escherichia coli*" Gene. Sep. 30, 1988;69(2):301-15.
Anderson et al. "Human Gene Therapy." Nature. 392(1998):25-30.
Aviv et al. "Exendin-4 promotes liver cell proliferation and enhances the PDX-1 induced liver to pancreas transdifferentiation process", J Biol Chem. Nov. 27, 2009;284(48):33509-20.
Baldari et al. "A novel leader peptide which allows efficient secretion of a fragment of human interleukin 1 beta in *Saccharomyces cerevisiae*" EMBO J. Jan. 1987;6(1):229-34.
Banerji et al. "A Lymphocyte-Specific Cellular Enhancer is Located Downstream of the Joining Region in Immunoglobulin Heavy Chain Genes." Ceil. 33('1983):729-740.
Banga et al. "In vivo reprogramming of Sox9+ cells in the liver to insulin-secreting ducts", PNAS Sep. 18, 2012, vol. 109, No. 38, pp. 15336-15341.
Ben Nasr et al. "Co-transplantation of autologous MSCs delays islet allograft rejection and generates a local immunoprivileged site", Acta Diabetol. Oct. 2015;52(5):917-27.
Ber et al. "Functional, persistent, and extended liver to pancreas transdifferentiation", J Biol Chem. Aug. 22, 2003;278(34):31950-7.
Bernardo et al. "Pancreatic transcription factors and their role in the birth, life and survival of the pancreatic beta cell", Mol Cell Endocrinol. Nov. 6, 2008;294(1-2):1-9.
Berneman-Zeitouni et al. "The Temporal and Hierarchical Control of Transcription Factors-Induced Liver to Pancreas Transdifferentiation", Plos One 1 Feb. 2014, vol. 9 | Issue 2, pp. 1-10.
Berneman et al. "Hierarchical Sequential Administration of Pancreatic Transcription Factors That Leads to Pancreas Organogenesis Improves Liver to Pancreas Reprogramming Process" In Human Gene Therapy May 1, 2010 (vol. 21, No. 5, pp. 640-641).
Bhandari et al. "cloning, nucleotide sequence and potential regulatory elements of the glutamine synthetase gene from murine 3t3-I1 adipocytes" proc. natl. acad. sci. Aug. 1988, vol. 85, pp. 5789-5793.
Bonal et al. "Genes controlling pancreas ontogeny", Int J Dev Biol. 2008;52(7):823-35.
Bonner-Weir et al. "New Sources of Pancreatic B-Cells." Nat Biotechnol. Jul. 2005;23(7):857-61.
Borowiak "The new generation of beta-cells: replication, stem cell differentiation, and the role of small molecules", Rev Diabet Stud. 2010 Summer;7(2):93-104.
Bretheron-Watt el al. "Insulin Upstream Factor 1 and a Novel Ubiquitous Factor Bind to the Human Islet Amyloid Polypeptide/Amylin Gene Promoter." Biochem. J. 313.2(1998):495-502.
Brevini et al. "No shortcuts to pig embryonic stem cells", 2010, Theriogenology, vol. 74, pp. 544-550.
Brun et al. "A focus on the role of Pax4 in mature pancreatic islet beta-cell expansion and survival in health and disease", J Mol Endocrinol. Feb. 2008;40(2):37-45.
Byrne et al. "Multiplex Gene Regulation; A Two-Tiered Approach to Transgene Regulation in Transgenic Mice," PNAS. 86(1989):5473-5477.
Calame et al. "Transcriptional Controlling Elements in the Immunoglobulin and T Cell Receptor Loci." Adv Immunol. 1988;43:235-75.
Camper et al. "Postnatal Repression of the a-Fetaprotein Gene is Enhancer Independent." Genes Dev. 3(1989):537-546.
Campos et al. "Divergent Tissue-Specific and Development Expression of Receptors for Glucapon and Glucagon-Like Peptide-1 in the Mouse." Endocrinology. May 1994;134(5):2156-64.
Cao et al. "External factors are necessary for Pdx1 transfected hepatic cells to transdifferentiate into functional pancreatic endocrine insulin-producing cells'" Diabetes. Jun. 1, 2004;53:A434. Abstract.
Cao et al. "High glucose is necessary for complete maturation of Pdx1-VP16 expressing hepatic cells into functional insulin-producing cells", Diabetes. Dec. 2004;53(12):3168-78.
Caplan et al. "Adult Mesenchymal Stem Cells for Tissue Engineering Versus Regenerative Medicine." J. Cell. Physiol. 213{2007):341-347.
Chakrabarti et al. "Transcription factors direct the development and function of pancreatic beta cells", Trends Endocrinol Metab. Mar. 2003;14(2):78-84.

(56) References Cited

OTHER PUBLICATIONS

Chen et al. "Gene Therapy for Brain Tumors: Regression of Experimental Gliomas by Adenovirus-Mediated Gene Transfer in vivo" PNAS. 91(1994):3054-3057.
Chiang et al. "The role of the Wnt signaling pathway in incretin hormone production and function" Frontiers in physiology. Jul. 2012 12;3:273.
Collombat et al. "Opposing actions of Arx and Pax4 in endocrine pancreas development", Genes Dev. Oct. 15, 2003;17(20):2591-603.
Collombat et al. "Specifying pancreatic endocrine cell fates", Mech Dev. Jul. 2006;123(7):501-12.
Cozar-Castellano et al. "Molecular engineering human hepatocytes into pancreatic beta cells for diabetes therapy", Proc Natl Acad Sci U S A. May 31, 2005;102(22):7781-2.
D'Amour et al. "Efficient differentiation of human embryonic stem cells to definitive endoderm", Nat Biotechnol. Dec. 2005;23(12):1534-41.
Dunbar et al. "Identification of Betaceiluiin as a Major Peptide Growth Factor in Milk: Purification, Characterization and Molecular Cloning of Bovine Betaceiluiin." Biochem. J. 344(1999):713-72.
Eberhard et al. "The pancreatic beta-cell in the islet and organ community", Curr Opin Genet Dev. Oct. 2009;19(5):469-75.
Edlund et al. "Cell-Specific Expression of the Rat insulin Gene: Evidence for Role of Two Distinct 5' Flanking Elements." Science. 230(1985):912-916.
Ferber et al. "Pancreatic and duodenal homeobox gene 1 induces expression of insulin genes in liver and ameliorates streptozotocin-induced hyperglycemia", Nat Med. May 2000;6(5):568-72.
Figliuzzi et al. "Mesenchymal stem cells help pancreatic islet transplantation to control type 1 diabetes", World J Stem Cells. Apr. 26, 2014;6(2):163-72. *.
Furukawa et al. "Possible involvement of atypical protein kinase C (PKC) in glucose sensitive expression of the human insulin gene: DNA-binding activity and transcriptional activity of pancreatic and duodenal homeobox gene-1 (PDX-1) are enhanced via calphostin C-sensitive but phorbol 12-myristate 13-acetate (PMA) and Gö 6976- insensitive pathway", Endocr J. Feb. 1999;46(1):43-58.
Gefen-Halevi et al. "NKX6.1 promotes PDX-1-induced liver to pancreatic β-cells reprogramming", Cell Reprogram. Dec. 2010;12(6):655-64.
GenBank Accession No. AAA18355.1, May 25, 1994.
GenBank Accession No. AAA88820, Feb. 20, 1998.
GenBank Accession No. AAC41260, Mar. 6, 1998.
GenBank Accession No. AF036325, Mar. 7, 1998.
GenBank Accession No. U35632, Feb. 21, 1996.
Gerbal-Chaloin et al. "The WNT/β-catenin pathway is a transcriptional regulator of CYP2E1, CYP1A2, and aryl hydrocarbon receptor gene expression in primary human hepatocytes" Molecular pharmacology. Dec. 1, 2014;86(6):624-34.
Coke et al. "Exendin-4 is a High Potency Agonist and Truncated Exendin-(9-39)-amide an Antagonist at the Glucagon-Like Peptide 1-(7-36)-amide Receptor of Insulin-Secreting Beta- Cells," J. Biol, Chem. 268.26(1993):19650-19655.
Goldspiel et al. "Human Gene Therapy." Clin. Pharm. 12(1993):488-505.
Goodson, Ch. 6 "Dental Applications" In: Medical Applications of Controlled Release 1984, pp. 115-138, CRC Press, Boca Raton, Fla.
Gottesman. "Minimizing Proteolysis in *Escherichia coii*: Genetic Solutions," Meth. Enzymol. 185(1990): 119-129.
Gradwohl et al. "neurogenin3 is required for the development of the four endocrine cell lineages of the pancreas", Proc Natl Acad Sci U S A. Feb. 15, 2000;97(4):1607-11.
Graf T. "Historical origins of transdifferentiation and reprogramming" Cell stem cell. Dec. 2, 2011;9(6):504-16.
Gross et al. "increased Susceptibility of Islets From Diabetes-Prone psammomys ovesusto the Deleterious Effects of Chronic Glucose Exposure." Endocr. 137.12(1996):5610-5615.
Guo et al. "Combined transfection of the three transcriptional factors, PDX-1, NeuroD1, and MafA, causes differentiation of bone marrow mesenchymal stem cells into insulin-producing cells", Exp Diabetes Res. 2012;2012:672013.
Ham et al. "Generation of functional insulin-producing cells from neonatal porcine liver derived cells by PDX1/VP16, BETA2/NeuroD and MafA" PloS one. Nov. 15, 2013;8(11):e79076.
Hamad et al. "Distinct Requirements for Ras Oncogenesis in Human Versus Mouse Ceils." Genes Dev. 18.16(2002):2045-2057.
Hamaguchi et al. "Comparison of Cytokine Effects on Mouse Pancreatic Alpha-Cell and Beta- Cell Lines," D/afcefes.39.4(1990):415-425.
Hanna et al. "Direct reprogramming of terminally differentiated mature B lymphocytes to pluripotency", Cell. Apr. 18, 2008;133(2):250-64.
He et al. "A simplified system for generating recombinant adenoviruses", Proc Natl Acad Sci U S A. Mar. 3, 1998;95(5):2509-14.
Horb et al. "Experimental Conversion of Liver to Pancreas," Curr. Biol. 13 105-115, 2013.
Howard et al. "Intracerebral drug delivery in rats with lesion-induced memory deficits" J, Neunosurq. 71(1989):105-112.
Hsu et al. "Molecular Cloning of a Novel Splice Variant of the a Subunit of the Mammalian G0 Protein," J. Bio!. Chem. 265. 19(1990):11220-11226:.
Ieda et al. "Direct reprogramming of fibroblasts into functional cardiomyocytes by defined factors", Cell. Aug. 6, 2010;142(3):375-86.
International Search Report for PCT Application No. PCTIB2014002164, dated May 27, 2015.
Invitrogen pcDNA1.1 vector (online). Tools.invtrogen.com/conterit/sfs/vectors/pcdna1.1.pdf,. Retrieved Juiv 3. 2.008.
Iwasaki et al. "The order of expression of transcription factors directs hierarchical specification of hematopoietic lineages", Genes Dev. Nov. 1, 2006;20(21):3010-21.
Joliot et al. "Antennapedia Homeobox Peptide Regulates Neural Morphogenesis." PNAS. 88(1991 ):1864-1868.
Jonsson et al. "insulin-Promoter-Factor 1 is Required for Pancreas Development in Mice." Nature. 371 (1994):606-609.
Kahn "Converting Hepatocytes to β-cells - A New Approach for Diabetes?" Nat, Med, 8(2000):505-506.
Kahn et al. "Islet amyloid: a long-recognized but underappreciated pathological feature of type 2 diabetes",1999 Diabetes, 48:241-253.
Kajimoto et al. "Suppression of Transcription Factor PDX-1/IPF1/STF-1 Causes No Decrease in Insulin mRNA in MIN6," J. Clin, Invest. 100(1997):1840-1846.
Kaneto et al. "A crucial role of MafA as a novel therapeutic target for diabetes", J Biol Chem. Apr. 15, 2005;280(15):15047-52.
Kaneto et al. "PDX-1/VP16 fusion protein, together with NeuroD or Ngn3, markedly induces insulin gene transcription and ameliorates glucose tolerance", Diabetes. Apr. 2005;54(4):1009-22.
Kataoka et al. "MafA is a glucose-regulated and pancreatic beta-cell-specific transcriptional activator for the insulin gene", J Biol Chem. Dec. 20, 2002;277(51):49903-10.
Kaufman et al. "Translational Efficiency of Polycistronic mRNAs and Their Utilization to Express Heterologous Genes in Mammalian Ceils," EMBO J. 6.1(1987):187-193.
Kessell et al. "Murine Developmental Control Gene," Science. 249(1990);374-379.
Khaoustov et al. "Induction of three-dimensional assembly of human liver cells by simulated microgravity" In Vitro Cellular & Developmental Biology-Animal. Oct. 1, 1999;35(9):501-9.
Koizumi et al. "Hepatic regeneration and enforced PDX-1 expression accelerate transdifferentiation in liver", Surgery. Aug. 2004;136(2):449-57.
Kojima et al. "NeuroD-betacellulin gene therapy induces islet neogenesis in the liver and reverses diabetes in mice", Nat Med. May 2003;9(5):596-603.
Kojima et al. "Combined Expression of Pancreatic Duodenal Homeobox 1 and Islet Factor 1 Induces Immature Enterocytes 40 Produce Insulin." Diabetes, 51,5(2002):1398-1408.
Koller et al. "inactivating the beta 2-Microglobulin Locus in Mouse Embryonic Stem Cells by Homologous Recombinant." PNAS. 88(1989):8932-8935.
Koya et al, "Reversal of Streptozotocin-Induced Diabetes in Mice by Cellular Transduction with Recombinant Pancreatic Transcrip-

(56) References Cited

OTHER PUBLICATIONS tion Factor Pancreatic Duodenal Homeobox-1: A Novel Protein Transduction Domain-Based Therapy." Diabetes. 57(2008):757-769.
Krause et al. "Cultured hepatocytes adopt progenitor characteristics and display bipotent capacity to repopulate the liver" Cell transplantation. Jun. 26, 2014;23(7):805-17.
Kroon et al. "Pancreatic endoderm derived from human embryonic stem cells generates glucose-responsive insulin-secreting cells in vivo", Nat Biotechnol. Apr. 2008;26(4):443-52. doi: 10.1038/nbt1393.
Kurjan et al. "Structure of a Yeast Pheromone Gene (MFa): A Putative a-Factor Precursor Contains Four Tandem Copies of Mature a-Factor," Cell. 30(1982);933-943.
Li et al. "in Vitro Transdifferentiation of Hepatoma Cells into Functional Pancreatic Cells." Mech. Dev. 122(2005):835-847.
Lin et al. "Expression of T Cell Antigen Receptor Heterodimer in a Lipid-Linked Form." Science. 249.4969(1990):677-679.
Loeffler et al. "Gene Transfer Into Primary and Established Mammalian Ceil Lines With Lipopolyamine-Coated DNA." Meth. Enzymol. 217(1993):599-618.
Lu et al. "Hepatic progenitor cells of biliary origin with liver repopulation capacity" Nature cell biology. Aug. 1, 2015;17(8):971-83.
Luckow et al, "High Level Expression of Nonf used Foreign Genes with Authographa californica Nuclear Polyhedrosis Virus Expression Vectors," Virol. 170(1989):31-39.
Marshak et al. "Purification of the beta-Cell Glucose-Sensitive Factor That Transactivates the Insulin Gene Differentially in Normal and Transformed Islet Ceils." PNAS. 93.26(1996):15057-15062.
Maxcyte GT® Flow Transfection System at http://www.maxcyte.com/applications/mRNA-CAR.php, 2015.
Meivar-Levy et al. "New organs from our own tissues: liver-to-pancreas transdifferentiation", Trends Endocrinol Metab. Dec. 2003;14(10):460-6.
Meivar-Levy et al. "Regenerative medicine: using liver to generate pancreas for treating diabetes", Isr Med Assoc J. Jun. 2006;8(6):430-4.
Meivar-Levy et al. "Adult cell fate reprogramming: converting liver to pancreas", Methods Mol Biol. 2010;636:251-83.
Meivar-Levy et al. "Human liver cells expressing albumin and mesenchymal characteristics give rise to insulin-producing cells", J Transplant. 2011;2011:252387.
Meivar-Levy et al. "Pancreatic and duodenal homeobox gene 1 induces hepatic dedifferentiation by suppressing the expression of CCAAT/enhancer-binding protein beta", Hepatology. Sep. 2007;46(3):898-905.
Milewski et al. "Conservation of PDX-a Structure, Function, and Expression In Zebrafish." Endocr. 139.3(1998): 1440-1449.
Miller et al. "IDX-1: A New Homeodomain Transcription Factor Expressed in Rat Pancreatic Islets and Duodenum That Transactivates the Somatostatin Gene." EMBO J. 13.5(1994): 1145.
Mitanchez et al. "Regulated Expression of Mature Human Insulin in the Liver of Transgenic Mice." FEBS Letts. 421.3(1998):285-289.
Muniappan et al. "Induction of insulin secretion in engineered liver cells by nitric oxide" BMC physiology. Oct. 17, 2007;7(1):11.
Munoz et al. "Conventional pluripotency markers are unspecific for bovine embryonic-derived cell-lines", (2008, Theriogenology, vol. 69, pp. 1159-1164).
Murtaugh et al. "Genes, signals, and lineages in pancreas development", Annu Rev Cell Dev Biol. 2003;19:71-89.
Muzzin et al. "Hepatic Insulin Gene Expression as Treatment for Type 1 Diabetes Meiiitus in Fiats." 1997, Moi. Endocr. 11(1 Q97):833-837.
Nakajima-Nagata et al. "PDX-1 Enables Insulin Secretion by Regulating Synaptotagmin 1 Gene Expression." Biochem. Biophvs. Res. Comm. 318(2004):631-635.

Nicolau et al. "In vivo Expression of Rat Insulin After intravenous Administration of the Liposome-Entrapped Gene for Rat Insulin 1." PNAS, 80,4(1983):1068-1072.
Nir et al, "How to Make Pancreatic j3 Cells—Prospects for Cell Therapy in Diabetes." Cure Opin. Biotech. 16(2005):524-529.
Nishimura et al. "Expression of MafA in pancreatic progenitors is detrimental for pancreatic development", Dev Biol. Sep. 1, 2009;333(1):108-20.
Noguchi et al. "Mechanism of PDX-1 Protein Transduction." Biochem. Biophys. Res. Comm. 332(2005):68-74.
Noguchi et al. "PDX-1 Protein Containing Its Own Antennapedia-Like Protein Transduction Domain Can Transduce Pancreatic Duct and Islet Cells," Diabetes. 52(2003): 1732-1737.
Novolin R. drugs.com retrieved Apr. 10, 2010. http://www.drugs.com/pro.novolin-r.html.
Offield et al. "PDX-1 is Required for Pancreatic Outgrowth and Differentiation of the Rostral Duodenum." Dev. 122(1996)1983-995.
Ohneda et al. "The Homeodomain of PDX-1 Mediates Multiple Protein-Protein Interactions in the Formation of a Transcriptional Activation Complex on the Insulin Promoter." Mol. Ceil. Biol. 20(2000):900-911.
Okitsu et al. "Transplantation of reversibly immortalized insulin-secreting human hepatocytes controls diabetes in pancreatectomized pigs", Diabetes. Jan. 2004;53(1):105-12.
Olbrot et al. "Identification of beta-cell-specific insulin gene transcription factor RIPE3b1 as mammalian M", Proc Natl Acad Sci U S A. May 14, 2002;99(10):6737-42.
Otonkoski et al, "Stem Celis in the Treatment of Diabetes." Ann. Med. 37,7(2005):513-52.
Ozcan et al. "Functional Expression and Analysis of the Pancreatic Transcription Factor PDX- 8 1 in Yeast." Biochem. Biophys. Res. Comm. 295(2002):724-729.
Pang et al. "Induction of human neuronal cells by defined transcription factors", Nature. May 26, 2011;476(7359):220-3.
Paris et al. "Equine embryos and embryonic stem cells: defining reliable markers of pluripotency", Theriogenology. Sep. 1, 2010;74(4):516-24.
Patel et al. Therapeutic potential of mesenchymal stem cells in regenerative medicine. Stem cells international. Mar. 19, 2013;2013, pp. 1-15.
Peers et al. "Insulin Expression in Pancreatic Islet Cells Relies on Cooperative Interactions s Between the Helix Loop Helix Factor E47 and the Homeobox Factor STF-1." Moi. :! Endocr. 8 (' 1994): 17981806.
Pinkert et ai. "An Albumin Enhancer Located 10 kb Upstream Functions Along With its Promoter to Direct Efficient, Liver-Specific Expression in Transgenic Mice," Genes Dev. 1(1987):268-278.
Queen et ai. "immunoglobulin Gene Transcription is Activated by Downstream Sequence Elements." Cell. 33(1983):741-748.
Reniers et al. "Industrialization of a Cell-based Autologous Therapy Targeting Diabetes: Industrialization of a Liver Cell Proliferation Process from Petri Dish to the Xpansion® Multiplate Bioreactor", Pall.com. Xpansion Multiplate Bioreactor System. 2015: http://www.pall.com/main/biopharmaceuticals/product.page?lid=hw7uq21i. Accessed Aug. 13, 2015.
Rheinwald et al. "Epidermal Growth Factor and the Multiplication of Cultured Human Epidermal Keratinocites." Nature. 285(1977):421-424.
Rojas et al (The Islets of Langerhans, Advances in Experimental Medicine and Biology, vol. 654, 2010, pp. 59-75).
Ross "Protein Power: Researchers Trigger Insulin Production in Diabetic Mice." University of Florida News. Jan. 18, 2008 (http://news.etl.edu/2008/01/08/pdx1/-).
Sakai et al. "Rapid fabricating technique for multi-layered human hepafic cell sheets by forceful contraction of the fibroblast monolayer" PloS one. Jul. 26, 2013;8(7):e70970.
Sakurai et al. "Comparison of gene expression efficiency and innate immune response induced by Ad vector and lipoplex", 2007, Journal of controlled release 117: 430-437.

(56) References Cited

OTHER PUBLICATIONS

Salomaa et al, "Non-Insulin-Dependent Diabetes Mellitus and Fasting Glucose and Insulin Concentrations are Associated With Arterial Stiffness Indexes: The ARIC Study." Circ. 91 (1995):1432-1443.
Sapir et al. "Cell-replacement therapy for diabetes: Generating functional insulin-producing tissue from adult human liver cells", Proc Natl Acad Sci U S A. May 31, 2005;102(22):7964-9.
Saudek et al. "A preliminary trial of the programmable implantable medication system for insulin delivery", N Engl J Med. Aug. 31, 1989;321(9):574-9.
Schmidt et al. The cytomegalovirus enhancer: a pan-active control element in transgenic mice. Molecular and Cellular Biology. Aug. 1, 1990;10(8):4406-11.
Schultz et al. "Expression and Secretion in Yeast of a 400-kDa Envelope Glycoprotein Derived from Epstein-Barr Virus." Gene. 54(1987): 113-123.
Seed. "An LFA-3 cDNA Encodes a Phospholipid-Linked Membrane Protein Homologous to its Receptor CD2," Nature. 329(1987):840-842.
Seijffers et al. "Increase in PDX-1 levels suppresses insulin gene expression in RIN 1046-38 cells", Endocrinology. Jul. 1999;140(7):3311-7.
Serup et ai. induction of insulin and islet Amyloid Polypeptide Production in Pancreatic Islet Qlufeagonoma Cells fey Insulin Promoter Factor 1PNAS. 9015-9020, 1996.
Shamblott et al. "Ceil Theraoies for Type 1 Diabetes Mellitus." Exp. Opin. 4.3(2004);269-277.
Shanmukhappa et al. "Hepatic to pancreatic switch defines a role for hemostatic factors in cellular plasticity in mice" Proceedings of the National Academy of Sciences of the United States of America. Jul. 19, 2005;102(29):10182-7.
Sheyn et al. "Genetically modified cells in regenerative medicine and tissue engineering", Adv Drug Deliv Rev. Jun. 15, 2010;62(7-8):683-98.
Shternhall et al. "Ectopic PDX-1 expression in liver ameliorates type 1 diabetes", J Autoimmun. Mar.-May 2007;28(2-3):134-42.
Slack et al. "Transdifferentiation and metaplasia—switching cell types", Curr Opin Genet Dev. Oct. 2001;11(5):581-6.
Smith et al. "Production of Human Beta interferon in insect Cells Infected with a Baculovirus Expression Vector." Mol. Cell. Biol 3,12(1983):2156-2165.
Smith et al. "Single-Step Purification of Polypeptides Expressed in *Escherichia coli*, as Fusion With Glutathione S-Transferase." Gene. 67(1988):31-40.
Song et al. "Islet cell differentiation in liver by combinatorial expression of transcription factors neurogenin-3, BETA2, and RIPE3b1", Biochem Biophys Res Commun. Mar. 9, 2007;354(2):334-9.
Stemple et al. "Isolation of a Stem Cell for Neurons and Gila From the Mammalian Neural Crest." Cell. 71(1992):973-985.
Stoffers et al. "Homeodomain protein IDX-1: a master regulator of pancreas development and insulin gene expression", Trends Endocrinol Metab. May-Jun. 1997;8(4):145-51.
Studier et al. in gene expression technology methods in enzymology 185 academic press san diego ca pp. 60-89 1990.
Supplementary European Search Report for European Application No. 14818254.6 dated Feb. 20, 2017.
Szabo et al. "Direct conversion of human fibroblasts to multilineage blood progenitors", Nature. Nov. 25, 2010;468(7323):521-6.
Takahashi et al. "Induction of Pluripotent Stem Cells from Mouse Embryonic and Adult Fibroblast Cultures by Defined Factors", Cell 126, 663-676, Aug. 25, 2006.
Takebe et al. "SRa Promoter: An Efficient and Versatile Mammalian cDNA Expression System Composed of the Simian Virus 40 Early Promoter and R-U5 Segment of Human T-Cell Leukemia Virus Type 1 Long Terminal Repeat." Mol. Ceil. Biol. 8.1(1988):466-472.
Tang et al. "Role of Pax4 in Pdx1-VP16-mediated liver-to-endocrine pancreas transdifferentiation", Lab Invest. Aug. 2006;86(8):829-41.
Thowfeequ et al. "Transdifferentiation in developmental biology, disease, and in therapy", Dev Dyn. Dec. 2007;236(12):3208-17.

Thowfeequ et al, "Reprogramming of liver to pancreas" Stem Cells in Regenerative Medicine, 2009:407-18.
Torre et al. "Transcription dynamics in a physiological process: β-catenin signaling directs liver metabolic zonation" The international journal of biochemistry & cell biology. Feb. 28, 2011;43(2):271-8.
Treacy et al. "Adenoviral transduction of mesenchymal stem cells: in vitro responses and in vivo immune responses after cell transplantation", PLoS One. 2012;7(8):e42662.
Trehin et al. "Chances and Pitfalls of Cell Penetrating Peptides for Cellular Drug Delivery." Eur. J. Pharm. Biopharm. 58(2004):209-223.
Tur-Kaspa et al. Use of electroporation to introduce biologically active foreign genes into primary rat hepatocytes. Molecular and cellular biology. Feb. 1, 1986;6(2):716-8.
Varda-Bloom et al. "Tissue-specific gene therapy directed to tumor angiogenesis", Gene Ther. Jun. 2001;8(11):819-27.
Verma et al, "Gene Therapy-Promises, Problems and Prospects," Nature. 389(1997):239-242.
Vieau et al. Mouse insulinoma beta TC3 cells express prodynorphin messenger ribonucleic acid and derived peptides: a unique cellular model for the study of prodynorphin biosynthesis and processing. Endocrinology. Mar. 1995;136(3):1187-96.
Vierbuchen et al. "Direct conversion of fibroblasts to functional neurons by defined factors", Nature. Feb. 25, 2010;463(7284):1035-41.
Wada et al. "Codon Usage Tabulated From the GenBank Genetic Sequence Data." Nucleic Acids Res. May 11, 1992;20 Suppl:2111-8.
Wang et al. "Glucagon-Like Peptide-1 Regulates the Beta Cell Transcription Factor, PDX-1, in Insulinoma Ceils." Endocr. 140. 10(1999):4904-4907.
Wang et al. "Adenovirus transduction is required for the correction of diabetes using Pdx-1 or Neurogenin-3 in the liver", Mol Ther. Feb. 2007;15(2):255-63.
Wang et al. "Pdx1 level defines pancreatic gene expression pattern and cell lineage differentiation", J Biol Chem. Jul. 6, 2001;276(27):25279-86.
Wang et al. "Stoichiometry of Gata4, Mef2c, and Tbx5 Influences the Efficiency and Quality of Induced Cardiac Myocyte Reprogramming Novelty and Significance" Circulation research. Jan. 16, 2015;116(2):237-44.
Watada et al. "Involvement of the Homeodomain-Containing Transcription Factor PDX-1 in Islet Amyloid Polypeptide Gene Transcription", Biochemical and Biophysical Research Communications 229, 746-751, 1996.
Weintraub et al. Anti-Sense RNA as a Molecular Tool for Genetic Analysis. Reviews—Trends in Genetics. 1,1(1985) :22-25.
Winoto et ai. "A Novel, Inducible and T Cell-Specific Enhancer Located at the 3' End of the T Cell Receptor a Locus," EMBO J. 8.3(1989):729-733.
Wu et al. "Receptor-mediated in vitro gene transformation by a soluble DNA carrier system", J Biol Chem. Apr. 5, 1987;262(10):4429-32.
Xu et al "Mesenchymal stem cells differentially mediate regulatory T cells and conventional effector T cells to protect fully allogeneic islet grafts in mice", Diabetologia. Apr. 2012; 55(4):1091-102.
Yamada et al. "in Vitro Transdifferentiation of HepG2 Cells to Pancreatic-Like Cells by CCI4, d-Galactosamine, and ZnC!2." Endocr. J. 53.6(2006):789-795.
Yamanaka et al. "Induction of pluripotent stem cells from mouse fibroblasts by four transcription factors", Cell Prolif. Feb. 2008;41 Suppl 1:51-6.
Yang et ai. "in vitro Trans-Differentiation of Adult Hepatic Stem Cells Into Pancreatic Endocrine- Hormone-Producing Cells." PNAS. 99.12(2002):8078-8083.
Yechoor et al. "Minireview: beta-cell replacement therapy for diabetes in the 21st century: manipulation of cell fate by directed differentiation", Mol Endocrinol. Aug. 2010;24(8):1501-11.
Yeung et al. "Human mesenchymal stem cells protect human islets from pro-inflammatory cytokines", PLoS One. 2012;7(5):e38189.

(56) References Cited

OTHER PUBLICATIONS

Zalzman et al. "Differentiation of human liver-derived, insulin-producing cells toward the β-cell phenotype" Diabetes. Sep. 1, 2005;54(9):2568-75.
Zhou et al. "In vivo reprogramming of adult pancreatic exocrine cells to beta-cells", Nature. Oct. 2, 2008;455(7213):627-32.
Alves Cardoso et al. "Gelation and biocompatibiiity of injectable Alginate—Calcium phosphate gels for bone regeneration" Journal of Biomedical Materials Research Part A, Mar. 2014;102(3):808-17.
Amann et al. "Tightly regulated tac promoter vectors useful for the expression of unfused and fused proteins in *Escherichia coli*" Gene. Sep. 30, 1988;69(2):301-15.
Ferber et al. "Transdifferentiation and its implementation" in Autologous Cell Replacement Therapy for Diabetes; May 29, 2014, pp. 1-35.
Freeman et al. "The influence of the sequential delivery of angiogenic factors from affinity-binding alginate scaffolds on vascularization" Biomaterials. Apr. 1, 2009:30(11):2122-31.
Freeman et al, "The effect of sulfation of alginate hydrogels on the specific binding and controlled release of heparin-binding proteins" Biomaterials. Aug. 1, 2008;29(22)3260-8.
Gen Bank Accession No. NM_006193.2, Sep. 6, 2014.
Gen Bank Accession No. AAD02289 . Mar. 10, 2010.
Gen Bank Accession No, NM_201589.3, Sep. 6, 2014.
Gen Bank Accession No. NP_963883.2, Sep. 6, 2014.
Gen Bank Accession No. N _020999.3; Sep. 6, 2014.
Gen Bank Accession No. NP_066279.2, Sep. 6, 2014.
Gen Bank Accession No. NM_002500.4, Sep. 6, 2014.
Gen Bank Accession No, NP__002491.2, Sep. 6, 2014,.
Gen Bank Accession No. NM_000311 .3, Sep. 6, 2014.
Gen Bank Accession No. NP_000337,1, Sep. 6, 2014.
Gen Bank Accession No. X02812.1, Feb. 2, 2011.
Gen Bank Accession No. AJ009860.1, Oct. 19, 2006.
Grapin-.Botton A. "Three-dimensional pancreas organogenesis models. Diabetes" Obesity and Metabolism. Sep. 2016;18:33-40.
Greenberger et al. "Corticosteroid suppression of VEGF-A in infantile hemangioma-derived stern cells" New England Journal of Medicine, Mar. 18, 2010;362(11):1005-13.
Ito et al. "Mesenchymal stem cell and islet co-transplantation promotes graft revascularization and function" Transplantation. Jun. 27, 2010;89(12):1438-45.
Iwasaki et al. "The order of expression of transcription factors directs hierarchical specification of hematopoletic lineages" Genes & development. Nov. 1, 2006;20(21):3010-21.
Kang et al. "Bioengineered human vascular networks transplanted into secondary mice reconnect with the host vasculature and re-establish perfusion" Blood, The Journal of the American Society of Hematology. Dec. 15, 2011;118(25):6718-21.
Lima et al. "Generation of functional beta-like cells from human exocrine pancreas" PLoS One. 2016;11(5).

Lin et al. "Human endothelial colony-forming cells serve as trophic mediators for mesenchymal stem cell engraftment via paracrine signaling" Proceedings of the National Academy of Sciences. Jul. 15, 2014;111(28)1 0137-42.
Mauda-Havakuk et al. "Ectopic PDX-1 expression directly reprograms human keratinocytes along pancreatic insulin-producing cells fate" PLoS One. 2011;6(10).
Melero-Martin et al. "Engineering robust and functional vascular networks in vivo with human adult and cord blood-derived progenitor cells" Circulation research. Jul. 18, 2008;103(2)1 94-202.
Minami et al, "Lineage tracing and characterization of insulin-secreting cells generated from adult pancreatic acinar cells" Proceedings of the National Academy of Sciences. Oct. 18, 2005;102(42)15116-21.
Nasr et al. "Co-transplantation of autologous MSCs delays islet allograft rejection and generates a local imimunoprivileged site", Acta Diabetol, Oct. 2015;52(5):917-27.
Orr et al. "TGF-β affinity-bound to a macroporous alginate scaffold generates local and peripheral immunotolerant responses and improves allocell transplantation" Acta biomaterialia. Nov. 1, 2016;45:196-209.
Qing-Song et al. "Combined transfection of the three transcriptional factors, PDX-1, NeuroD1, and MafA, causes differentiation of bone marrow mesenchymal stem cells into insulin-producing cells" Experimental diabetes research. Jun. 19, 2012:2012.
Re'em et al. "Simultaneous regeneration of articular cartilage and subchondral bone induced by spatially presented TGF-beta and BMP-4 in a bilayer affinity binding system" Acta biomaterialia. Sep. 1, 2012;8(9):3283-93.
Shapiro et al. "Novel alginate sponges for cell culture and transplantation" Biomaterials. Apr. 1, 1997;18(8)583-90.
Stoffel et al. "Localization of human homeodomain transcription factor insulin promoter factor 1 (IPF1) to chromosome band 13q12. 1" Genomics (San Diego, Calif.). 1995;28(1):125-6.
Stoffers et al, "Homeodomain protein IDX-1: a master regulator of pancreas development and insulin gene expression" Trends in Endocrinology & Metabolism. May 1, 1997;8(4):145-51.
Ungrin et al. "Reproducible, ultra high-throughput formation of multicellular organization from single cell suspension-derived human embryonic stem cell aggregates" PloS one. 2008;3(2).
Van Der Meulen et al. "Maturation of stem cell-derived beta-cells guided by the expression of urocortin 3" The review of diabetic studies: RDS. 2014:11(1)115.
Young et al, "β-catenin/Tcf activation partially mimics the transforming activity of Wnt-1 in Rat-1 fibroblasts" Differentiation. Oct. 1, 2003;71(8):477-85.
Zhu et al. "Human pancreatic beta-like cells converted from fibroblasts" Nature communications. Jan. 6, 2016;7(1):1-3.

\* cited by examiner

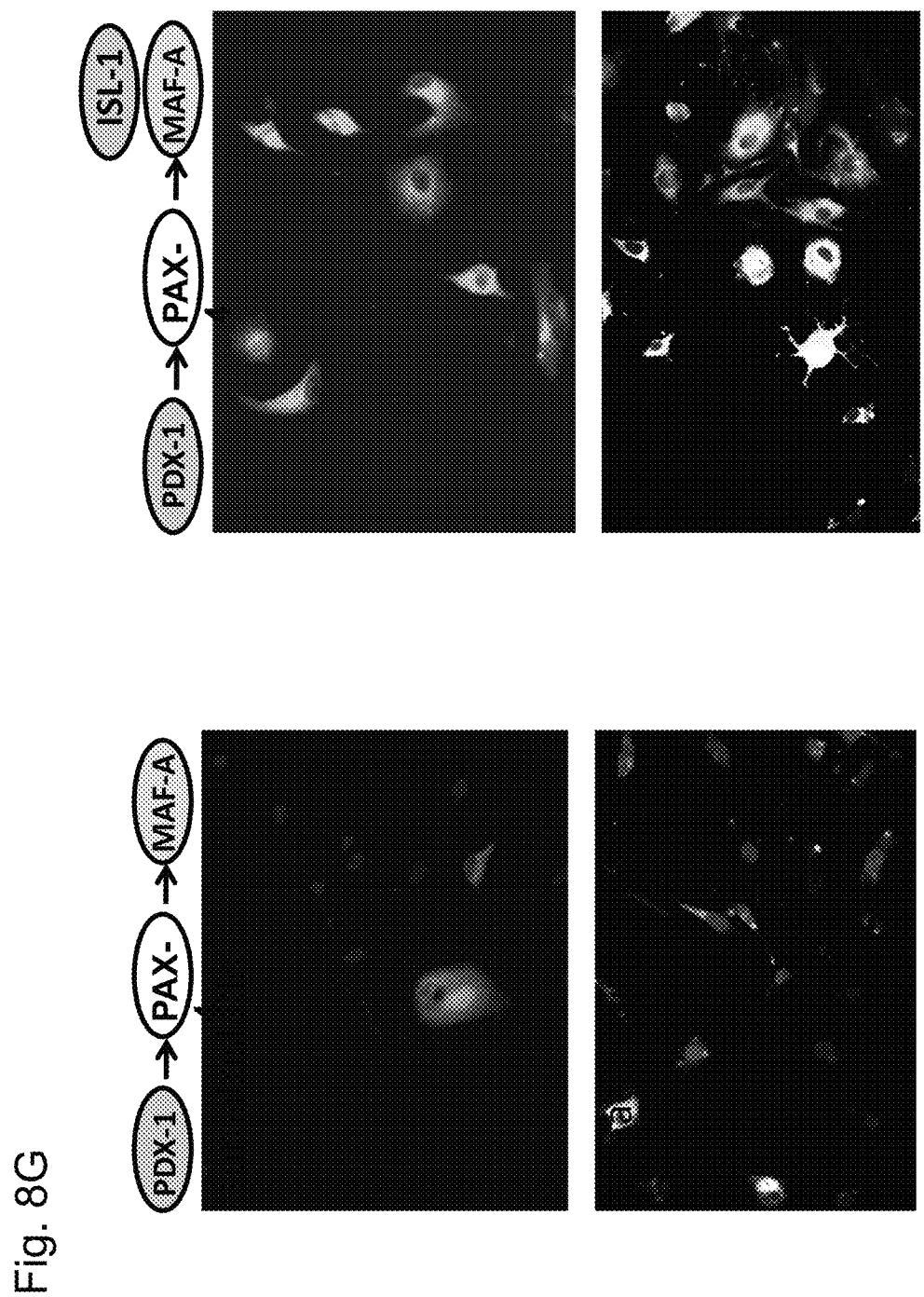

CELL POPULATIONS, METHODS OF TRANSDIFFERENTIATION AND METHODS OF USE THEREOF

CROSS REFERENCE TO RELATED APPLICATIONS

This application is a divisional of U.S. patent application Ser. No. 14/897,262 filed Dec. 10, 2015, and granted as U.S. Pat. No. 9,982,236 on May 29, 2018, which is a National Phase Application of PCT International Application No. PCT/IB2014/002164, International Filing Date Jun. 13, 2014, which claims priority to and benefit of U.S. Provisional Application Ser. No. 61/834,759 filed on Jun. 13, 2013 and U.S. Provisional Application Ser. No. 61/834,767 filed on Jun. 13, 2013, the contents of which are herein incorporated by reference in their entireties.

FIELD OF THE INVENTION

The invention generally relates cell populations that are predisposed to transdifferentiation and method for to the production of cells having a mature pancreatic beta cell phenotype and function.

BACKGROUND OF THE INVENTION

The beta-cells of the islets of Langerhans in the pancreas secrete insulin in response to factors such as amino acids, glyceraldehyde, free fatty acids, and, most prominently, glucose. The capacity of normal islet beta-cells to sense a rise in blood glucose concentration and to respond to elevated levels of glucose by secreting insulin is critical to the control of blood glucose levels. Increased insulin secretion in response to a glucose load prevents hyperglycemia in normal individuals by stimulating glucose uptake into peripheral tissues, particularly muscle and adipose tissue.

Individuals in whom islet beta-cells function is impaired suffer from diabetes. Insulin-dependent diabetes mellitus, or IDDM (also known as Juvenile-onset or Type I diabetes), represents approximately 10% of all human diabetes. IDDM is distinct from non-insulin dependent diabetes (NIDDM) in that only IDDM involves specific destruction of the insulin producing beta-cells of the islets of Langerhans. The destruction of beta-cells in IDDM appears to be a result of specific autoimmune attack, in which the patient's own immune system recognizes and destroys the beta-cells, but not the surrounding alpha-cells (glucagon producing) or delta-cells (somatostatin producing) that comprise the islet.

Treatment options for IDDM are centered on self-injection of insulin—an inconvenient and imprecise solution- and thus the development of new therapeutic strategies is highly desirable. The possibility of islet or pancreas fragment transplantation has been investigated as a means for permanent insulin replacement (Lacy, 1995; Vajkoczy et al., 1995). Current methodologies use either cadaverous material or porcine islets as transplant substrates (Korbutt et al., 1997). However, significant problems to overcome are the low availability of donor tissue, the variability and low yield of islets obtained via dissociation, and the enzymatic and physical damage that may occur as a result of the isolation process (reviewed by Secchi et al., 1997; Sutherland et al., 1998). In addition are issues of immune rejection and current concerns with xenotransplantation using porcine islets.

It is clear that there remains a critical need to establish alternatives to the treatment of diabetes by self-injection of insulin. While stem cell research has shown promise in this regard, there has not been great success. There is a need for improved procedures for isolating, culturing, and transdifferentiating non-pancreatic cells to be used in the treatment of diabetes.

SUMMARY OF THE INVENTION

The present invention provides a method of producing a population of cells having a mature pancreatic beta cell phenotype and function by contacting adult mammalian non-pancreatic cells with a pancreatic and duodenal homeobox (PDX-1) polypeptide, or a nucleic acid encoding a pancreatic and duodenal homeobox (PDX-1) polypeptide under conditions to allow uptake of the polypeptide, or nucleic acid at a first time period; further contacting the cells with a Pax-4 polypeptide, a NeuroD1 polypeptide, or nucleic acid encoding a Pax-4 polypeptide, or nucleic acid encoding a NeuroD1 polypeptide under conditions to allow uptake of the polypeptide or nucleic acid at a second time period; and further contacting the cells of step with a MafA polypeptide or a nucleic acid encoding a MafA polypeptide under conditions to allow uptake of the nucleic acid at a third time period. The second time period is at least 24 hours after the first time period. The third time period is at least 24 hours after the second time period. In some embodiments the first, second and third period of time are the same time Alternatively the invention provides a method of producing a population of cells having a mature pancreatic beta cell phenotype and function by contacting adult mammalian non-pancreatic cells with a pancreatic and duodenal homeobox (PDX-1) polypeptide or a nucleic acid encoding a pancreatic and duodenal homeobox (PDX-1) polypeptide and a second pancreatic transcription factor, under conditions to allow uptake of the PDX-1 polypeptide, or nucleic acid and the second pancreatic transcription factor at a first time period; and further contacting the cells with a MafA polypeptide, or a nucleic acid encoding a MafA polypeptide under conditions to allow uptake of the nucleic acid at a second time period. In some embodiments the second period of time is at least 2, 3, 4, 5, 6 or 7 days after the first period of time. The second pancreatic transcription factor is for example, NeuroD1, Pax-4, or Ngn3.

The nucleic acid is a ribonucleic acid or a deoxyribonucleic acid.

Optionally, the cells are further contacted with a nucleic acid encoding Sox-9 polypeptide or Sox-9 polypeptide under conditions to allow uptake of the nucleic acid or polypeptide.

The cells are bone marrow, muscle, spleen, kidney, blood, skin, pancreas, and liver cells. The cells are contacted in vivo. The cells are contacted in vitro. The population of cells produced by the methods of the present invention includes at least 0.5 billion cells. In some embodiments, the cells are expanded in culture prior to the contacting with the polypeptides or nucleic acids.

Also included in the invention are methods of treating a degenerative pancreatic disorder by administering to a subject in need thereof: a composition comprising a PDX-1 polypeptide or a nucleic acid encoding a PDX-1 polypeptide at a first time period; a composition comprising a Pax-4 polypeptide, a NeuroD1 polypeptide, a nucleic acid encoding a Pax-4 polypeptide or a nucleic acid encoding a NeuroD1 polypeptide at a second time period; and a composition comprising MafA polypeptide or a nucleic acid encoding a MafA polypeptide at a third time period. The second time period is at least 24 hours after the first time period. The third time period is at least 24 hours after the second time period. In some embodiments the first, second and third period of time are the same time.

Further provided by the invention are methods of treating a degenerative pancreatic disorder by administering to a subject in need thereof a composition comprising a PDX-1 polypeptide a nucleic acid encoding a PDX-1 polypeptide and a second pancreatic transcription factor at a first time period; and a composition comprising a MafA polypeptide or a nucleic acid encoding a MafA polypeptide at a second time period. In some embodiments the second period of time is at least 2, 3, 4, 5, 6 or 7 days after the first period of time. The second pancreatic transcription factor is for example, NeuroD1, Pax-4, or Ngn3.

The nucleic acid is a ribonucleic acid or a deoxyribonucleic acid.

Optionally, the subject is further administered a nucleic acid encoding Sox-9 polypeptide or Sox-9 polypeptide under conditions to allow uptake of the nucleic acid or polypeptide.

Also included in the invention are methods of treating a degenerative pancreatic disorder by administering to a subject in need thereof the population of cells produced by the methods of the invention The degenerative pancreatic disorder is diabetes such as is Type I, Type II or gestational diabetes. Alternatively, the degenerative pancreatic disorder is pancreatic cancer or pancreatitis.

The present invention further provides an expression vector including a nucleic acid encoding PDX-1 polypeptide and a nucleic acid encoding a second transcription factor or use in any of the methods for producing a population of cells having a mature pancreatic beta cell phenotype or methods for treating a degenerative pancreatic disorder. The second transcription is, for example, NeuroD1, Pax-4, Ngn3, or Sox-9.

Further included in the invention is an enriched population of human cells capable of activating the glutamine synthetase response element (GSRE). At least 5%, 10%, 15%, 20%, 25%, 30% or more of the cells in the population are capable of activating glutamine synthetase response element (GSRE). The cells are endothelial cells, epithelial cells, mesenchymal cells, fibroblasts, or liver cells. In some aspects the liver cells are derived from the pericentral liver. Preferably, the cells have active Wnt signaling. At least 5%, 10%, 15%, 20%, 25%, 30% or more of the cells in the population produce insulin or secrete c-peptide when the cells are treated to ectopically express a pancreatic transcription factor, such as Pdx-1, Pax-4, MafA, NeuroD1, or a combination thereof. Optionally, the population of cells express at least one of Wnt3a; decreased levels of DKK1 or DKK3; decreased levels of APC; increased activated beta-catenin levels; or STAT5 binding elements (cis acting factors). In some aspects the population of liver cells isolated from the population of cells the cells express increased levels of HOMER1, LAMP3, or BMPR2; or decreased levels of ABCB1, ITGA4, ABCB4, or PRNP.

Also provided by the invention are methods of isolating a population of cells that have an enriched capacity for transcription factor induced transdifferentiation by providing a heterogeneous population of human cells; introducing a nucleic acid construct comprising a glutamine synthetase response element (GSRE), or fragment thereof capable of activating glutamine synthetase transcription, operatively linked to a reporter protein and isolating the cells expressing the reporter protein. Optionally, the nucleic acid construct further comprises a promoter/enhancer. The reporter protein is a fluorescent protein. The reporter protein provides resistance to selection pressure. The cells are endothelial cells, fibroblasts, mesenchymal or liver cells. The liver cells are derived from the pericentral liver.

Optionally, the method further comprises culturing the isolated cells.

Also included in the invention is the population of cells isolated by the methods of according to the invention.

In other aspects the invention includes a method of treating or alleviating a symptom of a pancreatic disorder by introducing a pancreatic transcription factor to the cell population isolated according to the methods of the invention administering the cell population to a subject in need thereof. The pancreatic disorder is diabetes or pancreatitis.

The pancreatic transcription factor is Pdx-1, Pax-4, MafA, NeuroD1, or a combination thereof.

Further included in the invention are method of producing a population of cells having a mature pancreatic beta cell phenotype and function by contacting the population of cells isolated according to the invention with a pancreatic and duodenal homeobox (PDX-1) polypeptide, or a nucleic acid encoding a pancreatic and duodenal homeobox (PDX-1) polypeptide under conditions to allow uptake of the polypeptide, or nucleic acid at a first time period; further contacting the cells with a Pax-4 polypeptide, a NeuroD1 polypeptide, or nucleic acid encoding a Pax-4 polypeptide, or nucleic acid encoding a NeuroD1 polypeptide under conditions to allow uptake of the polypeptide or nucleic acid at a second time period; and further contacting the cells of step with a MafA polypeptide or a nucleic acid encoding a MafA polypeptide under conditions to allow uptake of the nucleic acid at a third time period. The second time period is at least 24 hours after the first time period. The third time period is at least 24 hours after the second time period. In some embodiments the first, second and third period of time are the same time Alternatively the invention provides a method of producing a population of cells having a mature pancreatic beta cell phenotype and function by contacting the population of cells isolated according to the invention with a pancreatic and duodenal homeobox (PDX-1) polypeptide or a nucleic acid encoding a pancreatic and duodenal homeobox (PDX-1) polypeptide and a second pancreatic transcription factor, under conditions to allow uptake of the PDX-1 polypeptide, or nucleic acid and the second pancreatic transcription factor at a first time period; and further contacting the cells with a MafA polypeptide, or a nucleic acid encoding a MafA polypeptide under conditions to allow uptake of the nucleic acid at a second time period. In some embodiments the second period of time is at least 2, 3, 4, 5, 6 or 7 days after the first period of time. The second pancreatic transcription factor is for example, NeuroD1, Pax-4, or Ngn3.

The nucleic acid is a ribonucleic acid or a deoxyribonucleic acid.

Optionally, the cells are further contacted with a nucleic acid encoding Sox-9 polypeptide or Sox-9 polypeptide under conditions to allow uptake of the nucleic acid or polypeptide.

The invention provides a nucleic acid construct comprising one or more glutamine synthetase response elements (GSRE), operably linked to a promoter and a reporter protein. The promoter is a weak promoter. The nucleic acid construct further contains a transcription factor. The transcription factor is a pancreatic transcription factor such as, Pdx-1, Pax-4, MafA, or NeuroD1. Also included in the invention is a vector containing the nucleic acid construct of the invention. The vector is an adenoviral vector.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

The FIGS. 1A-1D shows that Pdx-1 expression in human liver cells in vitro induces gradual activation of pancreatic hormone expression.

(FIG. 2A) Immunofluorescence (IF) staining shows expression of pTFs: Pdx-1 (left panel), Pax4 (middle left panel), MafA (middle right panel) and a merge of the 3 pTFs (right panel), with arrows indicating cells expressing all three pTFs. (FIG. 2B) Luciferase assay insulin promoter activation by the indicated pTFs; β-gal was used as a control. Results are expressed as Relative Light Unit (RLU)/mg protein. Each data point represents the mean±SE of at least two independent experiments, *p<0.05, **p<0.01 in comparison to control virus treated cells, (n>4). (FIG. 2C) Immunofluorescence staining shows insulin-positive cells after ectopic expression of the indicated pTFs. Original magnification ×20. Quantification of IF staining in table (right). The percent of insulin-positive cells was calculated by counting at least 500 positive cells from at least two independent experiments. (FIG. 2D) Insulin secretion after incubation with the indicated concentrations of glucose was detected by radioimmunoassay. *p<0.05, n≥12 in five independent experiments. The significance represents the differences between triple infection and all other treatments.

(FIG. 3A) A schematic demonstrating the order of infection of pTFs (treatments B-E) or control virus (Ad-CMV-β-gal, treatment A). (FIG. 3B) Immunofluorescence staining for insulin: treatment B (left panel), treatment C (middle panel), treatment D (right panel). Original magnification is at ×20. Quantification of staining (percent) is indicated below each image. The percent of insulin positive cells were calculated by counting at least 1000 positive cells from at least two independent experiments. (FIG. 3C) Insulin and (FIG. 3D) C-peptide secretion after incubation with the indicated concentration of glucose was measured by radioimmunoassay. Infection treatments are indicated on the X-axis and explained in Table 3A. *p<0.05, **p<0.01, compared to control virus treated cells; n≥12 in 5 independent experiments. (FIG. 3E) Expression levels of the indicated endogenous pancreas-specific transcription factors after the indicated treatments (X-axis) were measured by RT-PCR. CT values are normalized to β-actin gene expression within the same cDNA sample. Results are presented as relative levels of the mean±SE of the relative expression versus control virus treated cells, *p<0.05 n≥8 in 4 independent experiments. The arrow points the specific decrease in Isl-1 expression level under treatment C.

(FIG. 4A) Insulin promoter activation was measured by luciferase assay after the indicated infection treatments. Results are expressed as Relative Light Unit (RLU)/mg protein. Each data point represents the mean±SE of at least two independent experiments, *P<0.05, **P<0.01, compared to control virus treated cells, (n>4). (FIG. 4B) Analysis of glucose transporter 2 (GLUT2) expression levels by RT-PCR was performed after the indicated infection treatments. CT values are normalized to β-actin gene expression within the same cDNA sample. Results are presented as relative levels of the mean±SE compared to control virus treated cells. *P<0.05, compared to control virus treated cells n≥8 in 4 independent experiments. (FIG. 4C) Expression levels of prohormone convertase 2 (PC2; PCSK2) were determined by RT-PCR after the indicated infection treatments. CT values are normalized to β-actin gene expression within the same cDNA sample. Results are presented as relative levels of the mean±SE compared to control virus treated cells **P<0.01, n≥8 in 4 independent experiments.

(FIG. 5A) C-peptide secretion was measured by radioimmunoassay static incubation for 15 min at 0, 5, 10, 15, 20 mM glucose in cells treated by the direct "hierarchical" sequential order (treatment C) *P<0.05, n≥7 in 3 independent experiments. (FIG. 5B) C-peptide secretion was measured by radioimmunoassay over 13 or 28 days in serum free media supplemented with insulin, transferein and selenium (ITS), before being analyzed for c-peptide secretion. *P<0.05,**P<0.01, n≥5 in 2 independent experiments. The significance represents the differences compared to the standard protocol (treatment C on day 6).

(FIG. 6A) Insulin promoter activation was measured by luciferase assay. Results are presented mean±SE, *p<0.1, **p<0.05 compared to the direct "hierarchical" sequential infection order (treatment C), n≥6 in three independent experiments. (FIG. 6B) C-peptide secretion after incubation for 15 minutes with the indicated concentrations of glucose and measured by radioimmunoassay. *=p<0.05, **=p<0.01 in compared to the direct "hierarchical" sequential infection order (C), n≥6 in three independent experiments. (FIG. 6C) Expression levels of pancreatic enzymes were measured by RT-PCR: glucose transporter 2 (GLUT2); glucokinase (GCK); and prohormone convertase (PCSK2). (FIG. 6D) Expression levels of the indicated endogenous pancreatic transcription factors were measured by RT-PCR. CT values are normalized to β-actin gene expression within the same cDNA sample. Results are presented as relative levels of the mean±SE compared to "hierarchy sequential infection" treated liver cells. *p<0.05, **p<0.01, n≥6 in three independent experiments.

(FIG. 7A) Expression levels of insulin were measured by RT-PCR. CT values are normalized to β-actin gene expression within the same cDNA sample. Results are presented as relative levels of the mean±SE compared to control virus treated cells. *P<0.05, n≥6 in 3 independent experiments. (FIG. 7B) Insulin secretion was measured by radioimmunoassay. **P<0.01, n≥6 and compared to the direct "hierarchical" sequential infection order (C), n≥6 in 3 independent experiments. (FIG. 7C) Expression level of glucose transporter 2 (Glut2) was measured by RT-PCR.

(FIG. 8C) Expression levels of cell-specific transcription factors ARX and BRAIN4 were also measured by RT-PCR for the indicated infection treatments. (FIG. 8E) Expression levels of somatostatin (SST) were determined by RT-PCR after additional infection with Isl1 (100 MOI). CT values (for FIGS. 8A, 8B, 8C, and 8D) are normalized to β-actin gene expression within the same cDNA sample. Results are presented as relative levels of the mean±SE compared to control virus treated cells (a) or to "hierarchy sequential infection" treated liver cells (b-e). *P<0.05, **P<0.1, n≥6 in 3 independent experiments. (FIG. 8F) Immunofluorescence staining for somatostatin after treatment C infection (left panel), and after treatment C infection with additional Isl1 infection (right panel). Original magnification ×20. (FIG. 8G) Immunofluorescence staining for somatostatin and insulin showing that the sequential administration of transcription factors in a direct hierarchical manner results in increased maturation of the transdifferentiated cells along the beta-like-pancreatic lineage.

(FIG. 12A & FIG. 12D) Schematic presentations of Ad-GSRE-TK-Pdx-1 or GFP recombinant adenoviruses. Liver cells were infected with Ad-GSRE-TK-Pdx-1 (FIG. 12C) or with Ad-CMV-Pdx-1 (FIG. 12B). Immunoflorescent analysis of Pdx-1 expression indicated that 13±2% of the human liver cells infected by Ad-GSRETK-Pdx-1 (FIG. 12C) while 70±12% of Ad-CMV-Pdx-1-treated cells (FIG. 12B) expressed the ectopic nuclear factor (rabbit anti-Pdx-1, generous gift from C. Wright, pink; FIG. 12B & FIG. 12C, respectively) Similar results were obtained using Ad-GSRE-TK-eGFP; ~15% of the cells were positive to eGFP (FIG. 12E & FIG. 12F). Ad-CMV-eGFP infection resulted in about 75-80% eGFP positive cells within 3-4 days (data not presented)

(FIG. 13A & FIG. 13B), Immunoflorescent analysis of co-staining of insulin (Guinea pig anti-insulin, Dako, green) and (Pdx-1 rabbit anti-Pdx-1, generous gift from C. Wright, pink). (FIG. 13C) Statistical analysis o activation of insulin in the treated cells; Ad-GSRE-TK-Pdx-1 activated insulin production in 50%, whereas Ad-CMV-Pdx-1 only in 5% of the Pdx-1-positive cells. Blue-DAPI, nuclear staining; original magnification ×20.

(FIG. 14A) A schematic presentation of the lentivirus vectors. (FIG. 14B) Adult human liver cells at passages 3-10 were infected with the dual lentivirus system. Liver cells were imaged 10 days after infection for DsRed2 (red) or eGFP (green) fluorescence. (FIG. 14C) The cells were sorted by a fluorescence-activated cell sorter (FACS; Aria cell sorter; Becton Dickinson, San Jose, Calif.) with a fluorescein isothiocyanate filter (530/30 nm) for eGFP and a Pe-Texas Red filter (610/20 nm) for DsRed2. (FIGS. 14D & 14E). The separated cells were cultured separately for several passages (original magnification ×10).

(FIG. 16A) at the molecular level, insulin and glucagon gene expression was studied by Quantitative real-time compared to the control-treated cells. Cultured pancreatic human islet cells (Passage 3) used as a positive control. (FIGS. 16B & 16C) At the functional level, glucose-regulated insulin secretion was analyzed by static incubations at low followed by high glucose concentrations (2 mM and 17.5 mM glucose in KRB, respectively). Insulin (FIG. 16B) and C-peptide (FIG. 16C) secretion were measured using the human insulin radioimmunoassay kit (DPC; n≥8 from 3 different experiments) or human c-peptide radioimmunoassay kit (Linco n≥8 from 3 different experiments. *P<0.01 compared to the DsRed2+ cells, using Student's t-test analysis.

(FIG. 21A) APC and DKK1 expression is markedly increased in DsRed2+ cells. This may further suggest that these cells express higher levels of Wnt signaling pathway repressors compared with the eGFP+ cells. n≥6 from 2 different experiments *p<0.01 in DsRed2+ compared to eGFP+ cells, using Student's t-test analysis. (FIG. 21B) Western blot analysis using a specific antibody for activated β-catenin (anti-ABC clone 8E7, Millipore, 1:2000) in eGFP and DsRed2 positive cell extracts. β-actin (SC-1616, Santa Cruz, 1:1000) was used as a normalizing protein. (FIG. 21C) Quantification of the β-catenin protein levels was performed using ImageJ 1.29x software.

DETAILED DESCRIPTION OF THE PRESENT INVENTION

Figure 1:
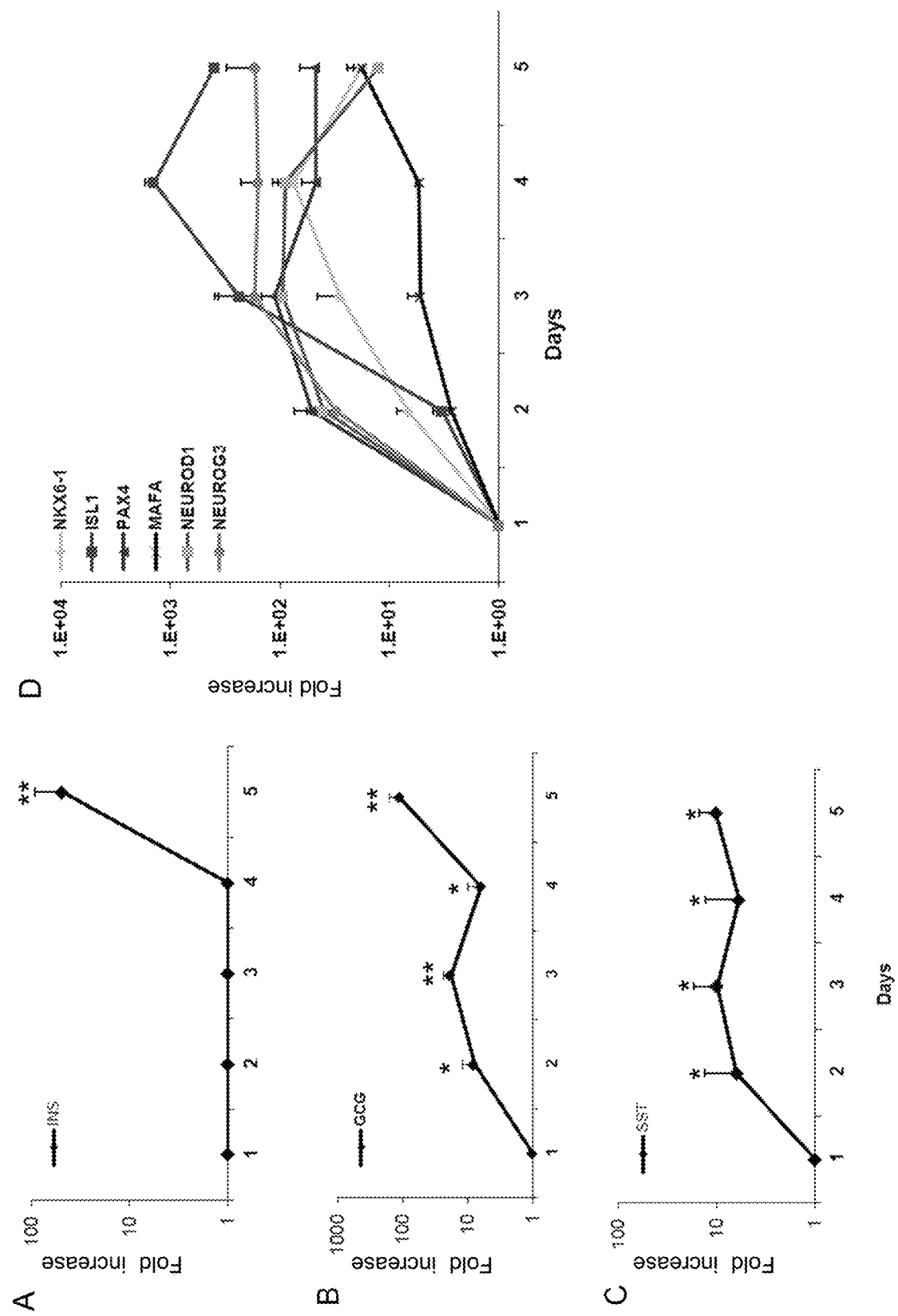
(FIG. 1A) Insulin (INS)
(FIG. 1B) glucagon (GCG)
(FIG. 1C) somatostatin (SST)
(FIG. 1D) other pancreas-specific transcription factors (NKX6.1, ISL1, PAX4, MAFA, NeuroD1, NeuroG3). The results were normalized to β-actin gene expression within the same cDNA sample and are presented as the mean±SE of the relative expression versus control virus treated cells on the same day. n≥4 in two independent experiments (*p<0.05, **p<0.01).

Transcription factors (TFs) have been shown to induce transdifferentiation in numerous cell lineages. As referred to herein, "transdifferentiation" refers to the process by which a first cell type loses identifying characteristics and changes its phenotype to that of a second cell type. In some embodiments, the first and second cells are from different tissues or cell lineages. Preferably, transdifferentiation involves converting a mature or differentiated cell to a different mature or differentiated cell. Specifically, lineage-specific transcription factors (TFs) have been suggested to display instructive roles in converting adult cells to endocrine pancreatic cells (Meivar-Levy et al, 2006; Meivar-Levy et al, 2010; Yechoor et al, 2010; Russ et al, 2011), neurons (Vierbuchen et al, 2010; Ambasudhan et al, 2011; Pang et al, 2011), hematopoietic cells (Szabo et al, 2010) and cardiomyocyte lineages (Ieda et al, 2010), suggesting that transdifferentiation processes occur in a wide spectrum of milieus. In all transdifferentiation protocols, the ectopic TFs serve as a short term trigger to a potential wide, functional and irreversible developmental process (Ber et al, 2003; Meivar-Levy et al, 2003; Meivar-Levy et al, 2006). Numerous studies suggested that ectopic expression of individual TFs activate a desired alternate repertoire and function, in a process involved with the activation of additional relevant otherwise silent TFs. However, the time course, the relative levels and the hierarchy, or order, of the induced TFs, remains unknown.

By exploiting the relative insufficiency of the endogenous transcription factor (TFs) induction by introducing individual ectopic TFs, the present invention relates transdifferentiation as a sequential and temporally controlled process which is affected by a hierarchical network of TFs.

The present invention is based on the finding that TF-induced liver to pancreas transdifferentiation is a gradual and consecutive process. Importantly, only sequential administration of pancreatic TFs but not their concerted expression selectively drives lineage specification programs within the endocrine pancreas. Sequential expression of pancreatic TFs in a direct hierarchical mode has been shown to be obligatory for transdifferentiated cell maturation along the β-cell lineage. Specifically, a role for the pancreatic β-cell specific transcription factor MafA has been identified in the final stage of the transdifferentiation process. At this stage, MafA promotes the maturation of transdifferentiated liver cells along the β-cell lineage, in a process associated with IsL1 and somatostatin repression.

The findings described herein suggest fundamental temporal characteristics of transcription factor-mediated transdifferentiation which could contribute to increasing the therapeutic merit of using TF-induced adult cell reprogramming for treating degenerative diseases including diabetes.

Pancreatic transcription factor (pTFs), such as Pdx-1, NeuroD1, Ngn-3 and Pax4, activate liver to pancreas transdifferentiation and individually induce amelioration of hyperglycemia in diabetic mice (Ferber et al, 2000; Ber et al, 2003; Kojima et al, 2003; Koizumi et al, 2004; Kaneto et al, 2005; Kaneto et al, 2005). Moreover, using an in vitro experimental system of adult human liver cells, we previously demonstrated that Pdx-1 activates the expression of numerous β-cell specific markers and induces glucose regulated secretion of processed insulin (Sapir et al, 2005; Meivar-Levy et al, 2007; Aviv et al, 2009; Gefen-Halevi et al, 2010; Meivar-Levy et al, 2011). The induced process was associated with the expression of numerous key endogenous pTFs and amelioration of hyperglycemia was demonstrated upon transplantation of the transdifferentiated adult human liver cells in diabetic mice (Sapir et al, 2005). However, numerous other studies have indicated that using combinations of several key TFs markedly increases the reprogramming efficiency compared to that induced by the ectopic expression of individual TFs (Kaneto et al, 2005; Tang et al, 2006; Song et al, 2007; Wang et al, 2007; Gefen-Halevi et al, 2010 Zhou et al, 2008; Vierbuchen et al, 2010; Ambasudhan et al, 2011; Pang et al, 2011). This suggests a potential restricted capacity of the individual ectopic factors to activate the endogenous complementing TFs to sufficient levels needed for an efficient transdifferentiation process (Kaneto et al, 2005; Zhou et al, 2008; Ambasudhan et al, 2011; Pang et al, 2011). Targeted disruption or temporal mis-expression of pancreatic transcription factors during pancreas organogenesis hampers pancreas development as well as islet cells differentiation and function (Nishimura et al, 2009). By exploiting the relative insufficiency of the endogenous TFs induction by individual ectopic TFs, the present invention is related to transdifferentiation as a sequential and temporally controlled process which is affected by a hierarchical network of TFs.

Pancreatic specification is initiated by the homeobox transcription factor Pdx1, which is also required for β-cell function in adults (Offield et al, 1996; Stoffers et al, 1997). The endocrine differentiation is then mediated by the basic helix-loop-helix factor Ngn3 (Gradwohl et al, 2000). The paired homeobox factors Pax4 and Arx, have been implicated as key factors in the segregation of the different endocrine cell types (Collombat et al, 2003; Brun et al, 2008). The final maturation along the β-cell lineage and function is attributed to selective expression of MafA in β-cells in the adult pancreas (Kataoka et al, 2002).

The present invention is based in part on the surprising finding that human liver cells can be directly transdifferentiated to produce an entirely different cell type, pancreatic hormones producing cells including beta-cells. Application of select transcription factors in a temporally-regulated sequence induced the transdifferentiation of adult liver cells to functional mature beta-cells. The invention solves the problem of producing large populations of insulin-producing cells, or pancreatic beta-cells, by providing methods for expanding and transdifferentiating adult cells. The compositions comprising the select transcription factors or the generated population of transdifferentiated pancreatic cells can be used for treating a pancreatic disorder using the methods described herein.

Previous efforts to transdifferentiate non-pancreatic cells to pancreatic cells, such as beta-cells, utilize either only one transcription factor or the concerted or simultaneous administration of more than one pancreatic transcription factor. The invention described herein provides methods for an ordered, sequential administration of specific transcription factors at defined timepoints. Furthermore, the methods described herein substantially increase the transdifferentiation efficiency compared to that induced by each of the individual transcription factors alone.

The present invention further provides a population of cells which possess increased transdifferentiation capacity. These cells are characterized by (1) potential cell membrane markers, (2) possessing the capacity to activate glutamine synthetase regulatory element (GSRE), and (3) by being uniquely equipped with active Wnt-signaling. At least 30% of the cells in the population are capable of activating GSRE. For example the cells are endothelial cells, epithelial cells, mesenchymal cells, fibroblasts, or liver cells. Preferably, the cells are human cells. In some embodiments, the cells can be transdifferentiated along the pancreatic lineage to mature pancreatic cells with pancreatic function. In other embodiments, the cells can be transdifferentiated along the neural lineage to neural cells.

Thus, the present invention also solves the problem of previous transdifferentiation or reprogramming protocols that often have restricted efficiency. For example, although ectopic expression of key pancreatic transcription factors results in expression in each host cell, only up to 15% of the cells are successfully transdifferentiated to exhibit pancreatic function.

The present invention also provides methods for isolating the population of cells with enriched or increased transdifferentiation capacity. For example, one method for isolating these cells is by sorting out cells which activate GFP expression operatively linked to the glutamine synthetase regulatory element, or a fragment thereof, thereby isolating those cells that can activate GSRE. The cells may be sorted by FACS and can be propagated in culture, separately from the rest of the cells, for rapid expansion of the cells with enriched transdifferentiation capacity. The population of cells with enriched capacity for transdifferentiation is only a small proportion of the cells that make up the tissue in vivo. For example, in a given tissue or population of cells, the population of cells with enriched capacity for transdifferentiation is only about less than 1%, 2%, 3%, 4%, 5%, about 10%, about 15%, of the entire population of cells in a given tissue. Therefore, the present invention also provides methods for the isolation of said cells with increased transdifferentiation capacity from cells that do not have increased transdifferentiation capacity. Accordingly, the present invention provides the advantage of a cell population with a greater proportion of cells that have increased transdifferentiation capacity to increase the efficiency of transdifferentiation to provide transdifferentiated cells for treatment of various diseases or disorders.

It will be obvious to those skilled in the art that various changes and modifications may be made to the methods described herein within the spirit and scope of the invention.

Methods of Producing Pancreatic Beta-Cells

The present invention provides methods for producing cells that exhibit a mature pancreatic beta cell phenotype by contacting adult mammalian non-pancreatic cells with pancreatic transcription factors, such as PDX-1, Pax-4, NeuroD1, and MafA, at specific timepoints. In some embodiments, the methods comprise contacting an adult mammalian non-pancreatic cell with PDX-1 at a first time period; contacting the cells from the first step with Pax-4 at a second time period; and contacting the cells from the second step with MafA at a third time period. In one embodiment, the methods comprise contacting an adult mammalian non-pancreatic cell with PDX-1 at a first time period; contacting the cells from the first step with NeuroD1 at a second time period; and contacting the cells from the second step with MafA at a third time period. In another embodiment, the methods comprise contacting an adult mammalian non-pancreatic cell with PDX-1 and a second transcription factor at a first time period and contacting the cells from the first step with MafA at a second time period. The transcription factors may be polypeptides, ribonucleic acids or nucleic acids encoding the transcription factor polypeptides. For example, the transcription factors provided together with PDX-1 are Pax-4, NeuroD1, Ngn3, or Sox-9. Preferably, the transcription factor is NeuroD1.

In one aspect, the methods described herein further comprise contacting the cells at, before, or after any of the above steps with the transcription factor Sox-9.

In one aspect, the second time period is at least 24 hours after the first time period. In one aspect, the third time period is at least 24 hours after the second time period. In some embodiments, the second and third time period can be at least 24 hours, at least 48 hours, at least 72 hours, and at least 1 week or more after the first or second time period, respectively.

Transcription factors for use in the present invention can be a polypeptide, ribonucleic acid or a nucleic acid. As used herein, the term "nucleic acid" is intended to include DNA molecules (e.g., cDNA or genomic DNA), RNA molecules (e.g., mRNA, microRNA or other RNA derivatives), analogs of the DNA or RNA generated using nucleotide analogs, and derivatives, fragments and homologs thereof. The nucleic acid molecule can be single-stranded or double-stranded. Preferably, the nucleic acid is a DNA.

Preferred transcription factors for use in the methods described herein are PDX-1, Pax-4, NeuroD1, and MafA. Other transcription factors that may be used are Ngn3, and Sox9.

The homeodomain protein PDX-1 (pancreatic and duodenal homeobox gene-1), also known as IDX-1, STF-1, or IUF-1, plays a central role in regulating pancreatic islet development and function. PDX-1 is either directly or indirectly involved in islet-cell-specific expression of various genes such as, for example insulin, glucagon, somatostatin, proinsulin convertase 1/3 (PC1/3), GLUT-2 and glucokinase. Additionally, PDX-1 mediates insulin gene transcription in response to glucose. Suitable sources of nucleic acids encoding PDX-1 include for example the human PDX-1 nucleic acid (and the encoded protein sequences) available as GenBank Accession Nos. U35632 and AAA88820, respectively. Other sources include rat PDX nucleic acid and protein sequences are shown in GenBank Accession No. U35632 and AAA18355, respectively, and are incorporated herein by reference in their entirety. An additional source includes zebrafish PDX-1 nucleic acid and protein sequences are shown in GenBank Accession No. AF036325 and AAC41260, respectively, and are incorporated herein by reference in their entirety.

Pax-4, also known as paired box 4, paired box protein 4, paired box gene 4, MODY9 and KPD, is a pancreatic-specific transcription factor that binds to elements within the glucagon, insulin and somatostatin promoters, and is thought to play an important role in the differentiation and development of pancreatic islet beta cells. In some cellular contexts, Pax-4 exhibits repressor activity. Suitable sources of nucleic acids encoding Pax-4 include for example the human Pax-4 nucleic acid (and the encoded protein sequences) available as GenBank Accession Nos. NM_006193.2 and AAD02289.1, respectively.

MafA, also known as V-maf musculoaponeurotic fibrosarcoma oncogene homolog A or RIPE3B1, is a beta-cell-specific and glucose-regulated transcriptional activator for insulin gene expression. MafA may be involved in the function and development of beta-cells as well as in the pathogenesis of diabetes. Suitable sources of nucleic acids encoding MafA include for example the human MafA nucleic acid (and the encoded protein sequences) available as GenBank Accession Nos. NM_201589.3 and NP_963883.2, respectively.

Neurog3, also known as neurogenin 3 or Ngn3, is a basic helix-loop-helix (bHLH) transcription factor required for endocrine development in the pancreas and intestine. Suitable sources of nucleic acids encoding Neurog3 include for example the human Neurog3 nucleic acid (and the encoded protein sequences) available as GenBank Accession Nos. NM_020999.3 and NP_066279.2, respectively.

NeuroD1, also known as Neuro Differentiation 1, and beta-2 (□2) is a Neuro D-type transcription factor. It is a basic helix-loop-helix transcription factor that forms heterodimers with other bHLH proteins and activates transcription of genes that contain a specific DNA sequence known as the E-box. It regulates expression of the insulin gene, and mutations in this gene result in type II diabetes mellitus. Suitable sources of nucleic acids encoding NeuroD1 include for example the human NeuroD1 nucleic acid (and the encoded protein sequences) available as GenBank Accession Nos. NM_002500.4 and NP_002491.2, respectively.

Sox9 is a transcription factor that is involved in embryonic development. Sox9 has been particularly investigated for its importance in bone and skeletal development. SOX-9 recognizes the sequence CCTTGAG along with other members of the HMG-box class DNA-binding proteins. In the context of the present invention, the use of Sox9 may be involved in maintaining the pancreatic progenitor cell mass, either before or after induction of transdifferentiation. Suitable sources of nucleic acids encoding NeuroD1 include for example the human NeuroD1 nucleic acid (and the encoded protein sequences) available as GenBank Accession Nos. NM_000346.3 and NP_000337.1, respectively.

The cell can be any cell that is capable of producing pancreatic hormones, e.g., bone marrow muscle, spleen, kidney, blood, skin, pancreas, or liver. In one embodiment, the cell is a non-pancreatic cell. In one embodiment, the cell is capable of functioning as a pancreatic islet cell, i.e., store, process and secrete pancreatic hormones, preferably insulin, upon an extracellular trigger. In another embodiment the cell is a liver cell. In additional embodiments the cell is totipotent or pluripotent. In alternative embodiments the cell is a hematopoietic stem cell, embryonic stem cell or preferably a hepatic stem cell.

The cell population that is exposed to, i.e., contacted with, the compounds (i.e. PDX-1, Pax-4, MafA, NeuroD1 and/or Sox-9 polypeptides or nucleic acid encoding PDX-1, Pax-4, MafA, NeuroD1 and/or Sox-9 polypeptides) can be any number of cells, i.e., one or more cells, and can be provided in vitro, in vivo, or ex vivo. The cell population that is contacted with the transcription factors can be expanded in vitro prior to being contacted with the transcription factors. The cell population produced that exhibits a mature pancreatic beta cell phenotype. These cells can be expanded in vitro by methods known in the art prior to transdifferentiation and maturation along the □-cell lineage, and prior to administration or delivery to a patient or subject in need thereof.

The subject is preferably a mammal. The mammal can be, e.g., a human, non-human primate, mouse, rat, dog, cat, horse, or cow.

In some embodiments, the transcription factor is a polypeptide, such as PDX-1, Pax-4, MafA, NeuroD1 or Sox-9, or combination thereof and is delivered to a cell by methods known in the art. For example, the transcription factor polypeptide is provided directly to the cells or delivered via a microparticle or nanoparticle, e.g., a liposomal carrier.

In some embodiments, the transcription factor is a nucleic acid. For example, the nucleic acid encodes a PDX-1, Pax-4, MafA, NeuroD1 or Sox-9 polypeptide. The nucleic acid encoding the transcription factor, or a combination of such nucleic acids, can be delivered to a cell by any means known in the art. In some embodiments, the nucleic acid is incorporated in an expression vector or a viral vector. Preferably, the viral vector is an adeno-virus viral vector. The expression or viral vector can be introduced to the cell by any of the following: transfection, electroporation, infection, or transduction.

Cell Populations Predisposed for Transdifferentiation

The present invention provides liver derived cell populations that are predisposed for transdifferentiation. The cell populations are useful in the methods of producing pancreatic beta cells described herein. Cells that are predisposed for transdifferentiation of the present invention are also referred to as having increased or enriched transdifferentiation capacity. By "increased transdifferentiation capacity" is meant that when the cell population of the present invention is subjected to a differentiation protocol (i.e. introduction of a pancreatic transcription factor), greater than 15%, greater than 20%, greater then 30%, greater than 40%, greater than 50%, greater than 60%, greater than 70% or greater than 80% will differentiate to an alternate cell type. For example, a population of endothelial cells, epithelial cells, mesenchymal cells, fibroblasts, or liver cells with increased transdifferentiation capacity can be differentiated to mature pancreatic cells or mature neural cells.

In another embodiment, cell populations that are predisposed for transdifferentiation have the capability of activating the glutamine synthetase response element (GSRE). For example, in the cell populations of the present invention, at least 2%, at least 3%, at least 4%, at least 5%, at least 10%, at least 15%, at least 20%, at least 30%, at least 40%, at least 50%, at least 60%, at least 70%, at least 80% or at least 90% of the cells in the population are capable of activating GSRE. Preferably, at least 30% of the cells in the population are capable of activating GSRE. Glutamine synthetase is an enzyme predominantly expressed in the brain, kidneys and liver, and plays an essential role in the metabolism of nitrogen by catalyzing the condensation of glutamate and ammonia to form glutamine. Glutamine synthetase is, for example, uniquely expressed in pericentral liver cells and astrocytes in the brain. Data presented herein indicate that cells that demonstrate activation of GSRE provide a unique selective parameter for the isolation of cells predisposed for transdifferentiation.

Activation of GSRE can be measured by methods known to one of ordinary skill in the art. For example, a recombinant adenovirus can be generated containing the glutamine synthetase response element operatively linked to a promoter and a reporter gene, such as a fluorescent protein. This recombinant adenovirus with the GSRE-reporter can be introduced into a heterogeneous mixture of cells containing some proportion of cells that are predisposed for transdifferentiation. Those cells that are competent for activation of the GSRE will express the reporter gene, which can be detected by methods known in the art, thereby identifying cells predisposed for transdifferentiation.

Figure 14:
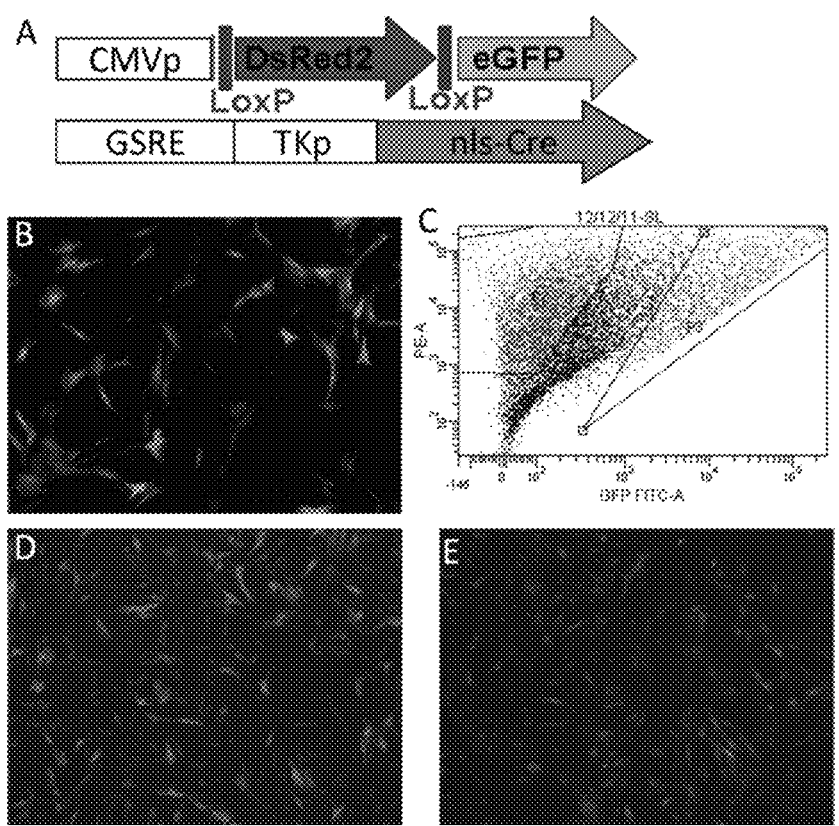
FIGS. 14A-14E. In vitro lineage tracing for GSRE activating human cells.
Figure 17:
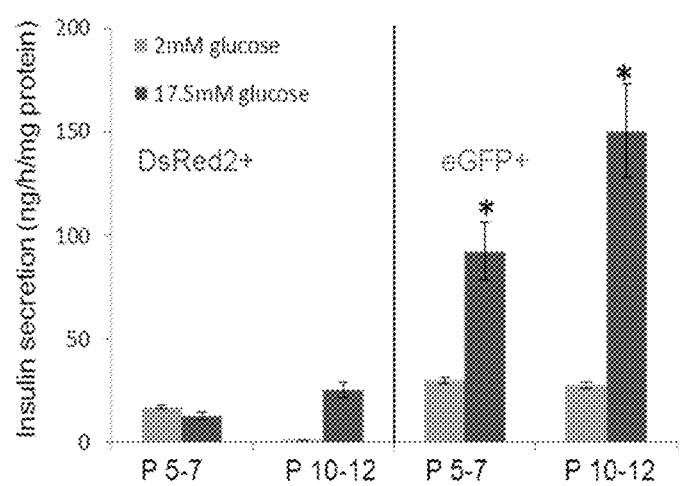
FIG. 17. Higher transdifferentiation efficiency in eGFP+ population is stable with increasing passages in culture. The two groups proliferated separately after sorting and were similarly treated with pTFs (Ad-Pdx-1+Ad-Pax-4+ad-MafA and soluble factors) after a few passages (5-7 passages post sorting) or a higher number of passages (10-12 passages post sorting). Regulated insulin secretion was analyzed by static incubations at low followed by high glucose concentrations (2 mM and 17.5 mM glucose in KRB, respectively). Insulin secretion is measured using the human insulin radioimmunoassay kit (DPC; n≥6 from 2 different experiments). No statistical significant differences were detected between the low and high number of passages in both population of cells, suggesting a persistent tendency of eGFP tagged cells to undergo pTFs induced transdifferentiation along the β-cell lineage and function.

A heterogeneous population of cells, in which those cells predisposed for transdifferentiation are unknown, can be contacted with an adenoviral vector that contains the GSRE operatively linked to a minimal TK promoter and eGFP. The cells that can activate the GSRE will express GFP and can be identified by various methods known in the art to detect GFP expression. For example, separation of the GSRE-activated cells which are predisposed for transdifferentiation from the cells that are not predisposed for transdifferentiation can be achieved through FACs apparatus, sorter and techniques known to those ordinarily skilled in the art (FIG. 14). The separated cells which are predisposed for transdifferentiation can then be propagated or expanded in vitro. Results described herein demonstrate that passaging of the cells predisposed for transdifferentiation for 5-12 passages or more retain their transdifferentiation capacity. For example, isolated liver cells predisposed for transdifferentiation continue to produce and secrete insulin in a glucose-dependent manner even after 12 passages in culture (FIG. 17).

In another embodiment, cell populations that are predisposed for transdifferentiation also have active Wnt signaling pathways. Wnt signaling pathways play a significant role in stem cell pluripotency and cell fate during development, as well as body axis patterning, cell proliferation, and cell migration. Wnt signaling pathways are activated by the binding of a Wnt-protein ligand to a Frizzled (Fz) family receptor (a G-coupled protein receptor), optionally activating a co-receptor protein, and the subsequent activation of a cytoplasmic protein called Dishevelled (Dsh). In the canonical Wnt pathway, co-receptor LRP-5/6 is also activated and beta-catenin accumulates in the cytoplasm and is eventually translocated into the nucleus to act as a transcriptional coactivator of TCF/LEF transcription factors. Without Wnt signaling, a destruction complex which includes proteins adenomatosis polyposis coli (APC), Axin, protein phosphatase 2A (PP2A), glycogen synthase kinase 3 (GSK3) and casein kinase 1 □(CK1□) targets □-catenin for ubiquitination and its subsequent degradation by the proteasome. However, activation of the Frizzled receptor by Wnt binding causes disruption of the destruction complex, thereby allowing □-catenin to accumulate.

Wnt signaling can also occur through noncanonical pathways that utilize different co-receptor proteins and activate different downstream effectors to, for example, regulate of the cytoskeleton, stimulate of calcium release from the endoplasmic reticulum, activate mTOR pathways, and regulate myogenesis.

One of ordinary skill in the art could readily use methods known in the art to determine the activation of Wnt signaling pathways. For example, cells that express Wnt3a, decreased levels of DKK1 or DKK3, decreased levels of APC, increased activated beta-catenin levels, or STAT5 binding elements have active Wnt signaling pathways. DKK1, DKK3, and APC are known inhibitors of Wnt signaling pathways. Other signaling effectors that indicate active Wnt signaling pathways are readily known in the art.

Preferably, the cell populations are predisposed for transdifferentiation to the pancreatic lineage, wherein the transdifferentiated cells exhibit pancreatic phenotype and function. For example, the transdifferentiated cells exhibit mature pancreatic beta cell phenotype and function, which includes, but is not limited to, expression, production, and/or secretion of pancreatic hormones. Pancreatic hormones can include, but are not limited to, insulin, somatostatin, glucagon, or islet amyloid polypeptide (IAPP). Insulin can be hepatic insulin or serum insulin. Preferably the insulin is a fully process form of insulin capable of promoting flucose utilization, and carbohydrate, fat and protein metabolism. For example, the cells predisposed for transdifferentiation may encompass about 15% of all the cells in a heterogeneous in vitro primary human liver cell culture. When the cells ectopically express pTFs, greater than 5%, 10%, 15%, 20%, 25%, 30%, 40%, 50% of the cells in culture produce insulin or secrete c-peptide.

In one embodiment, cell populations that are predisposed for transdifferentiation are located in close proximity to the central veins of the liver, or are pericentral liver cells. As shown herein, although over 40-50% of liver cells that ectopically express pancreatic transcription factors, such as PDX-1, only a subset of cells produced insulin upon pTF expression. These insulin-producing cells (IPCs) were primarily located close to the ventral veins, as shown by FIG. 1B. These cells are also characterized by expression of glutamine synthetase and active Wnt signaling.

In another preferred embodiment, the cell populations of the present invention are predisposed for transdifferentiation to the neural lineage, wherein the transdifferentiated cells express neural markers, exhibit neural phenotype, or exhibit neural function. The transdifferentiated cells can be neurons or glial cells.

In another embodiment, cells with increased predisposition for transdifferentiation may be identified through specific cell surface markers. For example, cells with increased levels of HOMER1, LAMP5 or BMPR2 indicate cells with increased transdifferentiation capacity when compared to cells without predisposition for transdifferentiation. Cells with decreased levels of ABCB1, ITGA4, ABCB4, or PRNP indicate cells with increased transdifferentiation capacity when compared to cells without predisposition for transdifferentiation. Any combination of the cell surface markers described can be used to distinguish a cell population predisposed to transdifferentiation from a cell population that is not predisposed to transdifferentiation. Antibodies to these cell surface markers are commercially available. Immuno-assay or immune-affinity techniques known in the art may be utilized to distinguish cells with increased transdifferentiation capacity from those cells without transdifferentiation capacity.

Use of the cell populations of the present invention to produce cells that exhibit pancreatic cell phenotypes provide certain advantages over differentiating heterogeneous populations of non-pancreatic cells to produce cells that exhibit pancreatic cell phenotypes. Previous studies that describe expressing a pancreatic transcription factor (pTF) such as PDX-1 in a heterogeneous population of non-pancreatic cells (i.e., liver cells) show that at best, only 15% of the PDX-1-expressing cells are competent for producing insulin. Therefore, only 15% of the cells were successfully differentiated to a mature pancreatic beta-cell capable of producing and secreting pancreatic hormones. In contrast, introducing pTFs into the cell populations of the present invention results in at least 30%, at least 40%, at least 50%, at least 60%, at least 70%, or at least 80% of the cells are differentiated to a mature pancreatic beta cell phenotype, for example, produce insulin, glucagon, and/or secrete c-peptide. Preferably, when the cells of the cell population of the present invention express a pancreatic transcription factor, at least 30% of the cells produce insulin or secrete c-peptide.

Methods of Transdifferentiation

The present invention also provides methods for utilizing the cell populations with increased transdifferentiation capacity to produce cells that exhibit a mature differentiated cell type, where the differentiated cell has a different phenotype from the starting cell population. For example, a population of cells with increased transdifferentiation capacity (i.e. epithelial cells, fibroblasts or liver cells) can be differentiated to cells along the pancreatic or neural lineage to exhibit mature differentiated pancreatic or neural cell phenotypes. Any means known in the art for differentiating cells to pancreatic or neural lineage can be utilized.

In one embodiment, the cell population predisposed for transdifferentiated may be differentiated along the neural lineage through the expression of neural transcription factors. Suitable neural transcription factors are known in the art. In other embodiments, the cell population of the present invention may be differentiated to mature neural cells through contacting the cells with various cytokines, growth factors, or other agents known in the art to differentiate cells to the neural lineage. The differentiated neural cells may express neural markers, exhibit a neural phenotype (i.e., neural gene expression profile), or exhibit neural function. The differentiated cells can be neurons or glial cells.

In another embodiment, the cell population predisposed for transdifferentiation may be differentiated along the pancreatic lineage through the expression of pancreatic transcription factors. The pancreatic transcription factors are, for example, PDX-1, Pax-4, MafA, NeuroD1, or a combination thereof. Methods for producing pancreatic beta cells are described in U.S. Pat. No. 6,774,120 and U.S. Publication No. 2005/0090465, the contents of which are incorporated by reference in their entireties.

In another embodiment, the cell population predisposed for transdifferentiation may be differentiated along the pancreatic lineage through the methods described herein.

Pancreatic Beta-Cell Phenotypes

The methods provided herein produce cells with a mature pancreatic beta cell phenotype or function. By "pancreatic beta cell phenotype or function" is meant that the cell displays one or more characteristics typical of pancreatic beta cells, i.e. pancreatic hormone production, processing, storage in secretory granules, hormone secretion, activation of pancreatic gene promoters, or characteristic beta cell gene expression profile. Hormone secretion includes nutritionally and/or hormonally regulated secretion. Preferably, the cells produced exhibit at least one pancreatic beta cell phenotype or function, as described herein.

The pancreatic hormone can be for example, insulin, glucagon, somatostatin or islet amyloid polypeptide (IAPP). Insulin can be hepatic insulin or serum insulin. In another embodiment the pancreatic hormone is hepatic insulin. In an alternative embodiment the pancreatic hormone is serum insulin (i.e., a fully processed form of insulin capable of promoting, e.g., glucose utilization, carbohydrate, fat and protein metabolism).

In some embodiments the pancreatic hormone is in the "prohormone" form. In other embodiments the pancreatic hormone is in the fully processed biologically active form of the hormone. In other embodiments the pancreatic hormone is under regulatory control i.e., secretion of the hormone is under nutritional and hormonal control similar to endogenously produced pancreatic hormones. For example, in one aspect of the invention the hormone is under the regulatory control of glucose. Insulin secretion can also be measured by, for example, C-peptide processing and secretion.

The pancreatic beta cell phenotype can be determined for example by measuring pancreatic hormone production, i.e., insulin, somatostatin or glucagon protein mRNA or protein expression. Hormone production can be determined by methods known in the art, i.e. immunoassay, western blot, receptor binding assays or functionally by the ability to ameliorate hyperglycemia upon implantation in a diabetic host.

In some embodiments, the cells can be directed to produce and secrete insulin using the methods specified herein. The ability of a cell to produce insulin can be assayed by a variety of methods known to those of ordinary skill in the art. For example, insulin mRNA can be detected by RT-PCR or insulin may be detected by antibodies raised against insulin. In addition, other indicators of pancreatic differentiation include the expression of the genes Isl-1, Pdx-1, Pax-4, Pax-6, and Glut-2. Other phenotypic markers for the identification of islet cells are disclosed in U.S. 2003/0138948, incorporated herein in its entirety.

The pancreatic beta cell phenotype can be determined for example by promoter activation of pancreas-specific genes. Pancreas-specific promoters of particular interest include the promoters for insulin and pancreatic transcription factors, i.e. endogenous PDX-1. Promoter activation can be determined by methods known in the art, for example by luciferase assay, EMSA, or detection of downstream gene expression.

In some embodiments, the pancreatic beta-cell phenotype can also be determined by induction of a pancreatic gene expression profile. By "pancreatic gene expression profile" it is meant: to include expression of one or more genes that are normally transcriptionally silent in non-endocrine tissues, i.e., a pancreatic transcription factor, pancreatic enzymes or pancreatic hormones. Pancreatic enzymes are, for example, PCSK2 (PC2 or prohormone convertase), PC1/3 (prohormone convertase 1/3), glucokinase, glucose transporter 2 (GLUT-2). Pancreatic-specific transcription factors include, for example, Nkx2.2, Nkx6.1, Pax-4, Pax-6, MafA, NeuroD1, NeuroG3, Ngn3, beta-2, ARX, BRAIN4 and Isl-1.

Induction of the pancreatic gene expression profile can be detected using techniques well known to one of ordinary skill in the art. For example, pancreatic hormone RNA sequences can be detected in, e.g., northern blot hybridization analyses, amplification-based detection methods such as reverse-transcription based polymerase chain reaction or systemic detection by microarray chip analysis. Alternatively, expression can be also measured at the protein level, i.e., by measuring the levels of polypeptides encoded by the gene. In a specific embodiment PC1/3 gene or protein expression can be determined by its activity in processing prohormones to their active mature form. Such methods are well known in the art and include, e.g., immunoassays based on antibodies to proteins encoded by the genes, or HPLC of the processed prohormones.

In some embodiments, the cells exhibiting a mature beta-cell phenotype generated by the methods described herein may repress at least one gene or the gene expression profile of the original cell. For example, a liver cell that is induced to exhibit a mature beta-cell phenotype may repress at least one liver-specific gene. One skilled in the art could readily determine the liver-specific gene expression of the original cell and the produced cells using methods known in the art, i.e. measuring the levels of mRNA or polypeptides encoded by the genes. Upon comparison, a decrease in the liver-specific gene expression would indicate that transdifferentiation has occurred.

Methods of Treating a Pancreatic Disorder

The present invention discloses methods for use in treating, i.e., preventing or delaying the onset or alleviating a symptom of a pancreatic disorder in a subject. For example, the pancreatic disorder is a degenerative pancreatic disorder. The methods disclosed herein are particularly useful for those pancreatic disorders that are caused by or result in a loss of pancreatic cells, e.g., islet beta-cells, or a loss in pancreatic cell function.

Common degenerative pancreatic disorders include, but are not limited to: diabetes (e.g., type I, type II, or gestational) and pancreatic cancer. Other pancreatic disorders or pancreas-related disorders that may be treated by using the methods disclosed herein are, for example, hyperglycemia, pancreatitis, pancreatic pseudocysts or pancreatic trauma caused by injury.

Diabetes is a metabolic disorder found in three forms: type 1, type 2 and gestational. Type 1, or IDDM, is an autoimmune disease; the immune system destroys the pancreas' insulin-producing beta cells, reducing or eliminating the pancreas' ability to produce insulin. Type 1 diabetes patients must take daily insulin supplements to sustain life. Symptoms typically develop quickly and include increased thirst and urination, chronic hunger, weight loss, blurred vision and fatigue. Type 2 diabetes is the most common, found in 90 percent to 95 percent of diabetes sufferers. It is associated with older age, obesity, family history, previous gestational diabetes, physical inactivity and ethnicity. Gestational diabetes occurs only in pregnancy. Women who develop gestational diabetes have a 20 percent to 50 percent chance of developing type 2 diabetes within five to 10 years.

A subject suffering from or at risk of developing diabetes is identified by methods known in the art such as determining blood glucose levels. For example, a blood glucose value above 140 mg/dL on at least two occasions after an overnight fast means a person has diabetes. A person not suffering from or at risk of developing diabetes is characterized as having fasting sugar levels between 70-110 mg/dL.

Symptoms of diabetes include fatigue, nausea, frequent urination, excessive thirst, weight loss, blurred vision, frequent infections and slow healing of wounds or sores, blood pressure consistently at or above 140/90, HDL cholesterol less than 35 mg/dL or triglycerides greater than 250 mg/dL, hyperglycemia, hypoglycemia, insulin deficiency or resistance. Diabetic or pre-diabetic patients to which the compounds are administered are identified using diagnostic methods know in the art.

Hyperglycemia is a pancreas-related disorder in which an excessive amount of glucose circulates in the blood plasma. This is generally a glucose level higher than (200 mg/dl). A subject with hyperglycemia may or may not have diabetes.

Pancreatic cancer is the fourth most common cancer in the U.S., mainly occurs in people over the age of 60, and has the lowest five-year survival rate of any cancer. Adenocarcinoma, the most common type of pancreatic cancer, occurs in the lining of the pancreatic duct; cystadenocarcinoma and acinar cell carcinoma are rarer. However, benign tumors also grow within the pancreas; these include insulinoma—a tumor that secretes insulin, gastrinoma—which secretes higher-than-normal levels of gastrin, and glucagonoma—a tumor that secretes glucagon.

Pancreatic cancer has no known causes, but several risks, including diabetes, cigarette smoking and chronic pancreatitis. Symptoms may include upper abdominal pain, poor appetite, jaundice, weight loss, indigestion, nausea or vomiting, diarrhea, fatigue, itching or enlarged abdominal organs. Diagnosis is made using ultrasound, computed tomography scan, magnetic resonance imaging, ERCP, percutaneous transhepatic cholangiography, pancreas biopsy or blood tests. Treatment may involve surgery, radiation therapy or chemotherapy, medication for pain or itching, oral enzymes preparations or insulin treatment.

Pancreatitis is the inflammation and autodigestion of the pancreas. In autodigestion, the pancreas is destroyed by its own enzymes, which cause inflammation. Acute pancreatitis typically involves only a single incidence, after which the pancreas will return to normal. Chronic pancreatitis, however, involves permanent damage to the pancreas and pancreatic function and can lead to fibrosis. Alternately, it may resolve after several attacks. Pancreatis is most frequently caused by gallstones blocking the pancreatic duct or by alcohol abuse, which can cause the small pancreatic ductules to be blocked. Other causes include abdominal trauma or surgery, infections, kidney failure, lupus, cystic fibrosis, a tumor or a scorpion's venomous sting.

Symptoms frequently associated with pancreatitis include abdominal pain, possibly radiating to the back or chest, nausea or vomiting, rapid pulse, fever, upper abdominal swelling, ascites, lowered blood pressure or mild jaundice. Symptoms may be attributed to other maladies before being identified as associated with pancreatitis.

Method of Treating a Neurological Disorders

The present invention also provides methods for treating a subject with a neurological disease or disorder, such as a neurodegenerative disease disorder. The population of cells described herein is useful for treating a subject with a neurological disease or disorder that is characterized by loss of neural cells or neural function, by way of replenishing the degenerated or nonfunctional cells. Neurodegenerative diseases that may be treated using the methods described herein include, but are not limited to, Parkinson's disease, Parkinsonian disorders, Alzheimer's disease, Huntington's disease, amyotrophic lateral sclerosis, Lewy body disease, age-related neurodegeneration, neurological cancers, and brain trauma resulting from surgery, accident, ischemia, or stroke. The population of cells described herein can be differentiated to a neural cell population with neural function, and the differentiated neural cell population may be administered to a subject with a neurological disease or disorder.

Therapeutics Compositions

The herein-described transdifferentiation-inducing compounds, or ectopic pancreatic transcription factors (i.e., PDX-1, Pax-4, MafA, NeuroD1 or Sox-9 polypeptides, ribonucleic acids or nucleic acids encoding PDX-1, Pax-4, MafA, NeuroD1 or Sox-9 polypeptides), when used therapeutically, are referred to herein as "Therapeutics". Methods of administration of Therapeutics include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. Various delivery systems are known and can be used to administer a Therapeutic of the present invention including, e.g.: (i) encapsulation in liposomes, microparticles, microcapsules; (ii) recombinant cells capable of expressing the Therapeutic; (iii) receptor-mediated endocytosis (See, e.g., Wu and Wu, 1987. J Biol Chem 262:4429-4432); (iv) construction of a Therapeutic nucleic acid as part of a retroviral, adenoviral or other vector, and the like. In one embodiment of the present invention, the Therapeutic may be delivered in a vesicle, in particular a liposome. In a liposome, the protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028; and 4,737,323, all of which are incorporated herein by reference. In yet another embodiment, the Therapeutic can be delivered in a controlled release system including, e.g.: a delivery pump (See, e.g., Saudek, et al., 1989. New Engl J Med 321:574 and a semi-permeable polymeric material (See, e.g., Howard, et al., 1989. J Neurosurg 71:105). Additionally, the controlled release system can be placed in proximity of the therapeutic target (e.g., the brain), thus requiring only a fraction of the systemic dose. See, e.g., Goodson, In: Medical Applications of Controlled Release 1984. (CRC Press, Boca Raton, Fla.).

In a specific embodiment of the present invention, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. Proc Natl Acad Sci USA 88:1864-1868), and the like. Alternatively, a nucleic acid Therapeutic can be introduced intracellularly and incorporated within host cell DNA for expression, by homologous recombination or remain episomal.

Preferably, the Therapeutic is administered intravenously. Specifically, the Therapeutic can be delivered via a portal vein infusion.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. However, suitable dosage ranges for intravenous administration of the Therapeutics of the present invention are generally at least 1 million transdifferentiated cells, at least 2 million transdifferentiated cells, at least 5 million transdifferentiated cells, at least 10 million transdifferentiated cells, at least 25 million transdifferentiated cells, at least 50 million transdifferentiated cells, at least 100 million transdifferentiated cells, at least 200 million transdifferentiated cells, at least 300 million transdifferentiated cells, at least 400 million transdifferentiated cells, at least 500 million transdifferentiated cells, at least 600 million transdifferentiated cells, at least 700 million transdifferentiated cells, at least 800 million transdifferentiated cells, at least 900 million transdifferentiated cells, at least 1 billion transdifferentiated cells, at least 2 billion transdifferentiated cells, at least 3 billion transdifferentiated cells, at least 4 billion transdifferentiated cells, or at least 5 billion transdifferentiated cells. Preferably, the dose is 1-2 billion transdifferentiated cells into a 60-75 kg subject. One skilled in the art would appreciate that effective doses may be extrapolated from dose-response curves derived from in vitro or animal model test systems.

The duration of intravenous therapy using the Therapeutic of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of therapy using the pharmaceutical composition of the present invention.

Cells may also be cultured ex vivo in the presence of therapeutic agents, nucleic acids, or proteins of the present invention in order to proliferate or to produce a desired effect on or activity in such cells. Treated cells can then be introduced in vivo via the administration routes described herein for therapeutic purposes.

Recombinant Expression Vectors and Host Cells

Another aspect of the invention pertains to vectors, preferably expression vectors, containing a nucleic acid encoding a PDX, Pax-4, NeuroD1 or MafA protein, or other pancreatic transcription factor, such as Ngn3, or derivatives, fragments, analogs, homologs or combinations thereof. In some embodiments, the expression vector comprises a single nucleic acid encoding any of the following transcription factors: PDX-1, Pax-4, NeuroD1, Ngn3, MafA, or Sox-9 or derivatives or fragments thereof. In some embodiments, the expression vector comprises two nucleic acids encoding any combination of the following transcription factors: PDX-1, Pax-4, NeuroD1, Ngn3, MafA, or Sox-9 or derivatives or fragments thereof. In a preferred embodiment, the expression vector contains nucleic acids encoding PDX-1 and NeuroD1.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, lentivirus, adenoviruses and adeno-associated viruses), which serve equivalent functions. Additionally, some viral vectors are capable of targeting a particular cells type either specifically or non-specifically.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PDX-1, Pax-4, MafA, NeuroD1 or Sox-9 proteins, or mutant forms or fusion proteins thereof, etc.).

For example, an expression vector comprises one nucleic acid encoding a transcription factor operably linked to a promoter. In expression vectors comprising two nucleic acids encoding transcription factors, each nucleic acid may be operably linked to a promoter. The promoter operably linked to each nucleic acid may be different or the same. Alternatively, the two nucleic acids may be operably linked to a single promoter. Promoters useful for the expression vectors of the invention can be any promoter known in the art. The ordinarily skilled artisan could readily determine suitable promoters for the host cell in which the nucleic acid is to be expressed, the level of expression of protein desired, or the timing of expression, etc. The promoter may be a constitutive promter, an inducible promoter, or a cell-type specific promoter.

The recombinant expression vectors of the invention can be designed for expression of PDX-1 in prokaryotic or eukaryotic cells. For example, PDX-1, Pax-4, MafA, NeuroD1, and/or Sox-9 can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of the invention can be carried out by standard DNA synthesis techniques.

In another embodiment, the PDX-1, Pax-4, MafA, NeuroD1, or Sox-9 expression vector is a yeast expression vector. Examples of vectors for expression in yeast *S. cerevisiae* include pYepSec1 (Baldari, et al., (1987) EMBO J 6:229-234), pMFa (Kujan and Herskowitz, (1982) Cell 30:933-943), pJRY88 (Schultz et al., (1987) Gene 54:113-123), pYES2 (Invitrogen Corporation, San Diego, Calif.), and picZ (InVitrogen Corp, San Diego, Calif.).

Alternatively, PDX-1, Pax-4, MafA, NeuroD1 or Sox-9 can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J 6: 187-195). When used in mammalian cells, the expression vectors control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev 1:268-277), lymphoid-specific promoters (Calame and Eaton (1988) Adv Immunol 43:235-275), in particular promoters of T cell receptors (Winoto and Baltimore (1989) EMBO J 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) PNAS 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) Science 249:374-379) and the alpha-fetoprotein promoter (Campes and Tilghman (1989) Genes Dev 3:537-546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to PDX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Additionally, host cells could be modulated once expressing PDX-1, Pax-4, MafA, NeuroD1 or Sox-9 or a combination thereof, and may either maintain or loose original characteristics.

A host cell can be any prokaryotic or eukaryotic cell. For example, PDX-1, Pax-4, MafA, NeuroD1 or Sox-9 protein can be expressed in bacterial cells such as *E. coli*, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector DNA can be introduced into prokaryotic or eukaryotic cells via conventional transformation, transduction, infection or transfection techniques. As used herein, the terms "transformation" "transduction", "infection" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. In addition transfection can be mediated by a transfection agent. By "transfection agent" is meant to include any compound that mediates incorporation of DNA in the host cell, e.g., liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

Transfection may be "stable" (i.e. integration of the foreign DNA into the host genome) or "transient" (i.e., DNA is episomally expressed in the host cells).

For stable transfection of mammalian cells, it is known that, depending upon the expression vector and transfection technique used, only a small fraction of cells may integrate the foreign DNA into their genome the remainder of the DNA remains episomal In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding PDX or can be introduced on a separate vector. Cells stably transfected with the introduced nucleic acid can be identified by drug selection (e.g., cells that have incorporated the selectable marker gene will survive, while the other cells die). In another embodiment the cells modulated by PDX or the transfected cells are identified by the induction of expression of an endogenous reporter gene. In a specific embodiment, the promoter is the insulin promoter driving the expression of green fluorescent protein (GFP).

In one embodiment the PDX-1, Pax-4, MafA, NeuroD1, or Sox-9 nucleic acid is present in a viral vector. In one embodiment, the PDX-1 and NeuroD1 nucleic acids are present in the same viral vector. In another embodiment the PDX-1, Pax-4, MafA, NeuroD1, or Sox-9 nucleic acid is encapsulated in a virus. In another embodiment, the PDX-1 and NeuroD1 is encapsulated in a virus (i.e., nucleic acids encoding PDX-1 and NeuroD1 are encapsulated in the same virus particle). In some embodiments the virus preferably infects pluripotent cells of various tissue type, e.g. hematopoietic stem, cells, neuronal stem cells, hepatic stem cells or embryonic stem cells, preferably the virus is hepatotropic. By "hepatotropic" it is meant that the virus has the capacity to preferably target the cells of the liver either specifically or non-specifically. In further embodiments the virus is a modulated hepatitis virus, SV-40, or Epstein-Bar virus. In yet another embodiment, the virus is an adenovirus.

Gene Therapy

In one aspect of the invention a nucleic acid or nucleic acids encoding a PDX-1, Pax-4, MafA, NeuroD1, or Sox-9 polypeptide or a combination thereof, or functional derivatives thereof, are administered by way of gene therapy. Gene therapy refers to therapy that is performed by the administration of a specific nucleic acid to a subject. In this aspect of the invention, the nucleic acid produces its encoded peptide(s), which then serve to exert a therapeutic effect by modulating function of an aforementioned disease or disorder. e.g., diabetes. Any of the methodologies relating to gene therapy available within the art may be used in the practice of the present invention. See e.g., Goldspiel, et al., 1993. Clin Pharm 12: 488-505.

In a preferred embodiment, the therapeutic comprises a nucleic acid that is part of an expression vector expressing any one or more of the aforementioned PDX-1, Pax-4, MafA, NeuroD1, and/or Sox-9 polypeptides, or fragments, derivatives or analogs thereof, within a suitable host. In a specific embodiment, such a nucleic acid possesses a promoter that is operably-linked to coding region(s) of a PDX-1, Pax-4, MafA, NeuroD1 and Sox-9 polypeptide. The promoter may be inducible or constitutive, and, optionally, tissue-specific. The promoter may be, e.g., viral or mammalian in origin. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. Proc Natl Acad Sci USA 86: 8932-8935. In yet another embodiment the nucleic acid that is delivered remains episomal and induces an endogenous and otherwise silent gene.

Delivery of the therapeutic nucleic acid into a patient may be either direct (i.e., the patient is directly exposed to the nucleic acid or nucleic acid-containing vector) or indirect (i.e., cells are first contacted with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, but not limited to, constructing said nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun.®. Biolistic, DuPont); coating said nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. J Biol Chem 262: 4429-4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the methodology of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, but not limited to: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. Meth Enzymol 217: 599-618. The chosen technique should provide for the stable transfer of the nucleic acid to the cell, such that the nucleic acid is expressible by the cell. Preferably, said transferred nucleic acid is heritable and expressible by the cell progeny. In an alternative embodiment, the transferred nucleic acid remains episomal and induces the expression of the otherwise silent endogenous nucleic acid.

In preferred embodiments of the present invention, the resulting recombinant cells may be delivered to a patient by various methods known within the art including, but not limited to, injection of epithelial cells (e.g., subcutaneously), application of recombinant skin cells as a skin graft onto the patient, and intravenous injection of recombinant blood cells (e.g., hematopoietic stem or progenitor cells) or liver cells. The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, Cell 71: 973-985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

DNA for gene therapy can be administered to patients parenterally, e.g., intravenously, subcutaneously, intramuscularly, and intraperitoneally. DNA or an inducing agent is administered in a pharmaceutically acceptable carrier, i.e., a biologically compatible vehicle which is suitable for administration to an animal e.g., physiological saline. A therapeutically effective amount is an amount which is capable of producing a medically desirable result, e.g., an increase of a pancreatic gene in a treated animal. Such an amount can be determined by one of ordinary skill in the art. As is well known in the medical arts, dosage for any given patient depends upon many factors, including the patient's size, body surface area, age, the particular compound to be administered, sex, time and route of administration, general health, and other drugs being administered concurrently. Dosages may vary, but a preferred dosage for intravenous administration of DNA is approximately $10^6$ to $10^{22}$ copies of the DNA molecule. For example the DNA is administers at approximately $2 \times 10^{12}$ virions per Kg.

Pharmaceutical Compositions

The compounds, e.g., PDX-1, Pax-4, MafA, NeuroD1, or Sox-9 polypeptides, nucleic acids encoding PDX-1, Pax-4, MafA, NeuroD1, or Sox-9 polypeptides, or a nucleic acid or compound that increases expression of a nucleic acid that encodes PDX-1, Pax-4, MafA, NeuroD1, or Sox-9 polypeptides (also referred to herein as "active compounds") of the invention, and derivatives, fragments, analogs and homologs thereof, can be incorporated into pharmaceutical compositions suitable for administration. Such compositions typically comprise the nucleic acid molecule, or protein, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL.™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The nucleic acid molecules of the invention can be inserted into vectors and used as gene therapy vectors. Gene therapy vectors can be delivered to a subject by any of a number of routes, e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

It should be understood that the present invention is not limited to the particular methodologies, protocols and reagents, and examples described herein. The terminology and examples used herein is for the purpose of describing particular embodiments only, for the intent and purpose of providing guidance to the skilled arisan, and is not intented to limit the scope of the present invention.

EXAMPLES

Example 1: General Methods

Human Liver Cells

Adult human liver tissues were obtained from individuals 3-23 years old or older. Liver tissues were used with the approval from the Committee on Clinical Investigations (the institutional review board). The isolation of human liver cells was performed as described (Sapir et al, 2005; Meivar-Levy et al, 2007). The cells were cultured in Dulbecco's minimal essential medium (1 g/l of glucose) supplemented with 10% fetal calf serum, 100 units/ml penicillin; 100 ng/ml streptomycin; 250 ng/ml amphotericin B (Biological Industries, Beit Haemek, Israel), and kept at 37° C. in a humidified atmosphere of 5% $CO_2$ and 95% air.

Viral Infection

The adenoviruses used in this study were as follows: Ad-CMV-Pdx-1 (Sapir et al, 2005; Meivar-Levy et al, 2007), Ad-RIP-luciferase (Seijffers et al, 1999), Ad-CMV-β-Gal, Ad-CMV-MafA (generous gift from Newgard, C. B., Duke University), Ad-CMV-Pax4-IRES-GFP (generous gift from St Onge, L. DeveloGen AG, Göttingen, Germany), and Ad-CMV-Isl1 (generous gift from Kieffer, T. University of British Columbia, Vancouver, Canada). The viral particles were generated by the standard protocol (He et al, 1998).

Liver cells were infected with recombinant adenoviruses for 5-6 days (Table 1) supplemented with EGF (20 ng/ml; Cytolab, Ltd., Israel) and nicotinamide (10 mM; Sigma). The optimal multiplicity of infection (MOI) was determined according to cell survival (<75%) and induction of c-peptide secretion. The MOI of the viruses used were; Ad-CMV-Pdx-1 (1000 MOI), Ad-CMV-Pax4-IRES-GFP (100 MOI), Ad-CMV-MAf-A (10 MOI) and Ad-CMV-Isl1 (100 MOI).

RNA Isolation, RT and RT-PCR Reactions

Total RNA was isolated and cDNA was prepared and amplified, as described previously (Ber et al, 2003; Sapir et al, 2005). Quantitative real-time RT-PCR was performed using ABI Step one plus sequence Detection system (*Applied Biosystems*, CA, USA), as described previously (Sapir et al, 2005; Meivar-Levy et al, 2007; Aviv et al, 2009).

C-Peptide and Insulin Secretion Detection

C-peptide and insulin secretion were measured by static incubations of primary cultures of adult liver cells 6 days after the initial exposure to the viral treatment, as described (Sapir et al, 2005; Meivar-Levy et al, 2007; Aviv et al, 2009). The glucose-regulated c-peptide secretion was measured at 2 mM and 17.5 mM glucose, which was determined by dose-dependent analyses to maximally induce insulin secretion from transdifferentiated liver cells, without having adverse effects on treated cells function (Sapir et al, 2005; Meivar-Levy et al, 2007; Aviv et al, 2009). C-peptide secretion was detected by radioimmunoassay using the human C-peptide radioimmunoassay kit (Linco Research, St. Charles, Mo.; <4% cross-reactivity to human proinsulin). Insulin secretion was detected by radioimmunoassay using human insulin radioimmunoassay kit (DPC, Angeles, Calif.; 32% cross-reactivity to human proinsulin). The secretion was normalized to the total cellular protein measured by a Bio-Rad protein assay kit.

Luciferase Assay

Human liver cells were co-infected with Ad-RIP-luciferase (200 moi) and the various adenoviruses (as described below). Six days later, luciferase activity was measured using the Luciferase assay System (Promega) and the LKB 1250 Luminometer (LKB, Finland). The results were normalized to total cellular protein measured by the Bio-Rad Protein Assay kit (Bio-Rad).

Immunofluorescence

Human liver cells treated with the various adenoviruses, were plated on glass cover slides in 12-well culture plates ($2 \times 10^5$ cells/well). 3-4 days later, the cells were fixed and stained as described (Sapir et al, 2005; Meivar-Levy et al, 2007; Aviv et al, 2009). The antibodies used in this study were: anti-rabbit PDX-1, anti-goat PDX-1 (both 1:1000 a generous gift from C. V. E. Wright), anti-human insulin, anti-human somatostatin (both 1:100, Dako, Glostrup, Denmark), anti-Pax4 (1:100; R&D Systems, Minneapolis, Minn.), anti-MafA (1:160; Santa Cruz Biotechnology, Inc., Santa Cruz, Calif.). The secondary antibodies used were: anti-rabbit IgG Cyanine (cy2) conjugated antibody 1:250, anti-rabbit IgG indocarbocyanine (cy3) conjugated antibody 1:250, anti-goat IgG Cyanine (cy2) conjugated antibody 1:200, anti-goat IgG indocarbocyanine (cy3) conjugated antibody 1:250, and anti-mouse IgG indocarbocyanine (cy3) conjugated antibody 1:250 (all from Jackson ImmunoResearch, PA). Finally, the cells were stained with 4',6-diamidino-2-phenyl-indole (DAPI, Sigma). The slides were imaged and analyzed using a fluorescent microscope (Provis, Olympus).

Statistical Analysis

Statistical analyses were performed with a 2-sample Student t-test assuming unequal variances.

Example 2: Pdx-1-Induced Transdifferentiation

Previous studies (Sapir et al, 2005; Meivar-Levy et al, 2007; Aviv et al, 2009; Gefen-Halevi et al, 2010; Meivar-Levy et al, 2011) have suggested that Pdx-1 alone is capable of inducing β-cell like phenotype and function in human liver cells, possibly due to its capacity to activate numerous otherwise silent endogenous pTFs in liver. The activation of the pancreatic lineage was fast and occurred within 5 days (Sapir et al, 2005, Ber et al, 2003)

In this example, the sequence of events that mediate Pdx-1 induced liver to pancreas transdifferentiation is examined. Adenoviral vectors encoding Pdx-1 were introduced to adult human liver cells, and the effects of ectopic Pdx-1 expression were monitored for four consecutive days post infection (Days 2-5; FIG. 1). Pancreatic hormone and pancreas-specific transcription factor expression was determined by quantitative RT-PCR analysis every day for 5 days. Results were normalized to □-actin gene expression within the same cDNA sample and are presented as the mean±SE of the relative expression versus control virus (Ad-CMV-β-gal, 1000 MOI) treated cells on the same day. Two independent experiments were performed, with n≥4, *p<0.05 and **p<0.01.

Both glucagon and somatostatin genes were immediately activated, within one day after Ad-Pdx-1 infection (FIGS. 1C and 1D). However, insulin expression was only detected on the fourth to fifth day post-infection (FIG. 1A). To provide a mechanistic explanation for the distinct temporal activation of the three major pancreatic hormones, expression levels of endogenously activated transcription factors were analyzed during the transdifferentiation process. The early pancreatic endocrine transcription factors, NGN3 and NEUROD1 were immediately activated. However, β-cell specific TFs, such as NKX6.1 and MafA, were only gradually and modestly activated in response to ectopic Pdx-1 expression, reaching their peak expression level on the fourth and fifth day, respectively. The activation of insulin gene expression on the fifth day was associated not only with an increase in MafA expression but also with a decrease in Isl1 expression (FIG. 1D). These data suggest that transdifferentiation of human liver cells along the pancreatic lineage, despite being rapid, is a gradual and consecutive process. The distinct temporal activation of pancreatic hormone gene expression (such as somatostatin and glucagon) can be partially attributed to the time course and the relative levels of the endogenously activated pTFs expression.

Example 3: Combined Expression of Pdx-1, Pax4 and Mafa Increases the Efficiency of Liver to Pancreas Transdifferentiation Previous studies have suggested that the concerted expression of several pTFs increases the transdifferentiation efficiency along the β-cell lineage, compared to that induced by individual pTFs (Kaneto et al, 2005; Tang et al, 2006; Song et al, 2007; Wang et al, 2007; Gefen-Halevi et al, 2010), as well as along other lineages. In order to analyze this notion in the experimental system of primary adult human liver cell cultures described herein, the individual and joint contribution of three major pTFs on liver to pancreas transdifferentiation were investigated. Pdx-1, Pax4 and MafA, which mediate different stages in pancreas organogenesis, were ectopically co-expressed in primary cultures of adult human liver cells using recombinant adenoviruses. Cultured adult human liver cells were infected with Ad-CMV-Pdx-1 (1000 MOI), Ad-CMV-Pax-4 (100 MOI) and Ad-CMV-MafA (10 MOI) alone or in concert or with control virus (Ad-CMV-β-gal, 1000 MOI), and pancreatic differentiation markers were examined six days later. The multiplicity of infection (MOI) of each factor was titrated to result in maximal reprogramming efficiency associated by minimal adverse effects on infected cell viability. Pdx-1 was expressed in 70% of the cells in culture, and the joint co-expression of all 3 pTFs was evident in 46.8% of the Pdx-1 positive cells (FIG. 2A). Very few cells stained positive only to Pax-4 or to MafA. Cells that stained positive for all three pTFs are indicated by the arrows (FIG. 2A, right panel). In FIG. 2B, liver cells were co-infected with the combined pTFs and with Ad-RIP-LUC (200 moi), and Luciferase activity of the insulin promoter was measured.

The combined expression of the three pTFs resulted in a substantial increase in insulin promoter activation (FIG. 2B), a three-fold increase in the number of (pro)insulin producing cells (FIG. 2C) and 30-60% increase in glucose regulated (pro)insulin secretion (FIG. 2D), compared to that induced by each of the pTFs alone. Taken together, these results suggest that the combination of the 3 pTFs increase transdifferentiation efficiency and also indicate that each of the factors is limited in its capacity or is insufficient to individually promote maximal transdifferentiation (Kaneto et al, 2005; Tang et al, 2006; Zhou et al, 2008).

Figure 2:
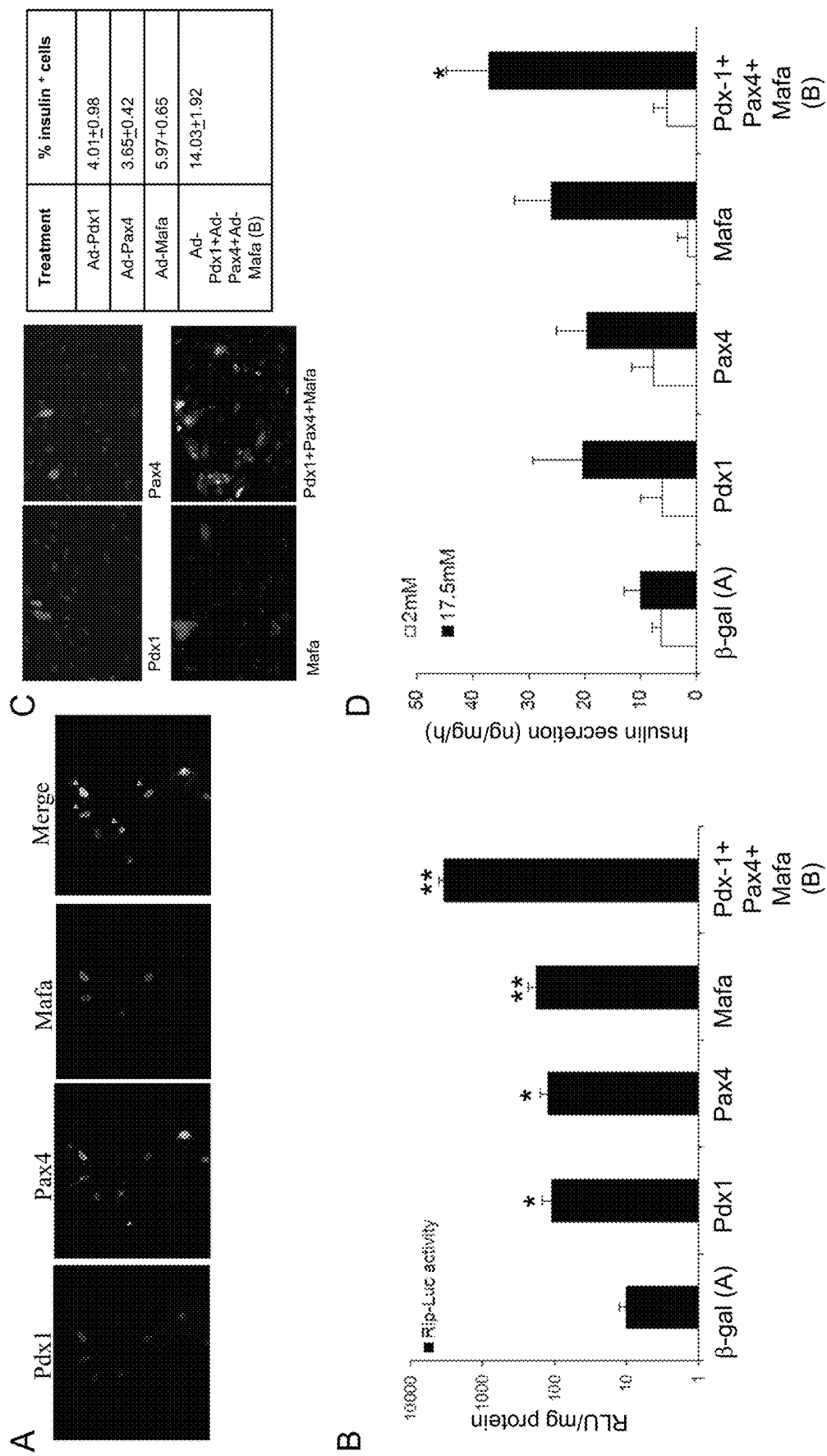
FIGS. 2A-2D shows that ectopic co-expression of pancreatic transcription factors (pTFs) Pdx-1, Pax4, and MafA in human liver cells in vitro promotes (pro)insulin secretion, compared to that induced by each of the pTFs alone.

Example 4: Maturation and Segregation into the Different Hormones Producing Cells of Transdifferentiated Cells is Temporally Controlled in an Hierarchical Manner In this example, the impact of temporally controlling the ectopic pTFs expression was investigated to determine whether increased transdifferentiation efficiency by combined ectopic expression of the three pTFs is also temporally controlled as suggested above (FIG. 2). In support of temporal control having a role in pancreas transdifferentiation, it is known that the three pTFs Pdx-1, Pax4, and MafA display distinct temporal expression and function during pancreas organogenesis.

The three pTFs Pdx-1, Pax4, and MafA were introduced sequentially or in concert to primary cultures of adult human liver cells using recombinant adenoviruses. Adenovirus-mediated ectopic gene expression peaks 17 hours post infection (Varda-Bloom et al, 2001). Therefore, the pTFs were sequentially administered during three consecutive days (see Viral infection in Example 1), allowing the manifestation of their individual effects. Cells were infected according to the schedule as displayed in Table 1.

TABLE 1

| Treatment order | Day 1 | Day 2 | Day 3 | Day 4 | Day 5 | Day 6 |
|---|---|---|---|---|---|---|
| A | Ad-β-gal (control) | | | | | Harvest |
| B | Ad-Pdx-1 + Ad-Pax4 + Ad-MafA | | | | | Harvest |
| C | Ad-Pdx-1 | Ad-Pax4 | Ad-Mafa | | | Harvest |
| D | Ad-Mafa | Ad-Pax4 | Ad-Pdx-1 | | | Harvest |
| E | Ad-Pdx1 | Ad-Mafa | Ad-Pax4 | | | Harvest |

Cells were sequentially infected with one pTF adenoviral construct per day over three days in three different sequences: a direct hierarchical order (treatment C=Pdx-1→Pax4→MafA), in an opposite order (treatment D=MafA→Pax4→Pdx-1), and in a random order (treatment E=Pdx-1→MafA→Pax4). The effect of the sequential pTFs administration on transdifferentiation efficiency and on the β-cell-like maturation was compared to that of the concerted or simultaneous administration of all three pTFs on the first day (treatment B=Pdx-1+Pax4+MafA) and to similar MOI of control virus (treatment A=β-gal) (Table 1 and FIG. 3A). Specifically, cultured adult human liver cells were infected with Ad-CMV-Pdx-1 (1000 MOI), Ad-CMV-Pax-4 (100 MOI) and Ad-CMV-MafA (10 MOI) together or in a sequential manner as summarized in FIG. 3A and Table 1 (treatments B-E) or with control virus (Ad-CMV-β-gal, 1000 moi, treatment A), and analyzed for their pancreatic differentiation six days later.

Insulin promoter activity (FIG. 4A), the percent of insulin producing cells (FIG. 3B) and glucose-regulated (pro)insulin secretion (FIG. 3C) were unaffected by the order of the sequentially administered pTFs. Interestingly, the sequential pTF administration in the random order (treatment E=Pdx-1→MafA→Pax4) resulted in increased insulin promoter activity but was associated with loss of glucose regulation of insulin secretion and decreased glucose transporter 2 (GLUT-2) expression (FIGS. 3B, 3C and 4B). Loss of glucose sensing ability upon changing the order of Pax4 and MafA administration suggests a potential effect of the sequence of expressed pTFs on β-cell-like maturation but not on the efficiency of the transdifferentiation process.

Example 5: Hierarchical Administration of PDX-1, PAX4, and Mafa Promotes the Maturation of Transdifferentiated Cells to β-Like Cells The previous results encouraged further investigation to determine to what extent and under which conditions increased transdifferentiation efficiency is associated with enhanced maturation along the β-cell lineage. The hallmark characteristics of mature β-cells are the capacity to process the proinsulin and secrete it in a glucose-regulated manner (Eberhard et al, 2009; Borowiak, 2010). To analyze whether the temporal changes in pTF expression distinctly affect transdifferentiated cell maturation along the β-cell lineage, the effect of the distinct treatments A-E (Table 1 and FIG. 3A) on proinsulin processing and glucose-regulated c-peptide secretion was analyzed.

Figure 5:
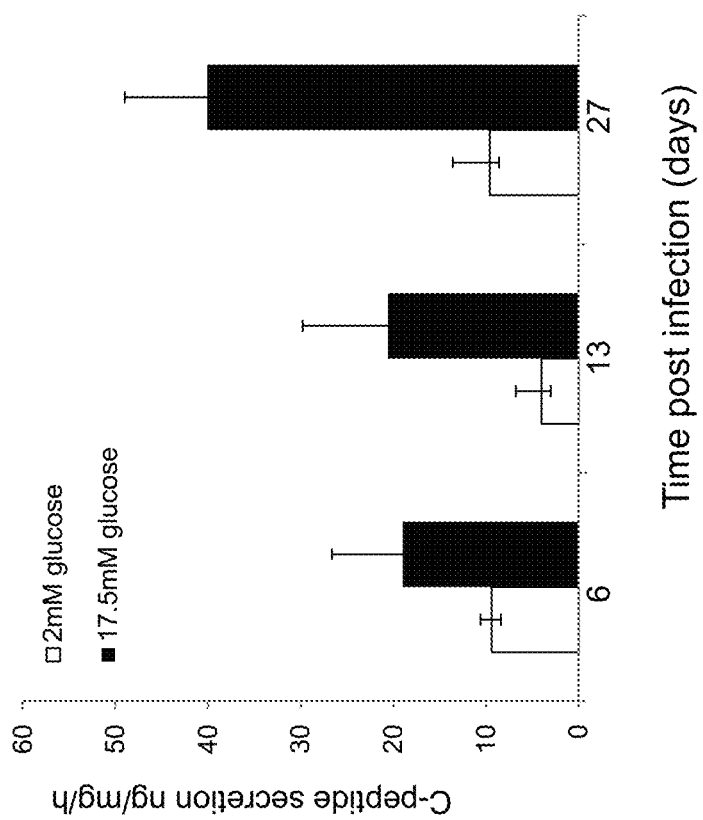
FIGS. 5A-5B shows two graphs demonstrating c-peptide secretion after hierarchical sequential order of infection (treatment C).
Figure 5:
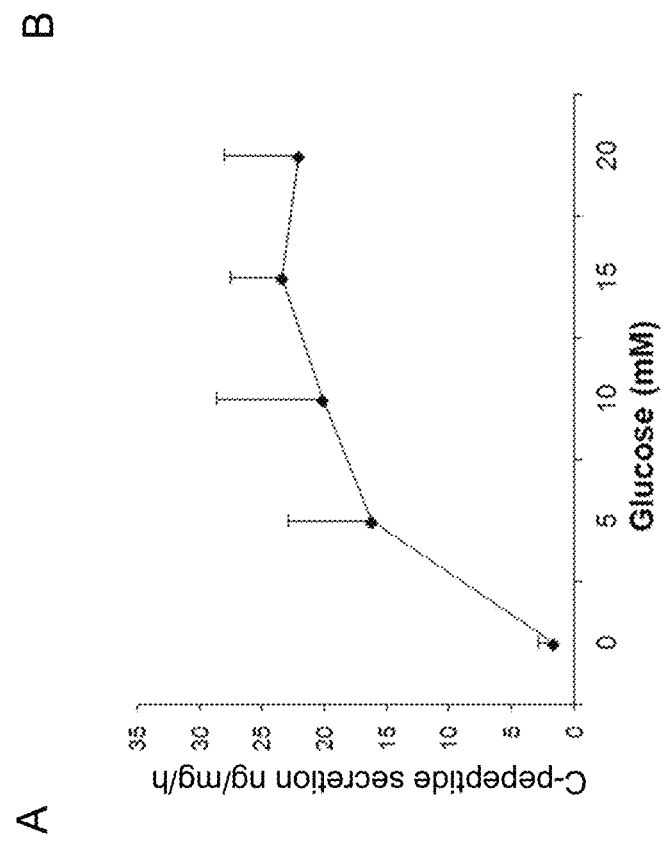

Indeed, only the direct hierarchical administration (treatment C) of the pTFs resulted in pronounced production of processed insulin and its glucose-regulated secretion which displayed physiological glucose dose response characteristics (FIGS. 3C and 5A). The newly acquired phenotype and function were stable, as demonstrated by the ability to secrete c-peptide in a glucose-regulated manner for up to four weeks in vitro (FIGS. 5A and 5B).

Figure 3:
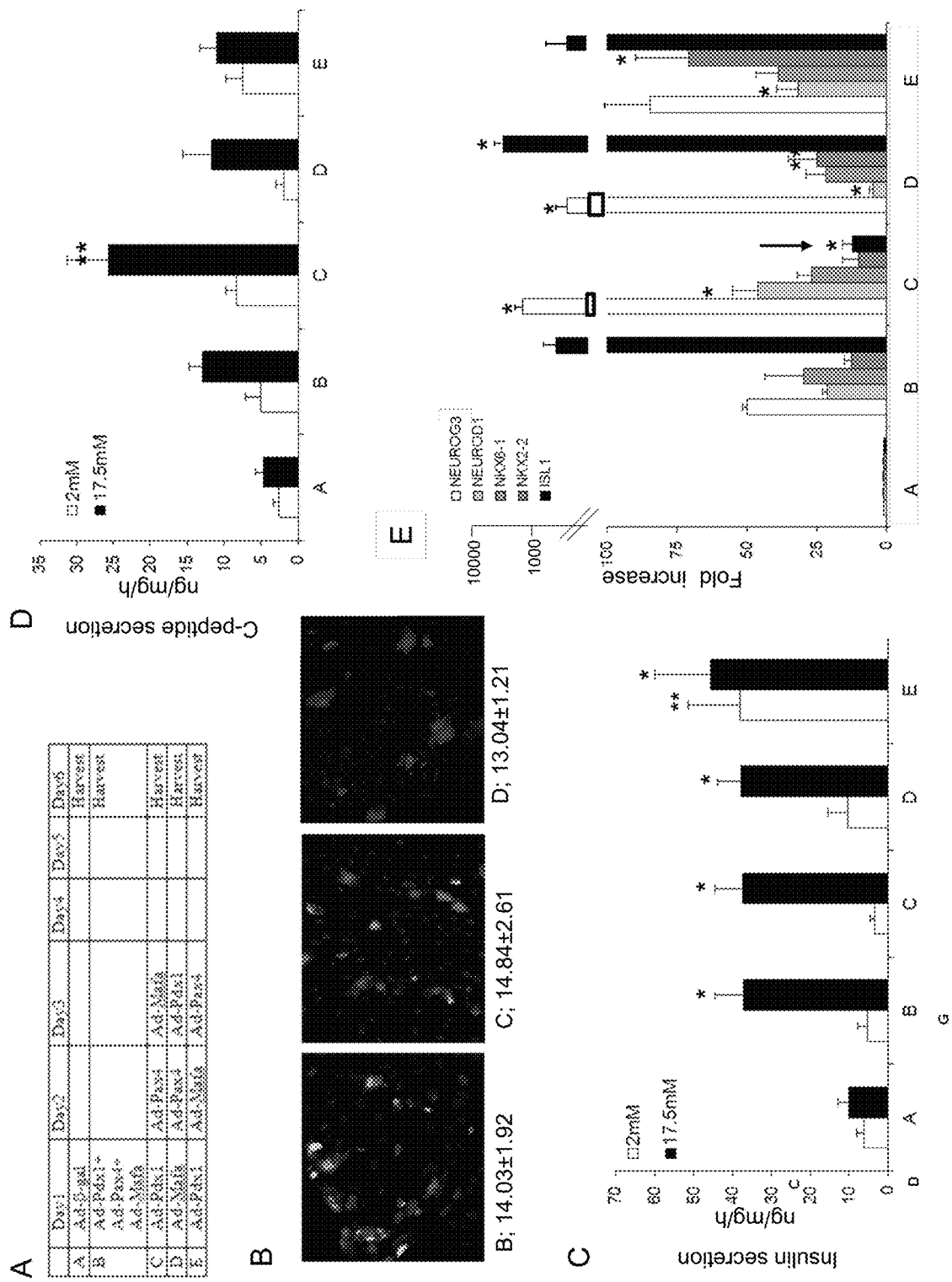
FIGS. 3A-3E shows the effects of concerted and sequential expression of pTFs Pdx-1, Pax4, and MafA on pancreatic β-cell maturation.
Figure 4:
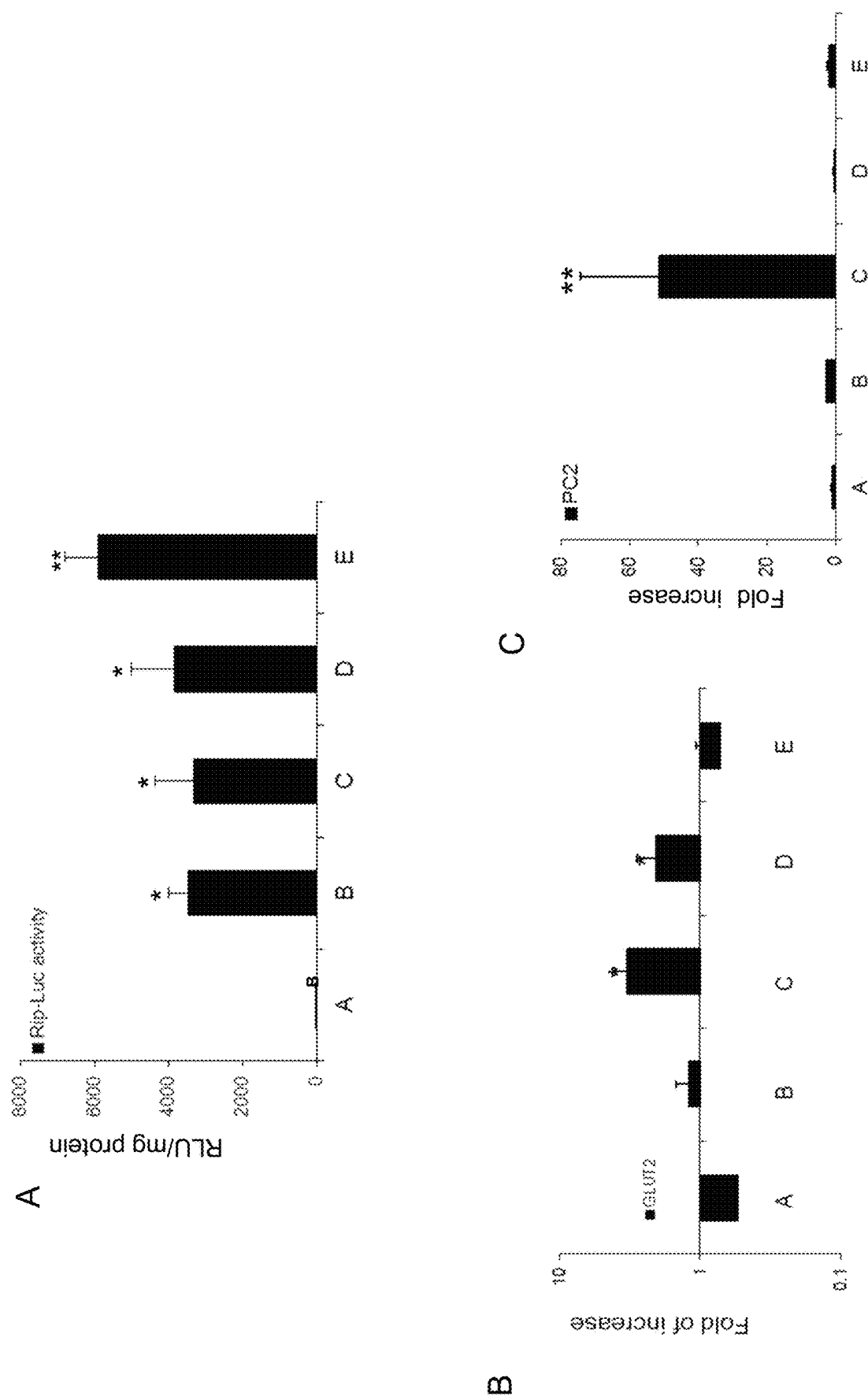
FIGS. 4A-4C shows three graphs demonstrating transdifferentiation efficiency, indicating hierarchical sequential order of infection (treatment C) is most efficient.

The increased prohormone processing only upon the direct hierarchical pTFs administration (treatment C) was associated with pronounced increase in PCSK2 and GLUT2 gene expression, which possess roles in prohormone processing and glucose sensing abilities, respectively (FIGS. 3 and 4). These data suggest an obligatory role for the sequential and direct hierarchical expression of pTFs in promoting the maturation and function of the transdifferentiated liver cells along the β-cell lineage. Both concerted (treatment B) and sequential TF administration in an indirect hierarchical mode (treatment D and E), failed to generate transdifferentiated cells which display mature β-cell-like characteristics.

To provide a mechanistic explanation for the changes in the β-cell-like state of maturation the repertoire of the endogenously activated pTFs under the distinct temporal treatments (B-E) was analyzed. All the treatments (B-E) resulted in increased expression of numerous endogenous pTFs (FIG. 3E), such as NEUROG3, NEUROD1, NKX6.1 and NKX2.2. However, the most robust difference between the "mature" (treatment C) and "immature" phenotypes (treatments B, E and D) was exhibited at the levels of the endogenous Isl1 gene expression. Thus, the most enhanced maturation along the β-cell lineage induced by direct hierarchical pTFs administration (treatment C) correlates with a dramatic decrease in endogenous Isl1 expression (FIG. 3E, arrow). Taken together these data suggest that the maturation of transdifferentiated cells to β cells could be affected by the relative and temporal expression levels of specific pTFs.

Figure 8:
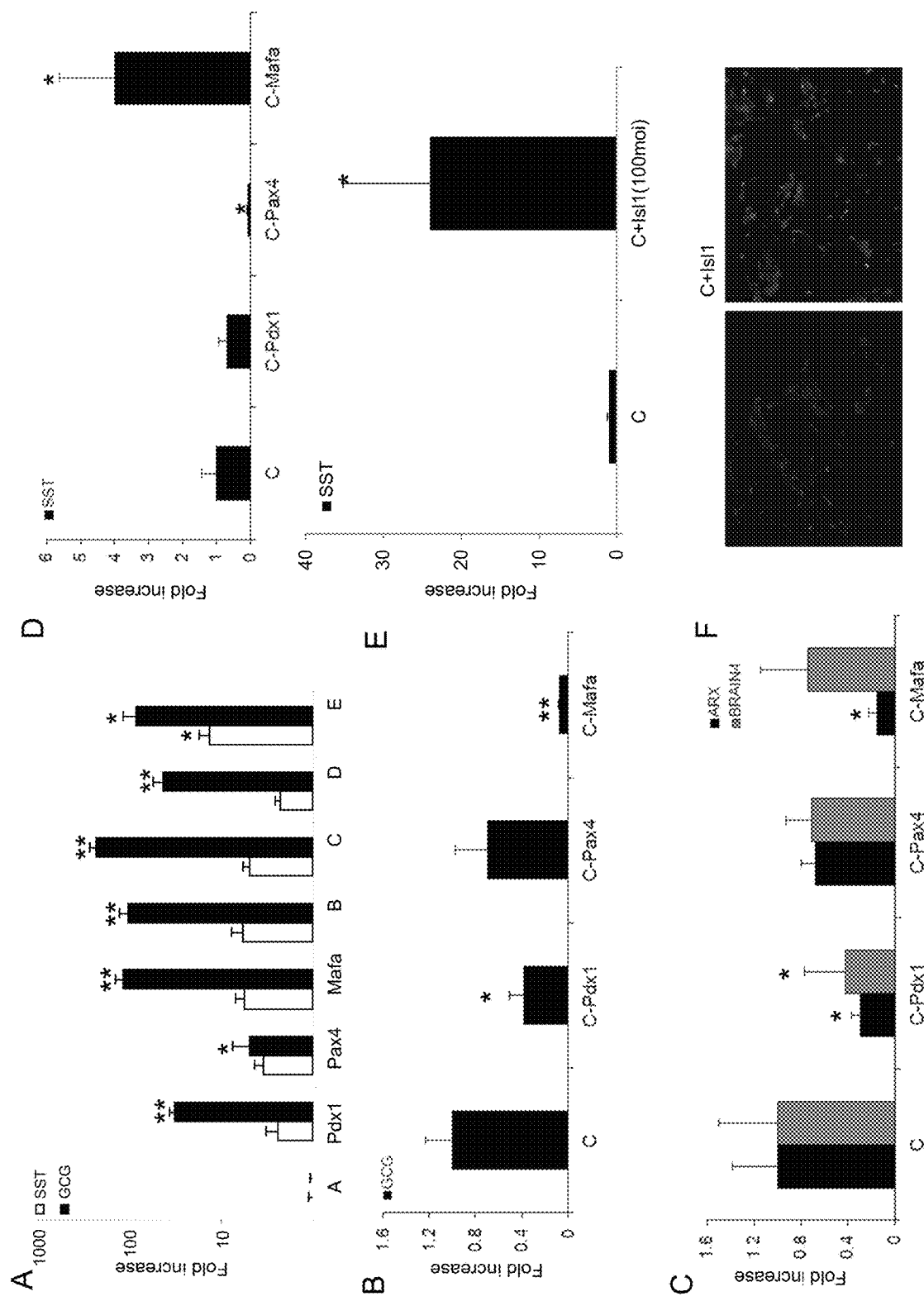
FIGS. 8A-8G shows the individual role of pTFs in promoting the differentiation of cells to produce glucagon (α) and somatostatin (δ) using hierarchical order of infection (treatment C) and exclusion of each pTF. Expression levels of pancreatic hormones glucagon (GCG) (FIGS. 8A and 8B) and somatostatin (SST) (FIGS. 8A and 8D) was determined by RT-PCR after the indicated infection treatments.

Example 6: Hierarchical Administration of PDX-1, Pax4, and Mafa Promotes the Segregation of Transdifferentiated Cells Between β-Like and δ-Like Cells Exclusion of MafA from treatment C (Table 1) induced both Isl-1 (FIG. 6D) and somatostatin gene expression (FIG. 8D). To analyze whether Isl-1 increased expression upon MafA exclusion indeed causes increased Somatostatin gene expression, Ad-CMV-Isl-1 was added together with MafA on the $3^{rd}$ day (treatment C, in table 1). Indeed, Isl-1 increased somatostatin gene expression (FIG. 6E). Ectopic Isl-1 expression (C+Isl-1) caused also increased Somatostatin protein production (FIG. 6F) and its co-production in insulin producing cells (FIG. 9 lower panel), suggesting that high MafA expression associated by low Isl-1 expression is crucial for segregating between insulin and somatostatin producing cells.

Example 7: Analysis of the Individual Contribution of PDX-1, PAX4, and Mafa to Liver to Pancreas Transdifferentiation The sequential characteristics of the transdifferentiation process were identified by temporal gain of function studies. Further analysis of the separate contribution of each of the transcription factors, Pdx-1, Pax4 and MafA, to the hierarchical developmental process was performed by a relative and temporal "reduced function" approach. Adult human liver cells were treated by the direct temporal and sequential reprogramming protocol (treatment C), from which one of the ectopic pTFs was omitted. The omitted pTF was replaced by a control adenovirus carrying β-gal expression at a similar multiplicity of infection. Specifically, adult human liver cells were treated by the direct "hierarchical" sequential infection order (treatment C, FIG. 3A and Table 1). One single transcription factor (pTF) was omitted at a time and replaced by identical moi of Ad-CMV-β-gal. Pdx-1 omission is indicated as (C-Pdx-1), Pax4 omission is indicated as (C-Pax4), and MafA omission is indicated as (C-MafA).

Figure 6:
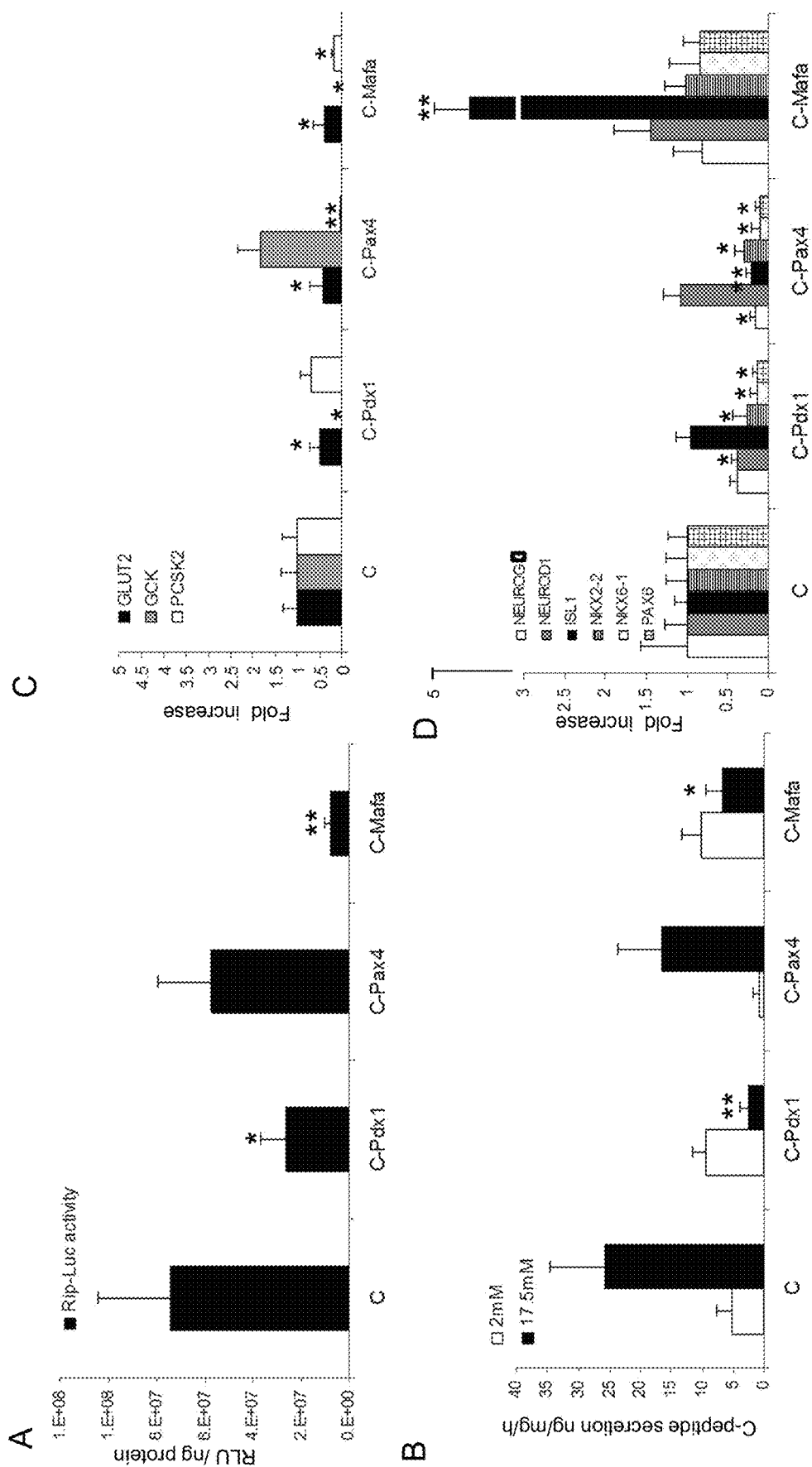
FIGS. 6A-6D is four graphs showing the individual role of the pTFs in the transdifferentiation process, using treatment C infection order and exclusion of each pTF (C-Pdx1, exclusion of Pdx1; C-Pax4, exclusion of Pax4; and C-Mafa, exclusion of Mafa).

The functional consequences of separately omitting each of the pTFs' expression were analyzed at the molecular and functional levels (FIG. 6). Separate Pdx-1 and MafA omission (C-Pdx-1 and C-MafA, respectively) resulted in decreased insulin promoter activation (FIG. 6A), ablated glucose response of processed insulin secretion (FIG. 6B) and decreased GLUT2 and GK expression (FIG. 6C). Exclusion of MafA associated also with decreased expression of the prohormone convertase, PCSK2 (FIG. 6C). On the other hand, exclusion of Pax4 (C-Pax4) did not significantly affect insulin promoter activation, nor did it affect glucose-regulated c-peptide secretion. Pax-4 omission was associated with decreased GLUT2 and PCSK2 expression (FIG. 6C), possibly suggesting that the expression of GK is sufficient for obtaining glucose control ability of the hormone secretion.

Analysis of the consequences of the temporal and separate pTF exclusion on the repertoire of the endogenously activated pTF expression was performed to explain these developmental alterations. Pdx-1 and Pax4 exclusion caused a marked decline in the expression of most other pTFs (including NeuroG3, NKX2.2, NKX6.2, and Pax6), suggesting that their potential contribution to increasing transdifferentiation efficiency is related to their capacity to activate endogenous pancreatic TFs (FIG. 6D). On the other hand, exclusion of MafA did not contribute to further activation of endogenous pTF expression, possibly reflecting its late and restricted expression only in pancreatic β-cells. On the contrary, MafA contribution to increased insulin promoter activity, prohormone processing and its glucose regulated secretion was associated only with decreased Isl-1 expression (FIG. 6D). These data may suggest that MafA is not involved in further promoting the efficiency of endogenous pTFs expression and liver to pancreas transdifferentiation, but rather in promoting transdifferentiated cell maturation.

Example 8: ISL-1 Prevents Maturation of Transdifferentiated Cells to β Cell Lineage The effect of MafA on β-cell-like maturation may in part be associated with its capacity to repress Isl1 expression. To test this hypothesis, ectopic Isl1 was introduced by adenoviral infection (Ad-Isl1) in transdifferentiated cells. Briefly, adult human liver cells were treated by the direct "hierarchical" sequential infection order (treatment C) and supplemented by Ad-Isl1 (1 or 100 MOI) at the $3^{rd}$ day (C+Isl1).

Figure 7:
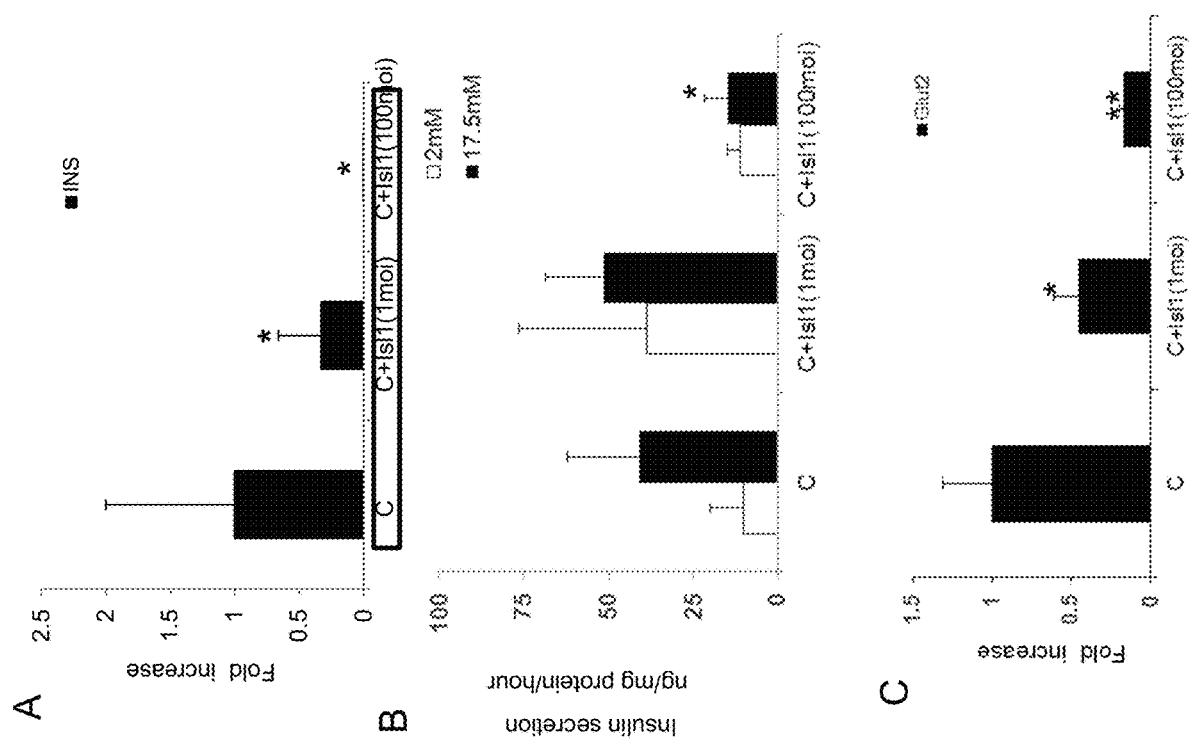
FIGS. 7A-7C shows three graphs showing the effects of Isl1 expression on β-cell maturation of transdifferentiated liver cells after infection by "hierarchical" sequential order (treatment C).

As indicated above, the sequential administration of the three pTFs in a direct hierarchical manner (treatment C) resulted in both increased transdifferentiation efficiency and the maturation of the newly generated cells along the β cell lineage. Isl1 was jointly administered with MafA on the third day (C+Isl1). Indeed, Isl1 overexpression on the third day, under the control of a heterologous promoter, resulted in substantial decrease of insulin gene expression and ablation of glucose regulated (pro)insulin secretion (FIG. 7). The loss of glucose-sensing ability was associated with diminished GLUT2 expression (FIG. 7C). These results suggest that deregulated Isl1 expression at the final stages of the transdifferentiation protocol potentially hampers the maturation along the β cell lineage, and may account in part for the ablated maturation under low MafA expression.

Taken together, these data suggest a crucial obligatory role for direct hierarchical expression of pTFs in promoting transdifferentiated liver cell maturation along the β cell lineage. Moreover, the sequential developmental process is associated with both activation and repression of pTFs that may promote or hamper transdifferentiated cell maturation along the pancreatic β cell lineage.

Example 9: PDX-1, PAX4 and Mafa Hierarchical Administration Induces Glucagon and Somatostatin Expression Transdifferentiation along the endocrine pancreatic lineage results in the activation of expression of numerous pancreatic hormones. The extent with which these hormone expression levels are affected by the temporal manipulation of the pTFs was also investigated. Gene expression of pancreatic hormones glucagon (GCG) (FIGS. 8A and 8B), somatostatin (SST) (FIGS. 8A, 8D, and 8E) or a cells specific transcription factors (FIG. 8C) were determined by quantitative real-time PCR analysis after the indicated treatments.

The transcription of both glucagon (GCG) and somatostatin (SST) genes was induced by each of the individually expressed pTFs, mainly by Pdx-1 and MafA and to a lower extent by Pax4 (FIG. 8A). A further increase in glucagon gene transcription occurred only upon the direct hierarchical administration of pTFs (FIG. 4A, see treatment C). Pdx-1 and MafA exerted their effects on glucagon expression in a process associated with the activation of the α-cell specific transcription factors ARX and BRAIN4 or ARX alone, respectively (FIG. 8C). Somatostatin gene expression which remained unaffected by most treatments (FIGS. 8A and 8D), was increased when the temporal protocol was concluded by ectopic Pax4 expression (E=Pdx-1→MafA→Pax4). This sequential protocol also exhibited a deteriorative effect on glucose-regulated (pro)insulin secretion and was associated by increased Isl1 endogenous expression (FIGS. 3C and E). The ablated maturation along the β cell lineage was associated with increased somatostatin gene expression and an increased number of somatostatin positive cells (FIG. 8F). Many of the cells exhibited somatostatin and insulin co-localization (data not shown).

Exclusion of each pTF from the hierarchical administration (treatment C) as discussed in Example 6 was also utilized to further investigate the role of the individual pTFs in glucagon and somatostatin expression (FIGS. 8B and 8D). Pax4 exclusion substantially reduced somatostatin gene expression, suggesting its potential role in inducing the transcription of this gene (FIG. 8D). Interestingly, MafA exclusion at the end of the developmental process also substantially increased somatostatin gene expression, suggesting a potential inhibitory effect of MafA on somatostatin gene expression. This effect could be also attributed to MafA's capacity to repress Isl1 expression. To address this hypothesis, the effect of ectopic Isl1 on somatostatin gene expression was analyzed. Indeed, Ad-Isl1 administration on the third day together with MafA (C+Isl1) increased somatostatin gene expression (FIG. 8E), while decreasing insulin gene expression, hormone production and secretion (FIGS. 8A, 8B and FIG. 7). Under these experimental conditions, 40% of the insulin producing cells stained positive for somatostatin with very few cells expressing somatostatin alone.

These results suggest that part of the maturation of transdifferentiated cells to β-cells is attributed to MafA expression at the late stages of the transdifferentiation process. At this stage, MafA restricts somatostatin expression in a process associated with its capacity to inhibit Isl1 expression.

Figure 9:
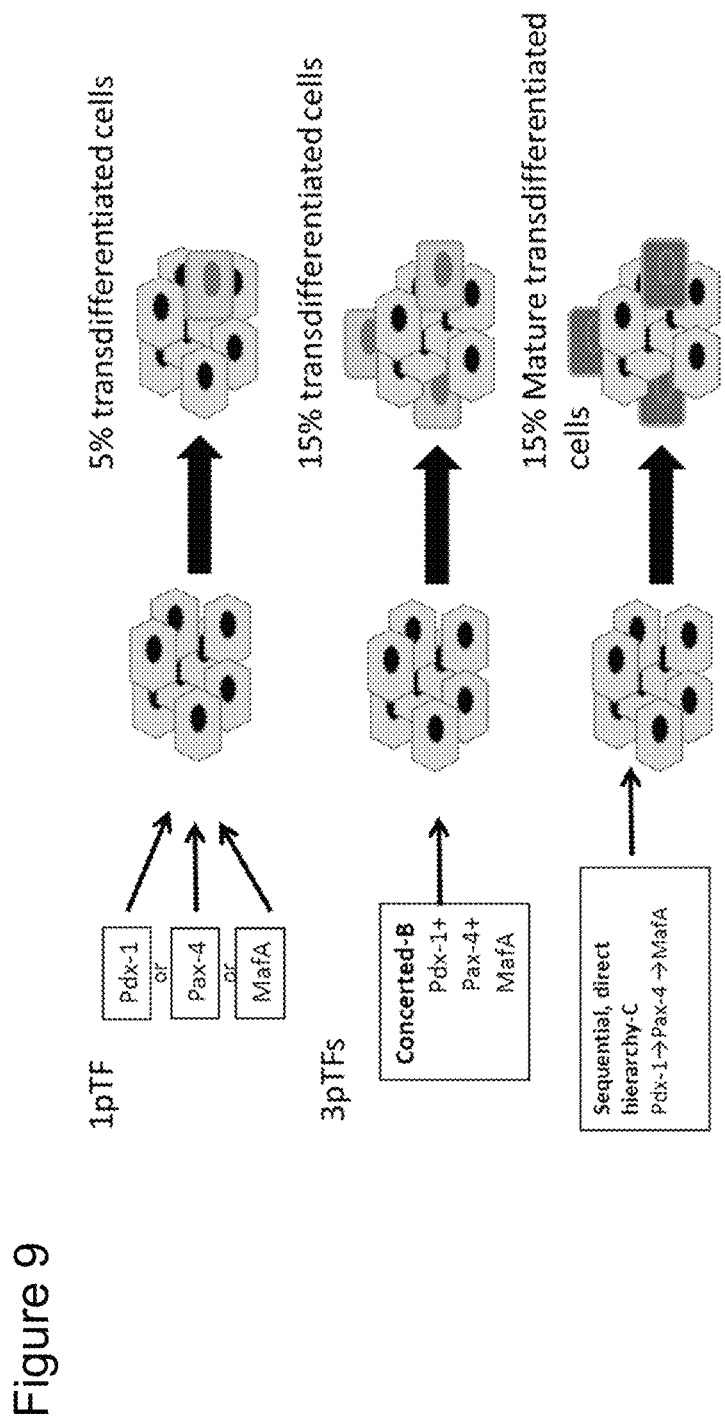
FIG. 9 shows a schematic representation of the proposed mechanism of pancreatic transcription factor-induced transdifferentiation from liver to pancreas. The concerted expression of the three pTFs results in increased number of transdifferentiated liver cells compared to each of the factor's individual effect (B). The sequential administration of transcription factors in a direct hierarchical manner results in increased maturation of the Transdifferentiated cells along the beta-like-pancreatic lineage FIG. 10. Pdx-1-induced IPCs' activation in mice in vivo is restricted to cells adjacent to the central veins which are characterized by GS expression. Immunohistochemical analysis of Pdx-1 (FIG. 10A) and insulin (FIG. 10B) 14 days after Ad-CMV-PDX-1 administration. Arrows indicate positive cells, mostly located at the proximity of central veins (cv).

FIG. 9 shows the proposed mechanism of pancreatic transcription factor induced liver to pancreas transdifferentiation. Each of the pTFs is capable of activating a modest β-cell-like phenotype, in a restricted number of human liver cells. The concerted expression of the pTFs markedly increases liver to endocrine pancreas transdifferentiation. However the newly generated cells are immature and coexpress both insulin and somatostatin. Only sequential administration of the same factors in a direct hierarchical manner both increases transdifferentiation efficiency and also the transdifferentiated cell maturation along the β-cell lineage.

Figure 10:
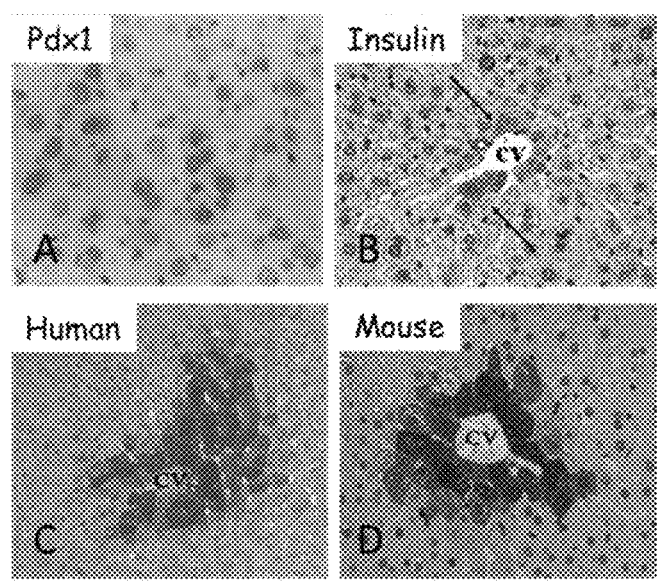
(FIG. 10C & FIG. 10D) analysis of GS expression in human (FIG. 10C) and mice (FIG. 10D) livers indicating the expression of GS at the 1-2 cell layers adjacent to the central veins. Original magnification ×.400

Example 10: Identification of Cell Populations with Transdifferentiation Capacity In Vivo Cell populations with transdifferentiation capacity were identified in vivo in mice. Ectopic expression of the Pdx-1 gene was achieved in mice livers. Despite the uniform expression of the ectopic Pdx-1 gene in about 40-50% of the cells of the liver (FIG. 10A) (Ferber et al., Nat Med. 2000, and Ber et al., JBC, 2003) insulin-producing cells (IPCs) in Pdx-1-treated mice in vivo were primarily located close to central veins (FIG. 10B), which is characterized by active Wnt signaling and the expression of glutamine synthetase (GS) (FIG. 1C). The co-localization of GS expression and insulin activation by Pdx-1 also indicated that those cells that can activate the GSRE have a predisposition for increased transdifferentiation capacity. Therefore, cell populations predisposed for transdifferentiation can also be identified by GSRE activation and active Wnt-signaling pathway.

Example 10: Using Adenoviruses to Identify Human Liver Cells Predisposed for Transdifferentiation This example demonstrates the use of recombinant adenoviruses to identify human liver cells that are predisposed for transdifferentiation. Human liver cells in culture are heterogeneous with regard to the activation of the intracellular Wnt signaling pathway and expression of GS. As GS is uniquely expressed in pericentral liver cells, therefore the capacity to activate GSRE (GS Regulatory Element) can be used as a selective parameter of isolation of relevant cells (Gebhardt et al., Prog Histochem Cytochem, 2007; Gebhardt et al., Methods Mol Biol, 1998; and Gaunitz et al., Hepatology, 2005).

In addition as the GSRE contains also a STAT5 binding element, the predisposition of the cells to transdifferentiation could be mediated by this element. The STAT5 pathway could also be involved in endowing the cells with reprogramming or transdifferentiation predisposition (FIGS. 10, 11, 14 and 19).

Figure 11:
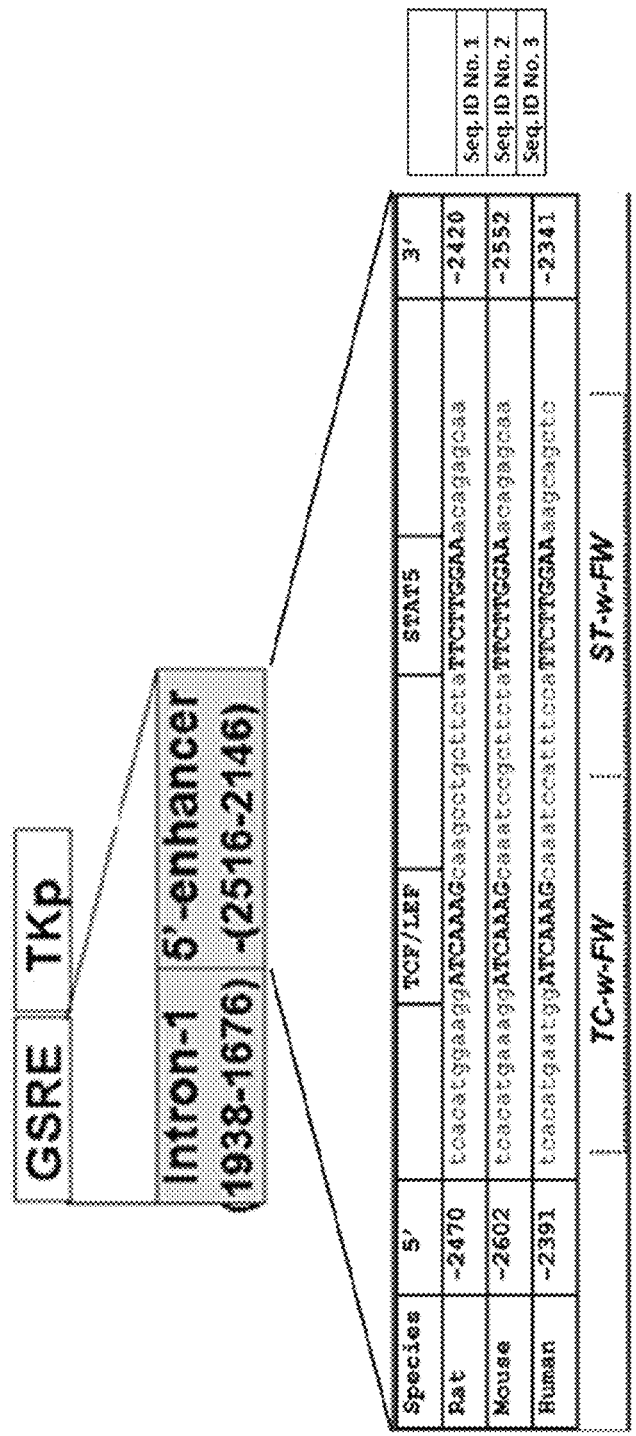
FIG. 11. GSRE contains Wnt signaling responding element-TCF-LEF binding site. A schematic presentation of GSRE indicating the presence of TCF-LEF and STAT 5 binding sites.
Figure 12:
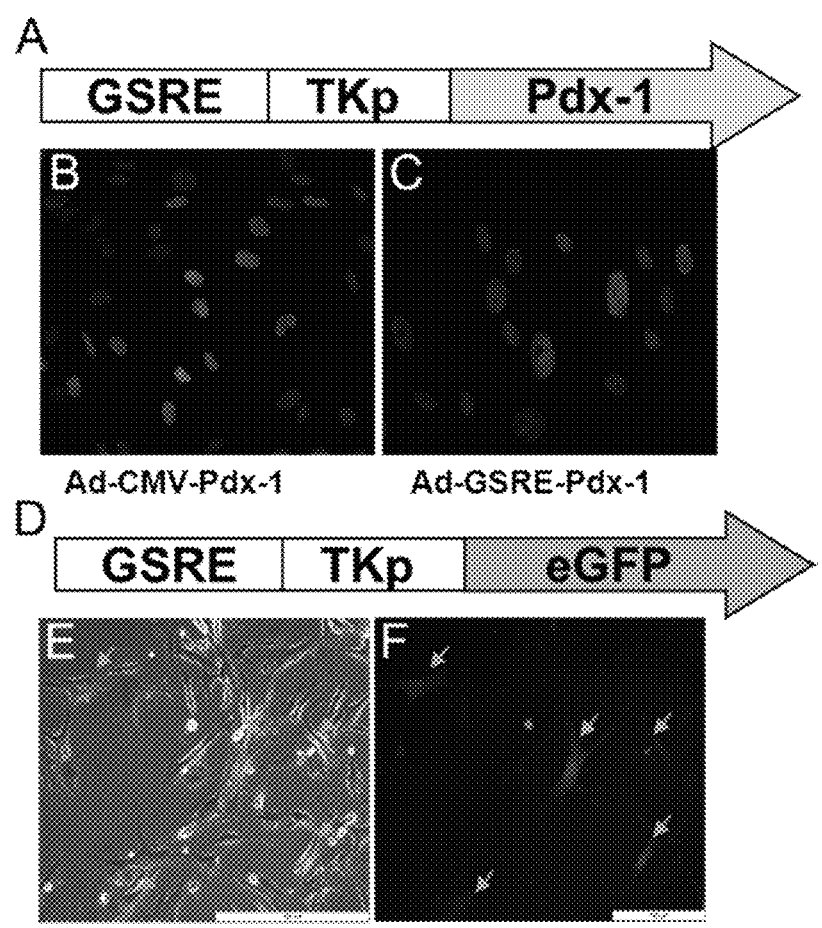
FIGS. 12A-12F. The GSRE targets subpopulation of human liver cells in vitro.

Example 11: GSRE Repetitively Targets 13-15% of the Human Liver Cells in Culture GSRE includes TCF/LEF and STAT5 binding elements (FIG. 11). Two recombinant adenoviruses which carry the expression of eGFP gene or Pdx-1 genes under the control of GSRE (FIG. 11) operatively linked to a minimal TK promoter (FIG. 11) have been generated. These adenoviruses drove the expression of either Pdx-1 (FIG. 12A) or eGFP (FIG. 12B). Both proteins were repetitively expressed in about 13-15% of the human liver cells in culture suggesting the targeting of a specific population of liver cells.

Figure 13:
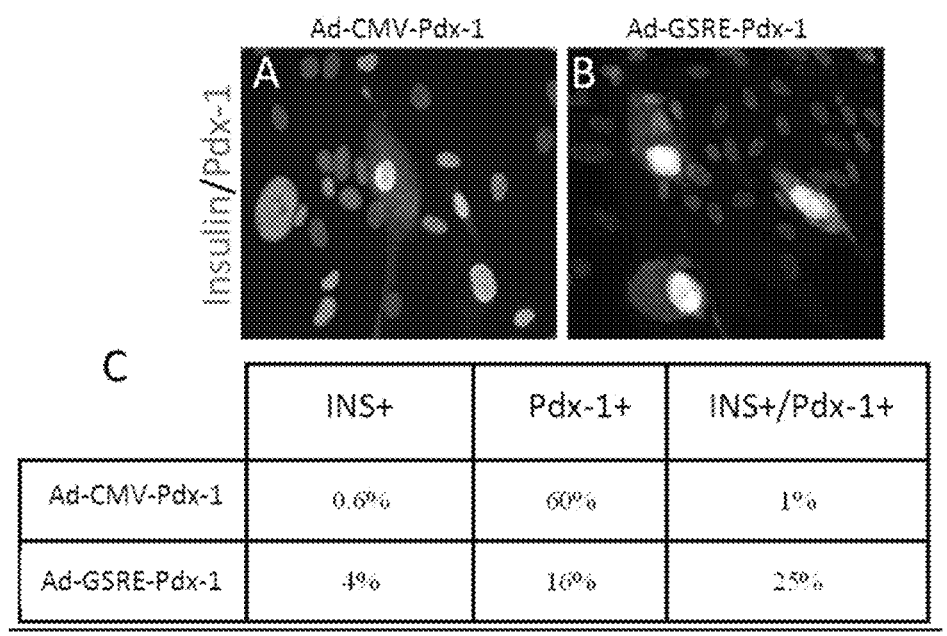
FIGS. 13A-13C. The GSRE targets transdifferentiation-prone cells. Liver cells were infected with Ad-GSRE-TK-Pdx-1 (FIG. 13B) or with Ad-CMV-Pdx-1 (FIG. 13A) for 5 days.

Example 12: GSRE Driven PDX-1 is More Efficient than CMV Driven PDX-1 in Activating Insulin Production in Liver Cells Despite the repetitive expression of GSRE driven PDX-1 only in about 13±2% of the cells in culture its transdifferentiation capacity was similar or higher than that induced by Ad-CMV-Pdx-1, which drives Pdx-1 expression in 60-80% of the cells in culture (FIG. 13). GSRE-activating cells could account for most of the transdifferentiation capacity of the entire adult human liver cells in culture. Insulin production occurred in 25% of Pdx-1 positive cells upon Ad-GSRE-Pdx-1 treatment compared to 1% of the Ad-CMV-Pdx-1 treated cells.

Example 13: Using Lentiviruses to Permanently Label the GSRE+ Cells by EGFP

Figure 15:
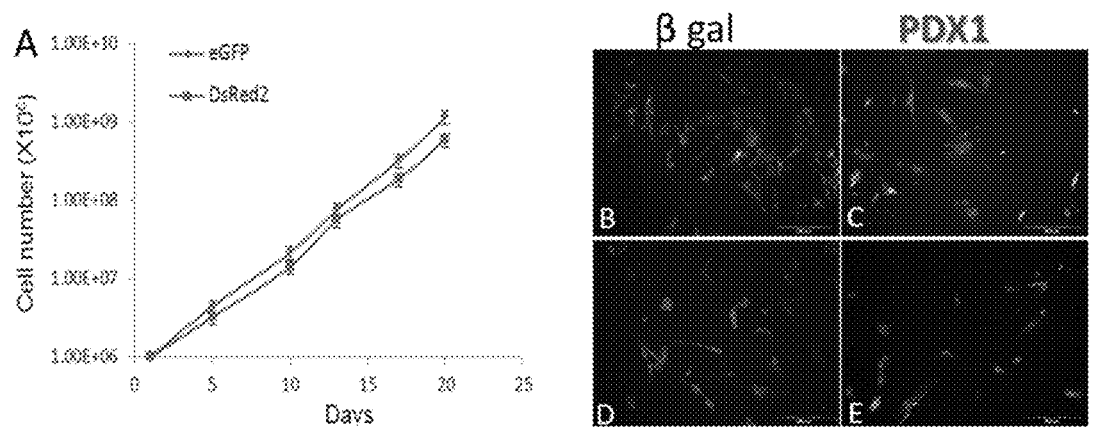
FIGS. 15A-15E. eGFP+ and DsRed2+ cells efficiently proliferate in vitro with a similar rate of proliferation and similar infection capacity. The separate populations of cells were cultured separately for ~1 month. The proliferation rate of each group was analyzed (FIG. 15A). eGFP+ (FIGS. 15B & 15C) and DsRed2+ (FIGS. 15D & 15E) cells were infected with Ad-CMV-β-gal (FIGS. 15B & 15D) or with Ad-CMV-Pdx-1 (FIGS. 15C & 15E) for 3 days. Immunofluorescent analysis using anti-Pdx-1 (blue) indicated that almost 80% of both eGFP and DsRed2 cells were infected by the adenovirus.

Permanent lineage tracing was performed using Lentivirus constructs. In vitro lineage tracing for GSRE activity was performed by a modified dual lentivirus system recently used to trace KRT5 in keratinocytes (Mauda-Havakuk, et al., PLoS One, 2011) or albumin (Meivar-Levy et al., J Transplant, 2011) expression in liver cells. This lentivirus system (a collaboration with Prof. P. Ravassard from Université Pierre et Marie Curie Paris, France; FIG. 12A) includes the CMV-loxP-DsRed2-loxP-eGFP (R/G) reporter (Meivar-Levy et al., J Transplan, 2011; Mauda-Havakuk et al., PLoS One, 2011; and Russ et al., Diabetes, 2008) and an additional lentiviral vector carrying the expression of Cre recombinase under the control of GSRE and a minimal TK promoter (generously contributed by Prof. Gaunitz, (Gebhardt et al., Prog Histochem Cytochem, 2007 and Gaunitz et al., Hepatology, 2005) Germany, FIG. 3A). Thus, GSRE-activating cells are irreversibly marked by eGFP (eGFP+), while the rest of the doubly infected cells are marked by DsRed2 (DsRed2+). Ten to fourteen percent of the cells became eGFP+ within less than 10 days (FIG. 14B). The cells were separated by a cell sorter (FIG. 14) and separately propagated (FIG. 15A). Cultures of eGFP+ (GSRE activators) and DsRed2+ cells were generated from 10 different human donors (ages 3-60).

Figure 16:
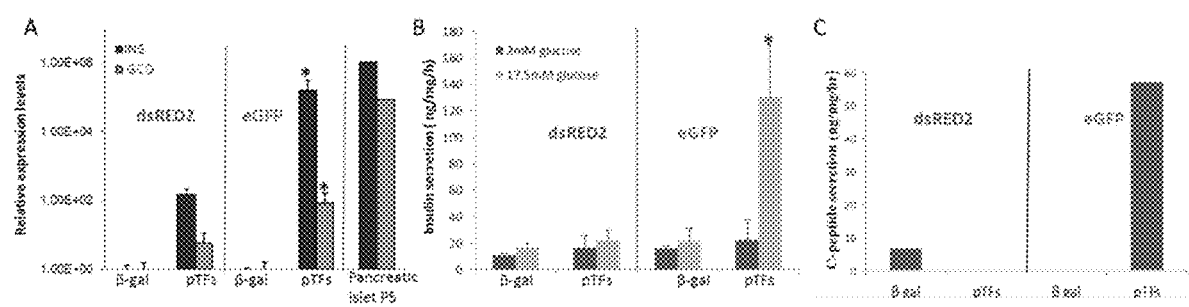
FIGS. 16A-16C. eGFP+ cells respond more efficiently than DsRed2+ cells to pTFs-induced transdifferentiation. The two groups were similarly treated with soluble factors and pTFs: Ad-Pdx-1+Ad-Pax-4+ad-MafA or a control virus (Ad-β-gal) for 6 days. β-cell-like characteristics and function was compared in the separated groups.

Example 14. EGFP+ Cells Consistently Exhibited Superior Transdifferentiation Capacity Human liver cells separated by lineage tracing according to GSRE activity efficiently propagated (FIG. 15A) and were similarly efficiently infected by recombinant adenoviruses. eGFP+ cells consistently exhibited superior transdifferentiation capacity (FIG. 16) manifested by insulin and glucagon gene expression which was comparable to that of human pancreatic islets in culture (FIG. 16A), glucose regulated insulin secretion (FIG. 16B) and glucose regulated C-peptide secretion (FIG. 16C). These capacities were consistent and did not diminished upon extensive cell proliferation, (FIG. 17).

Figure 18:
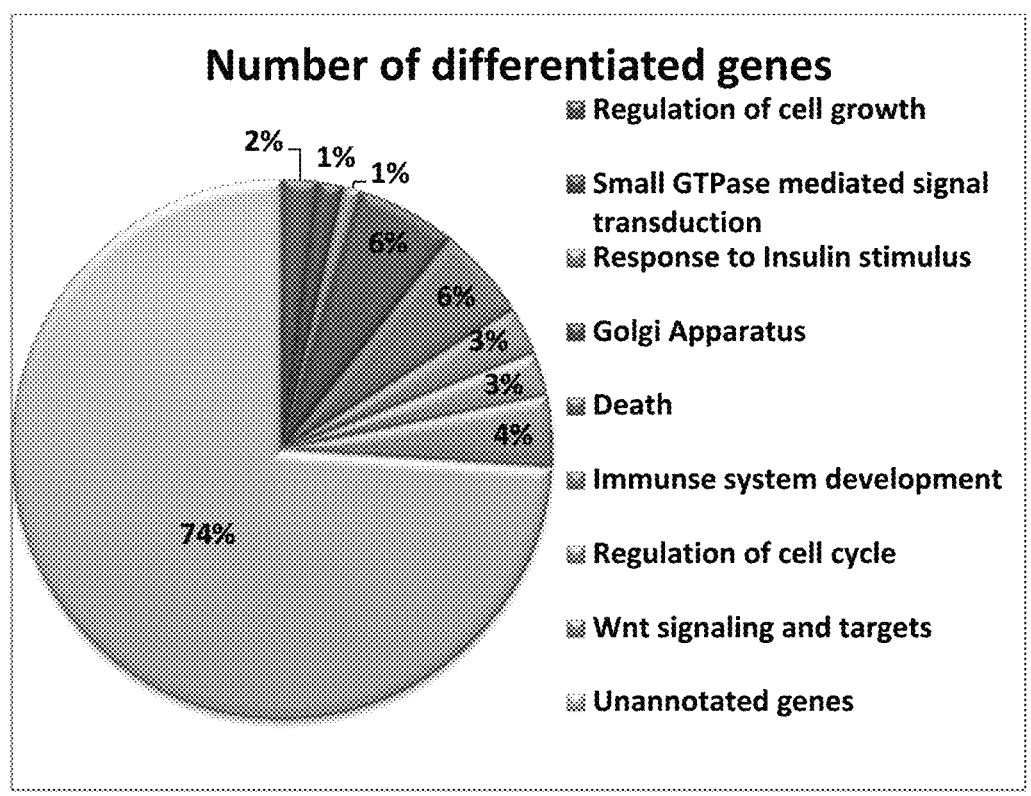
FIG. 18. Differential gene expression profiles of eGFP+ and DsRed2+ cells performed by microarray analyses and analyzed according to DAVID Bioinformatics Resources 6.7 Four Percent of the differential genes belong to the Wnt signaling pathway.

Example 15: Characterization of Cells with Predisposition for Transdifferentiation To identify the factors which could potentially affect the distinct transdifferentiation efficiencies of the human liver cells, we compared the global gene expression profile of the two separated populations using microarray chip analyses. Human liver cell cultures derived from 3 different donors and separated into eGFP+ and DsRed2+ cells and propagated for 4 passages. The extracted RNA was converted into cDNA and subjected to microarray chip analysis using the General Human Array (GeneChip Human Genome U133A 2.0 Array, Affymetrix). While most of the genes were expressed at comparable levels in the separated groups, the expression of about 800 probes was significantly different (FIG. 18). According to microarray chip analyses, about 100 genes coding for membrane proteins are differentially expressed between the transdifferentiation-prone (eGFP+) and non-responding (DsRed2+) cells. Several of these markers are presented in Table 2.

TABLE 2

Membrane antigens that are differentially expressed in eGFP+ and DsRed2+ cells.

| Antigene | High expression | Fold (Log 2) | p-value | commercial antibody |
|---|---|---|---|---|
| ABCB1 | DsRed2 | −6.363 | 1.52E−02 | BD Biosciences (#557002) |
| ITGA4 | DsRed2 | −1.979 | 2.69E−02 | R&D system (FAB1354G) |
| ABCB4 | DsRed2 | −4.42 | 4.62E−02 | Abcam (ab24108) |
| PRNP | DsRed2 | −1.35 | 4.20E−02 | eBioscience (12-9230-73) |
| HOMER1 | eGFP | 1.41 | 3.25E−04 | Biorbyt(orb37754) |
| LAMP3 | eGFP | 1.285 | 1.81E−02 | BD Biosciences (#558126) |
| BMPR2 | eGFP | 1.236 | 3.50E−02 | R&D system (AF811) |

Microarry data suggested numerous membrane proteins that are differential expression between the eGFP+ and the DsRed2+ cells (Fold=eGFP+ differential expression compared to the DsRed2+(log 2)). All the presented antigens have commercially available antibodies.

Example 16: Wnt Signaling is Active in Cells Predisposed for Transdifferentiation Liver zonation has been suggested to be controlled by a gradient of activated β-catenin levels; while most cells in the liver contain very low β-catenin activity, the pericentral liver cells express high β-catenin activity associated with active Wnt signaling (Gebhardt, et al., Frog Histochem Cytochem, 2007). Since Wnt signaling is obligatory for competent β cell activity (Liu et al., J Biol Chem, 2008; Liue et al., Adv Exp Med Biol, 2010; Loder et al., Biochem Soc Trans, 2008; and Shu et al., Diabetes, 2008), the pTFs-induced pancreatic lineage activiation in the liver is restricted to cells that a priori display active Wnt signaling.

GSRE utilized a TCF regulatory element isolated from the 5' enhancer of GS. If Pdx-1-induced liver to pancreas transdifferentiation is mediated in part by the intracellular Wnt signaling pathway, factors which modulate the Wnt signaling pathway should also affect transdifferentiation efficiency (FIG. 19).

Figure 19:
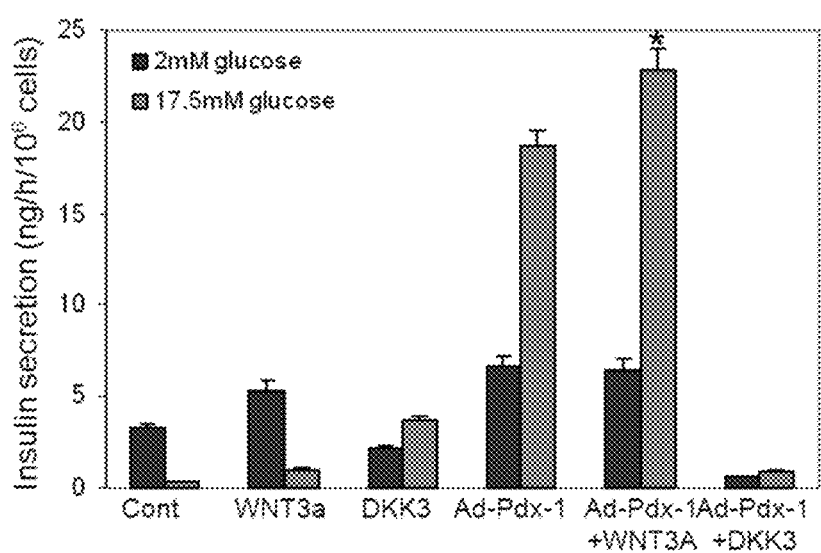
FIG. 19. The active Wnt signaling promotes liver to pancreas transdifferentiation. Adult human liver cells were treated with Ad-CMV-Pdx-1 and soluble factors, as previously reported, supplemented with Wnt3A (50 ng/ml R&D or DKK3 (3 µg/ml R&D). After 5 days, insulin secretion was analyzed by static incubations at low followed by high glucose concentrations (2 mM and 17.5 mM glucose in KRB, respectively). Insulin secretion is measured using the human insulin radioimmunoassay kit (DPC; n≥8 from 3 different experiments) and compared to untreated cells (Cont). *p<0.01 compared to Ad-CMV-Pdx-1 alone, using Student's t-test analysis.
Figure 20:
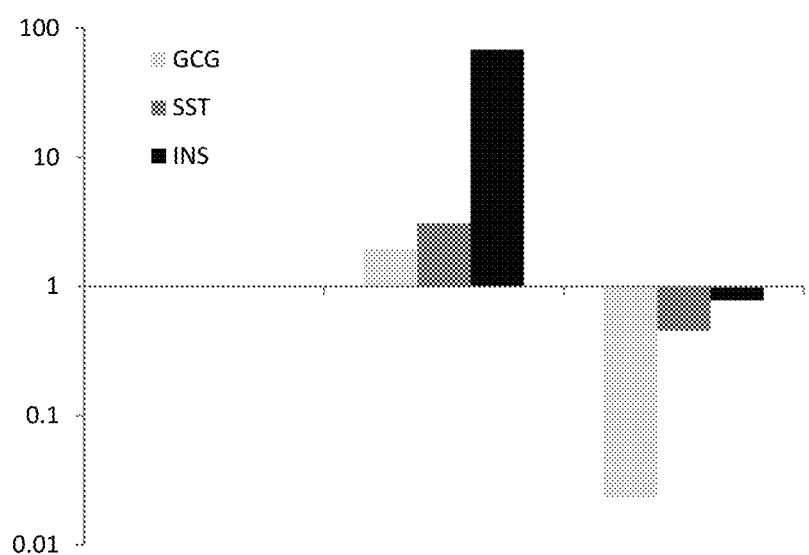
FIG. 20. Blocking Wnt signaling pathway abolishes the transdifferentiation of eGFP+ cells. eGFP cells were Ad-CMV-Pdx-1 or a control virus (Ad-CMV-β-gal) for 5 days supplemented with DKK3 (0.5 µg/ml R&D). Pancreatic hormones gene expression was studied by Quantitative real-time RT-PCR compared to the control-treated cells.

This data in adult human liver cells suggest that increasing concentrations of Wnt3a increased Pdx-1-induced glucose-regulated insulin secretion, while DKK3 (an inhibitor of the Wnt signaling pathway) completely abolished the effect of Pdx-1 on the process (FIG. 19). DKK3 also totally abolished the transdifferentiation capacity of the eGFP cells isolated according to their ability to activate GSRE (FIG. 20).

Figure 21:
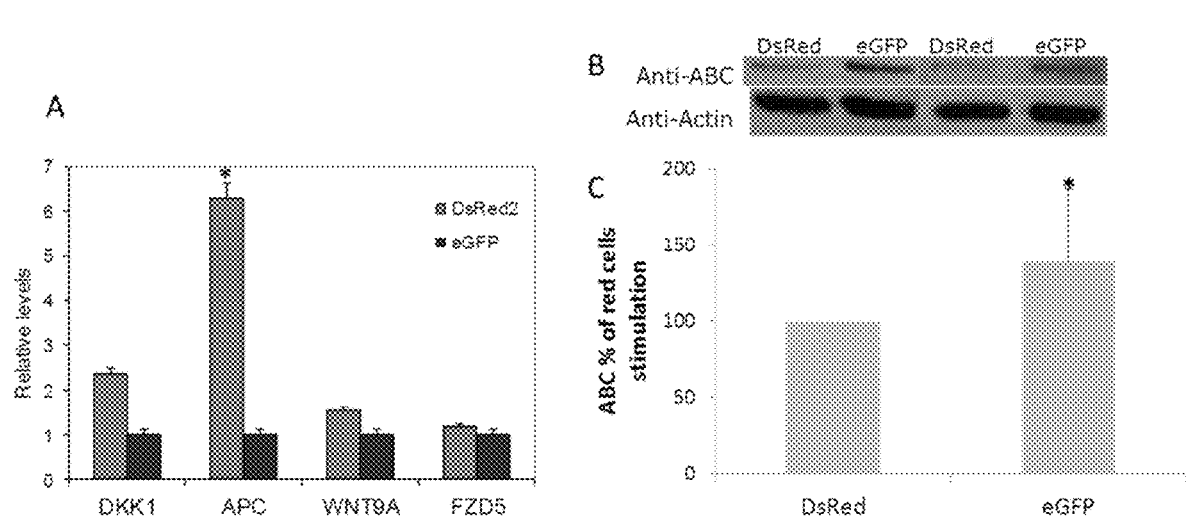
FIGS. 21A-21C. eGFP+ cells express lower levels of APC and higher levels of active β-catenin than DsRed2+ cells.

Characterization of Wnt signaling pathway activity in the eGFP+ and DsRed+ cell populations was performed. The APC expression, which participates in β-catenin destabilization, thus diminishing Wnt signaling, was 700% higher in DsRed2+ cells than in the eGFP+ cells (FIG. 21A, in relative agreement with the zonation displayed in vivo). The eGFP+ population has increased activated β-catenin levels (40%) compared to the levels analyzed in DsRed2+ cells (FIGS. 21B and C). These data demonstrate that Wnt signaling is active in cells that are competent for GSRE activation and have predisposition for transdifferentiation.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Ambasudhan, R., M. Talantova, et al. (2011). Direct reprogramming of adult human fibroblasts to functional neurons under defined conditions. Cell 9: 113-118.

Atala, A. (2008). Extending life using tissue and organ replacement. Curr Aging Sci 1: 73-83.

Aviv, V., I. Meivar-Levy, et al. (2009). Exendin-4 promotes liver cell proliferation and enhances PDX-1-induced liver to pancreas transdifferentiation. J Biol Chem 284: 33509-33520.

Ber, I., K. Shternhall, et al. (2003). Functional, persistent, and extended liver to pancreas transdifferentiation. J Biol Chem 278: 31950-31957.

Bernardo, A. S., C. W. Hay, et al. (2008). Pancreatic transcription factors and their role in the birth, life and survival of the pancreatic beta cell. Mol Cell Endocrinol 294: 1-9.

Bonal, C. and P. L. Herrera (2008). Genes controlling pancreas ontogeny. Int J Dev Biol 52: 823-835.

Borowiak, M. (2010). The new generation of beta-cells: replication, stem cell differentiation, and the role of small molecules. Rev Diabet Stud 7: 93-104.

Brun, T. and B. R. Gauthier (2008). A focus on the role of Pax4 in mature pancreatic islet beta-cell expansion and survival in health and disease. J Mol Endocrinol 40: 37-45.

Chakrabarti, S. K. and R. G. Mirmira (2003). Transcription factors direct the development and function of pancreatic b-cells. Trends Endocrinol Metab 14: 78-84.

Collombat, P., J. Hecksher-Sorensen, et al. (2006). Specifying pancreatic endocrine cell fates. Mech Dev 123: 501-512.

Collombat, P., A. Mansouri, et al. (2003). Opposing actions of Arx and Pax4 in endocrine pancreas development. Genes Dev 17: 2591-2603.

D'Amour, K. A., A. D. Agulnick, et al. (2005). Efficient differentiation of human embryonic stem cells to definitive endoderm. Nat Biotechnol. 23: 1534-1541.

Eberhard, D. and E. Lammert (2009). The pancreatic beta-cell in the islet and organ community Curr Opin Genet Dev 19: 469-475.

Ferber, S., A. Halkin, et al. (2000). Pancreatic and duodenal homeobox gene 1 induces expression of insulin genes in liver and ameliorates streptozotocin-induced hyperglycemia. Nat Med 6: 568-572.

Gefen-Halevi, S., I. H. Rachmut, et al. (2010). NKX6.1 promotes PDX-1-induced liver to pancreatic beta-cells reprogramming Cell Reprogram 12: 655-664.

Gradwohl, G., A. Dierich, et al. (2000). neurogenin3 is required for the development of the four endocrine cell lineages of the pancreas. Proc Natl Acad Sci USA 97: 1607-1611.

Hanna, J., S. Markoulaki, et al. (2008). Direct reprogramming of terminally differentiated mature B lymphocytes to pluripotency. Cell 133: 250-264.

He, T. C., S. Zhou, et al. (1998). A simplified system for generating recombinant adenoviruses. Proc Natl Acad Sci USA 95: 2509-2514.

Ieda, M., J. D. Fu, et al. (2010). Direct reprogramming of fibroblasts into functional cardiomyocytes by defined factors. Cell. 142: 375-386.

Iwasaki, H., S. Mizuno, et al. (2006). The order of expression of transcription factors directs hierarchical specification of hematopoietic lineages. Genes Dev 20: 3010-3021.

Kaneto, H., T. A. Matsuoka, et al. (2005). A crucial role of MafA as a novel therapeutic target for diabetes. J Biol Chem 280: 15047-15052.

Kaneto, H., Y. Nakatani, et al. (2005). PDX-1/VP16 fusion protein, together with NeuroD or Ngn3, markedly induces insulin gene transcription and ameliorates glucose tolerance. Diabetes 54: 1009-1022.

Kataoka, K., S. I. Han, et al. (2002). MafA is a glucose-regulated and pancreatic beta-cell-specific transcriptional activator for the insulin gene. J Biol Chem 277: 49903-49910.

Koizumi, M., R. Doi, et al. (2004). Hepatic regeneration and enforced PDX-1 expression accelerate transdifferentiation in liver. Surgery 136: 449-457.

Kojima, H., M. Fujimiya, et al. (2003). NeuroD-betacellulin gene therapy induces islet neogenesis in the liver and reverses diabetes in mice. Nat Med 9: 596-603.

Kroon, E., L. A. Martinson, et al. (2008). Pancreatic endoderm derived from human embryonic stem cells generates glucose-responsive insulin-secreting cells in vivo. Nat Biotechnol 26: 443-452.

Meivar-Levy, I. and S. Ferber (2003). New organs from our own tissues: liver-to-pancreas transdifferentiation. Trends Endocrinol Metab 14: 460-466.

Meivar-Levy, I. and S. Ferber (2006). Regenerative medicine: using liver to generate pancreas for treating diabetes. Isr Med Assoc J. 8: 430-434.

Meivar-Levy, I. and S. Ferber (2010). Adult cell fate reprogramming: converting liver to pancreas. Methods Mol. Biol. 636: 251-283.

Meivar-Levy, I., T. Sapir, et al. (2011). Human liver cells expressing albumin and mesenchymal characteristics give rise to insulin-producing cells. J Transplant 2011: 252387.

Meivar-Levy, I., T. Sapir, et al. (2007). Pancreatic and duodenal homeobox gene 1 induces hepatic dedifferentiation by suppressing the expression of CCAAT/enhancer-binding protein beta. Hepatology 46: 898-905.

Murtaugh, L. C. and D. A. Melton (2003). Genes, signals, and lineages in pancreas development. Annu Rev Cell Dev Biol 19: 71-89.

Nishimura, W., S. Bonner-Weir, et al. (2009). Expression of MafA in pancreatic progenitors is detrimental for pancreatic development. Dev Biol 333: 108-120.

Offield, M. F., T. L. Jetton, et al. (1996). PDX-1 is required for pancreatic outgrowth and differentiation of the rostral duodenum. Development 122: 983-995.

Olbrot, M., J. Rud, et al. (2002). Identification of beta-cell-specific insulin gene transcription factor RIPE3b1 as mammalian MafA. Proc Natl Acad Sci USA 99: 6737-6742.

Pang, Z. P., N. Yang, et al. (2011). Induction of human neuronal cells by defined transcription factors. Nature 476: 220-223.

Russ, H. A. and S. Efrat (2011). Development of human insulin-producing cells for cell therapy of diabetes. Pediatr Endocrinol Rev 9: 590-597.

Sapir, T., K. Shternhall, et al. (2005). From the Cover: Cell-replacement therapy for diabetes: Generating functional insulin-producing tissue from adult human liver cells. Proc Natl Acad Sci USA 102: 7964-7969.

Seijffers, R., O. Ben-David, et al. (1999). Increase in PDX-1 levels suppresses insulin gene expression in RIN 1046-38 cells. Endocrinology 140: 3311-3317.

Sheyn, D., O. Mizrahi, et al. (2010). Genetically modified cells in regenerative medicine and tissue engineering. Adv Drug Deliv Rev 62: 683-698.

Slack, J. M. and D. Tosh (2001). Transdifferentiation and metaplasia—switching cell types. Curr Opin Genet Dev 11: 581-586.

Song, Y. D., E. J. Lee, et al. (2007). Islet cell differentiation in liver by combinatorial expression of transcription factors neurogenin-3, BETA2, and RIPE3b1. Biochem Biophys Res Commun. 354: 334-339. .

Stoffers, D. A., M. K. Thomas, et al. (1997). The homeodomain protein IDX-1. Trends Endocrinol. & Metab. 8: 145-151.

Szabo, E., S. Rampalli, et al. (2010). Direct conversion of human fibroblasts to multilineage blood progenitors. Nature 468: 521-526.

Takahashi, K. and S. Yamanaka (2006). Induction of pluripotent stem cells from mouse embryonic and adult fibroblast cultures by defined factors. Cell 126: 663-676.

Tang, D. Q., L. Z. Cao, et al. (2006). Role of Pax4 in Pdx1-VP16-mediated liver-to-endocrine pancreas transdifferentiation. Lab Invest. 86: 829-841.

Varda-Bloom, N., A. Shaish, et al. (2001). Tissue-specific gene therapy directed to tumor angiogenesis. Gene Ther 8: 819-827.

Vierbuchen, T., A. Ostermeier, et al. (2010). Direct conversion of fibroblasts to functional neurons by defined factors. Nature 463: 1035-1041.

Wang, A. Y., A. Ehrhardt, et al. (2007). Adenovirus Transduction is Required for the Correction of Diabetes Using Pdx-1 or Neurogenin-3 in the Liver. Mol Ther 15: 255-263.

Yamanaka, S. (2008). Induction of pluripotent stem cells from mouse fibroblasts by four transcription factors. Cell Prolif. 41: 51-56.

Yechoor, V. and L. Chan (2010). Minireview: beta-cell replacement therapy for diabetes in the 21st century: manipulation of cell fate by directed differentiation. Mol Endocrinol 24: 1501-1511.

Zhou, Q., J. Brown, et al. (2008). In vivo reprogramming of adult pancreatic exocrine cells to beta-cells. Nature 455: 627-632.

What is claimed is:

1. A method of isolating a population of cells that have an enriched capacity for transcription factor induced transdifferentiation:
   (a) providing a heterogeneous population of human cells;
   (b) introducing a nucleic acid construct comprising a glutamine synthetase response element (GSRE), or fragment thereof capable of activating glutamine synthetase transcription, operatively linked to a reporter protein;
   (c) identifying the cells expressing the reporter protein; and
   (d) isolating the cells expressing the reporter protein;
   thereby isolating a cell population with enriched transdifferentiation capacity.

2. The method of claim 1, wherein said GSRE or fragment thereof comprises a T-cell factor/lymphoid enhancer-binding factor (TCF/LEF) binding element, a Signal transducer and activator of transcription 5 (STAT5) binding element, or a combination thereof.

3. The method of claim 1, wherein in the nucleic acid construct further comprises a promoter, an enhancer, or a combination thereof.

4. The method of claim 1, wherein the reporter protein is a fluorescent protein.

5. The method of claim 4, wherein said isolating step comprises sorting said cells based on fluorescent emission of said reporter protein.

6. The method of claim 1, wherein the reporter protein provides resistance to selection pressure.

7. The method of claim 1, wherein the cells are endothelial cells, fibroblasts, mesenchymal or liver cells.

8. The method of claim 7, wherein said liver cells comprise primary adult liver cells.

9. The method of claim 7, wherein the liver cells are derived from the pericentral liver.

10. The method of claim 1, further comprising a step of culturing the isolated cells, following said isolation.

11. The method of claim 10, wherein said cultured cells maintain an enriched capacity for transcription factor induced transdifferentiation for at least five generations.

12. The method of claim 1, wherein said nucleic acid construct comprises an adenoviral vector or a lentiviral vector.

* * * * *

```
                               SEQUENCE LISTING

<160> NUMBER OF SEQ ID NOS: 3

<210> SEQ ID NO 1
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 1
tcacatggaa ggatcaaagc aagcctgctt ctattcttgg aaacagagca a          51

<210> SEQ ID NO 2
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 2
tcacatgaaa ggatcaaagc aaatccgctt ctattcttgg aaacagagca a          51

<210> SEQ ID NO 3
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 3
tcacatgaat ggatcaaagc aaatccattt ccattcttgg aaaagcagct c          51
```